(12) United States Patent
Lockwood et al.

(10) Patent No.: US 7,247,752 B2
(45) Date of Patent: Jul. 24, 2007

(54) METHODS FOR THE SYNTHESIS OF ASTAXANTHIN

(75) Inventors: Samuel F. Lockwood, Lago Vista, TX (US); Peng Cho Tang, Moraga, CA (US); Geoff Nadolski, Kasole, HI (US); Henry L. Jackson, Honolulu, HI (US); Zhiqiang Fang, Hawthorn Woods, IL (US); Yishu Du, Shanghai (CN); Min Yang, Vernon Hills, IL (US); William Geiss, Athens, NY (US); Richard Williams, Nashville, TN (US); David Burdick, Guilderland, NY (US)

(73) Assignee: Cardax Pharmaceuticals, Inc., Aiea, HI (US)

( * ) Notice: Subject to any disclaimer, the term of this patent is extended or adjusted under 35 U.S.C. 154(b) by 0 days.

(21) Appl. No.: 11/242,643

(22) Filed: Oct. 3, 2005

(65) Prior Publication Data

US 2006/0183947 A1   Aug. 17, 2006

Related U.S. Application Data

(60) Provisional application No. 60/712,350, filed on Aug. 30, 2005, provisional application No. 60/702,380, filed on Jul. 26, 2005, provisional application No. 60/699,653, filed on Jul. 15, 2005, provisional application No. 60/692,682, filed on Jun. 21, 2005, provisional application No. 60/691,518, filed on Jun. 17, 2005, provisional application No. 60/675,957, filed on Apr. 29, 2005, provisional application No. 60/615,032, filed on Oct. 1, 2004.

(51) Int. Cl.
   *C07C 45/00*   (2006.01)
(52) U.S. Cl. ..................... 568/343; 568/378
(58) Field of Classification Search ............. None
   See application file for complete search history.

(56) References Cited

U.S. PATENT DOCUMENTS

| | | | |
|---|---|---|---|
| 3,206,316 A | 9/1965 | Klaui | |
| 3,354,218 A | 11/1967 | Surmatis | |
| 3,755,422 A | 8/1973 | Morel | |
| 3,989,757 A | 11/1976 | Surmatis | |
| 4,245,109 A * | 1/1981 | Mayer et al. | 560/61 |
| 4,283,559 A * | 8/1981 | Broger et al. | 568/11 |
| 4,435,427 A | 3/1984 | Hoppe et al. | |
| 4,585,885 A * | 4/1986 | Bernhard et al. | 556/436 |
| 4,952,716 A * | 8/1990 | Lukac et al. | 556/482 |
| 5,227,507 A | 7/1993 | Lukac et al. | |
| 5,310,554 A | 5/1994 | Haigh | |
| 5,328,845 A | 7/1994 | Finkelstein et al. | |
| 5,364,563 A | 11/1994 | Cathrein et al. | |
| 5,422,247 A | 6/1995 | Finkelstein et al. | |
| 5,455,362 A | 10/1995 | Ernst et al. | |
| 5,492,701 A | 2/1996 | Cervos et al. | |
| 5,536,504 A | 7/1996 | Eugster et al. | |
| 5,543,559 A | 8/1996 | Broger et al. | |
| 5,607,839 A | 3/1997 | Tsubokura et al. | |
| 5,612,485 A | 3/1997 | Schlipalius | |
| 5,654,488 A | 8/1997 | Krause et al. | |
| 5,849,345 A | 12/1998 | Giger et al. | |
| 5,854,015 A | 12/1998 | Garnett et al. | |
| 5,858,700 A | 1/1999 | Ausich et al. | |
| 5,871,766 A | 2/1999 | Hennekens | |
| 5,876,782 A | 3/1999 | Sas et al. | |
| 5,959,138 A | 9/1999 | Torres-Cardona et al. | |
| 6,020,003 A | 2/2000 | Stroh et al. | |
| 6,046,181 A | 4/2000 | Oonishi et al. | |
| 6,060,511 A | 5/2000 | Gainer | |
| 6,245,818 B1 | 6/2001 | Lignell | |
| 6,335,015 B1 | 1/2002 | Lignell et al. | |
| 6,540,654 B2 | 4/2003 | Levy et al. | |
| 6,610,892 B2 | 8/2003 | Ernst et al. | |
| 6,673,971 B2 | 1/2004 | Wegner et al. | |
| 6,747,177 B2 * | 6/2004 | Ernst et al. | 568/828 |
| 6,827,941 B1 | 6/2004 | Luddecke et al. | |
| 2003/0143660 A1 | 7/2003 | Cheng et al. | |
| 2004/0049082 A1 | 3/2004 | Wegner et al. | |
| 2004/0162329 A1 | 8/2004 | Lockwood et al. | |
| 2005/0004235 A1 | 1/2005 | Lockwood et al. | |
| 2005/0009758 A1 | 1/2005 | Lockwood et al. | |
| 2005/0009788 A1 | 1/2005 | Lockwood et al. | |
| 2005/0009930 A1 | 1/2005 | Lockwood et al. | |
| 2005/0026874 A1 | 2/2005 | Lockwood et al. | |

(Continued)

FOREIGN PATENT DOCUMENTS

CH   685 189   4/1995

(Continued)

OTHER PUBLICATIONS

Tanaka et al. Tetrahedron: Asymmetry, 1995, vol. 6 (6), p. 1273-1278.*

(Continued)

*Primary Examiner*—Sikarl A. Witherspoon
(74) *Attorney, Agent, or Firm*—Meyertons, Hood, Kivlin, Kowert & Goetzel, P.C.; Eric B. Meyertons

(57) ABSTRACT

A method used for synthesizing intermediates for use in the synthesis of carotenoids and carotenoid analogs, and/or carotenoid derivatives. In some embodiments, the invention includes methods for synthesizing optically active intermediates useful for the synthesis of optically active carotenoids. Synthesis of optically active carotenoids, in one embodiment, may be accomplished by forming an optically active dihydroxy intermediate from ketoisopherone. The optically active dihydroxy intermediate may be converted into optically active astaxanthin derivatives.

34 Claims, 1 Drawing Sheet

U.S. PATENT DOCUMENTS

| | | |
|---|---|---|
| 2005/0037995 A1 | 2/2005 | Lockwood et al. |
| 2005/0049248 A1 | 3/2005 | Lockwood et al. |
| 2005/0059635 A1 | 3/2005 | Lockwood et al. |
| 2005/0059659 A1 | 3/2005 | Lockwood et al. |
| 2005/0065096 A1 | 3/2005 | Lockwood et al. |
| 2005/0065097 A1 | 3/2005 | Lockwood et al. |
| 2005/0075316 A1 | 4/2005 | Lockwood et al. |
| 2005/0075337 A1 | 4/2005 | Lockwood et al. |
| 2005/0090469 A1 | 4/2005 | Lockwood et al. |
| 2005/0113372 A1 | 5/2005 | Lockwood et al. |
| 2005/0143475 A1 | 6/2005 | Lockwood et al. |
| 2005/0148517 A1 | 7/2005 | Lockwood et al. |
| 2005/0261254 A1 | 11/2005 | Lockwood et al. |
| 2006/0058269 A1 | 3/2006 | Lockwood et al. |
| 2006/0088904 A1 | 4/2006 | Lockwood et al. |
| 2006/0088905 A1 | 4/2006 | Lockwood et al. |
| 2006/0111580 A1 | 5/2006 | Lockwood et al. |
| 2006/0155150 A1 | 7/2006 | Lockwood et al. |
| 2006/0167319 A1 | 7/2006 | Lockwood et al. |
| 2006/0178538 A1 | 8/2006 | Lockwood et al. |
| 2006/0183185 A1 | 8/2006 | Lockwood et al. |
| 2006/0183947 A1 | 8/2006 | Lockwood et al. |
| 2006/0229446 A1 | 10/2006 | Lockwood et al. |

FOREIGN PATENT DOCUMENTS

| | | |
|---|---|---|
| DE | 2101869 | 7/1971 |
| EP | 0 085 158 | 6/1985 |
| EP | 1 044 954 | 10/2000 |
| JP | 07-300421 | 11/1995 |
| JP | 08-073312 | 3/1996 |
| JP | 08-337592 | 12/1996 |
| JP | 09-084591 | 3/1997 |
| JP | 09202730 | 8/1997 |
| JP | 10-327865 | 12/1998 |
| WO | WO 02/068385 | 9/2002 |
| WO | WO 03/066583 | 8/2003 |
| WO | WO/2004/011423 | 2/2004 |
| WO | WO 05/056507 | 6/2005 |
| WO | WO/2005/102356 | 11/2005 |
| WO | WO/2006/039685 | 4/2006 |

OTHER PUBLICATIONS

Shibagaki et al. "The Catalytic Reduction of Aldehydes and Ketones with 2-Propanol over Hydrous Zirconium Oxide" Bull. Chem. Soc. Jpn., 61, 3283-3288 (1988).

Corey et al. "Reduction of Carbonyl Compounds with Chiral Oxazaborolidine Catalysts: A New Paradigm for Enantioselective Catalysis and a Powerful New Synthetic Method" Angew. Chem. Intl. Ed., 37, 15, (1998) 1986-2012.

Co-Pending U.S. Appl. No. 11/392,470 entitled, "Reduction in Complement Activation and Inflammation During Tissue Injury by Carotenoids, Carotenoid Analogs, or Derivatives Thereof" to Lockwood et al. filed Mar. 29, 2006; available in private PAIR.

Co-Pending U.S. Appl. No. 11/359,984 entitled, "Carotenoids, Carotenoid Analogs, or Carotenoid Derivatives for the Stabilization or Improvement of Visual Acuity" to Lockwood et al. filed Feb. 22, 2006; available in private PAIR.

Co-Pending U.S. Appl. No. 11/388,237 entitled, "Water-Dispersible Carotenoids, Including Analogs and Derivatives" to Lockwood et al. filed Mar. 23, 2006; available in private PAIR.

Co-Pending U.S. Appl. No. 11/372,353 entitled, "Carotenoids, Carotenoid Analogs, or Carotenoid Derivatives for the Treatment of Proliferative Disorders" to Lockwood et al. filed Mar. 9, 2006; available in private PAIR.

Co-Pending U.S. Appl. No. 11/417,307 entitled, "Use of Carotenoids and/orCarotenoid Derivatives/Analogs for Reduction/Inhibition of Certain Negative Effects of Cox Inhibitors" to Lockwood et al. filed May 2, 2006; available in private PAIR.

Co-Pending U.S. Appl. No. 11/415,375 entitled, "Methods for Synthesis of Carotenoids, Including Analogs, Derivatives, and Synthetic and Biological Intermediates" to Lockwood et al. filed May 1, 2006; available in private PAIR.

International Search Report (ISR) mailed Apr. 27, 2006, for PCT/US2005/035599 to Lockwood et al. filed Mar. 10, 2005.

Office Action for U.S. Appl. No. 11/242,639 mailed on Oct. 10, 2006.

Andrewes et al. "Animal carotenoids. 9. On the absolute configuration of astaxanthin and actinioerythrin." Acta Chem. Scand. (1974), B28:730-736.

Bauernfeind "Carotenoid Vitamin A Precursors and Analogs in Food and Feeds" J. Agric. Food Chem. (1972) 20, 456.

Ben-Amotz, A., and Levy, Y. "Bioavailability of a natural isomer mixture compared with synthetic all-trans beta-carotene in human serum." Am J Clin Nutr (1996). 63: 729-734.

Bernhard et al. "Synthesis of optically-active natural carotenoids and structurally related-compounds. 9. Synthesis of (3R)-hydroxyechinenone, (3R,3'R)-adonixanthin and (3R,3'S)-adonixanthin, (3R)-adonirubin, their optical antipodes and related-compounds." Helv. Chim. Acta. (1981), 64:2469-2484. Summary Engl. Article German.

Bock et al. "Preparation of some bromodeoxyaldonic acids." Carb. Res. (1979), 68:313-319.

Britton, G. "Structure and properties of carotenoids in relation to function." The FASEB Journal, (1995) 9: 1551-1558.

Britton, G., et al., "Carotenoids: Isolation and Analysis," Birkhauser: Basel, vol. la, (1995), p. 82.

Bouvier et al. "Biosynthesis of the Food and Cosmetic Plant Pigment Bixin (Annatto)" Science, (2003) 300: 2089-2091 (Jun. 27, 2003).

Ding and Hu. "The synthesis of vicinal halohydrin phosphates via highly regioselective ring opening of epoxides with dialkyl halophophate." J. Chem. Chem. Soc., Perkin Trans. (2000) 1:1651-1655.

Duhamel et al., "Terminally substituted linear conjugated polyenes: precursors of molecular wires." Tetrahedron Letters (1993), vol. 34, pp. 7399-7400.

Harada and Nakanishi "Circular Dichroic Spectroscopy—Exciton Coupling in Organic Stereochemistry", (1983), University Science Books, Mill Valley (CA).

Harada et al. "Circular dichroic power due to chiral exciton coupling between two polyacene chromophores." J. Am. Chem. Soc. (1978), 100:4029-4036.

Harada, N., et al, "The Exciton Chirality Method and Its Application to Configurational and Conformational Studies of Natural Products," Accounts of Chemical Research, vol. 5, No. 8, Aug. (1972), pp. 257-263.

Hengartner et al. "Synthesis, Isolation, and NMR-Spectroscopic Characterization of Fourteen (Z)-Isomers of Lycopene and Some Acetylenic Didehydro- and Tetradehydrolycopenes" Helv. Chim. Acta (1992) 75, 1848.

Hennig et al. "Synthesis of (R)- and (S)-Hydroxyisophorone by Ruthenium-catalyzed Asymmetric Transfer Hydrogenation of Ketoisopherone" Tetrahedron:Asymmetry; (2000) 11(6), 1849-1858.

Hieber et al. "Plant Lipocalins: Violaxanthin De-epoxidase and Zeaxanthin Epoxidase" Biochim. Biophys. Acta (2000), 1482, 84-91.

Ishihara et al. "Identification of New Constituents of Quince Fruit Flavor" J. Org. Chem. (1986) 51 491.

Johnson et al. "Astaxanthin from Microbial Sources" Crit. Rev. Biotechnol. (1991) 11, 297.

Jouni, Z., et al, "Purification and Partial Characterization of a Lutein-binding Protein from the Midgut of the Silkworm *Bombyx mori*\*," The Journal of Biological Chemistry, vol. 271, No. 25, Issue of Jun. 21, , (1996), pp. 14722-14726.

Kelly et al. "Carotenoids of Higher Plants. 4. The Stereochemistry of Lycoxanthin and Lycophyll" Chem. Scand., Ser. A (1971) 25, 1607.

Kiyota et al. "Hydrolase-Catalyzed Preparation of (R)- and (S)-4-hydroxy-2,6,6-trimethyl-2-cyclohexen-1-ones (Phorenols), the Key Synthetic Intermediates for Abscisic Acid" Tetrahedron:Asymmetry (1999) 10:19, 3811.

Larock VCH Publishers, Inc. (1989) pp. 456-461.

Liao, M.-L., Ying, X.-Y., Chung, C., Liang, Y.-T. and Sieb, P.A. (1988) Synthesis of L-ascorbate and 6-phosphate. Carb. Res. 176: 73-77.

Liu et al. "Didehydrogeranylgeranyl (DDGG): A Fluorescent Probe for Protein Prenylation" J. Am. Chem. Soc. (2002) 124, 20.

Lutnaes et al. "Is (9Z)-'meso'-zeaxanthin optically active?" Chirality (2001). 13: 224-229.

Mashovsky, M. D. Tocopherol acetate (*Tocopheroli acetas*) 6-Acetoxy-2-methyl-2-(4,8,12-trimethyltridecyl)-chromane. pp. 37-38. Aevit (Aevitum). p. 41. Acetysalicylic acid (Acidum acetylsalicylicum). p. 190. (1988), In Medicinal Substances, Part 2, 1988. (Russian, abstracts in English).

Müller et al. "Contribution to the analytical separation and the synthesis of 3-hydroxy-4-oxocarotenoids." "Beitrag zur Analytik un Synthese von 3-Hydroxy-4-oxocarotinoiden," Helv. Chim. Acta (1980), 63:1654-1664. German, Abstract Engl.

Orset and Young "Exposure to low irradiances favors the synthesis of 9-cis beta,beta carotene in *Dunaliella salina* (Teod.)." Plant Physiol (2000). 122: 609-617.

Pfander et al. "Carotenoid Synthesis: A Progress Report" Pure Appl. Chem. (1997) 69, 2047.

Ruttimann "Dienolether Condensations—a Powerful Tool inCarotenoid Synthesis" Pure Appl. Chem. (1999) 71, 2285.

Salomon et al. "Efficient and Selective Dealkylation of Phosphonte Diisopropyl Resins" Tetrahedron Lett. (1995) 36, 6759.

Savignac et al. Bull. Soc. Chim. Fr. (1974), 7, 1506.

Smith et al. "The Methyl Group as Phosphate Protecting Group in Nucleotide Synthesis" Tetrahedron Lett. (1980) 21, 861.

Stowell et al. "A New Method for the Phosphorylation of Alcohols and Phenols" Tetrahedron Lett. (1995) 36, 1825.

Stuber et al. "A new synthesis of L-threo-hex-2-enaro-1,4-lactone ("saccharoascorbic" acid): a method for the protection of the enediol of ascorbic acid." Carb. Res. (1978), 60:251-258.

Tanaka et al. "Lipase-Catalyzed Asymmetric Synthesis of (R)- and (S)-4-tert-Butyldimethylsiloxy-2,6,6-trimethyl-2-cyclohexanone and Their Dihydro Derivatives" Tetrahedron: Assymetry, (1995) vol. 6 (6), 1273-1278.

Widmer et al. "Techincal Procedures for the Synthesis of Carotenoids and Related Compounds from 6-oxo-isophorone II. A Novel Concept for the Synthesis of (3R, 3'RS)-Astaxanthin" Helv. Chemica Acta (1981) 239, 2436-2447.

Yuan, J., et al., "Isomerization of trans-Astaxanthin to cis-Isomers in Organic Solvents," J. Agric. Food Chem.,47, (1999), pp. 3656-3660.

Zell et al. "Technical Procedures for the Synthesis of Carotenoids and Related Compounds from 6-oxo-isophorone III. A New Concept for the Synthesis of the Enatiomeric Astaxanthins" Helv. Chemica Acta, (1981) 64, 2447-2462.

Zell et al. "Technical Procedures for the Synthesis of Carotenoids and Related Compounds from 6-oxo-isophorone IV. A New Concept for the Synthesis of (3RS,3'RS)-, (3S,3'S)- and (3R,3'R)-9,9'-dicis-7,8,7',8'-Tetradehydroastaxanthin" Helv. Chemica Acta, (1981) 64, 2463-2468.

Zsila et al.. "Supramolecular assemblies of carotenoids." Chirality, (2001), 13:739-744.

Kjosen et al. "Carotenoids of Higher Plants 6. Total Synthesis of Lycoxanthin and Lycophyll" Acta. Chem. Scand. 26 (1972) 10 4121-4129.

Ernst, "Recent Advances in Industrial Carotenoid Synthesis" Pure Appl. Chem., vol. 74, No. 11, pp. 2213-2226 (2002).

Rosenberger et al. "Canthaxanthin. A New Total Synthesis" J. Org. Chem. (1982) 47, 2130-2134.

Widmer et al. "Techincal Procedures for the Synthesis of Carotenoids and Related Compounds from 6-oxo-isophorone I. Modification of the Kienzle-Mayer-Synthesis of (3S, 3'S)-Astaxanthin" Helv. Chemica Acta (1981) 237, 2405-2417.

Becher et al. "Synthesis of Astaxanthin from beta-Ionone. I. A Route to the Enantiomeric C15-Wittig Salts by Chemical and Microbial Resolution of (+-)-3-Acetoxy-4-oxo-beta-ionone" Helv. Chem. Acta, 64, 238, (1981) 2419-2435.

Carreno et al. "Beta-Hydroxysulfoxides as Chiral Cyclic Ketone Equivalents: Enantioselective Synthesis of Polysubstituted Cyclohexanones, Cyclohexenones and Cyclohexenediones" Chem. Commun. (2002) 3052-3053.

Mayer et al. "Synthesis of Optically Active Natural Carotenoids and Structurally Related Compounds IV. Synthesis of (3R, 3'R, 6'R)-Lutein" Helv. Chim. Acta, 63, 153, (1980) 1451-1455.

Kienzle et al. "Synthesis of Optically Active Natural Carotenoids and Structurally Related Compounds II. Synthesis of (3S, 3'S)-Astaxanthin" Helv. Chim. Acta, 61, 248, (1978) 2609-2615.

Yamaura et al. "Purification and Some Properties of Succinic Semialdehyde Dehydrogenase from Barley Seeds" Agric. Biol. Chem., 52(11), 2929-2930, (1988).

International Search Report (ISR) mailed Oct. 30, 2006, for PCT/US2006/016487 to Lockwood et al. filed May 1, 2006.

Written Opinion (WO) mailed Aug. 16, 2006, for PCT/US2005/035599 to Lockwood et al. filed Oct. 3, 2005.

Markham et al. "Carotenoids of Higher Plants I, The Structures of Lycoxanthin and Lycophyll." Phytochemistry (1968), vol. 7, 839-844.

Braun et al. "Purification of Synthetic all-E Lycophyll (psi,psi-carotene-16,16'-diol)." Jour. of Chromatography B (2006), 834(1-2), 208-212.

Haugan et al. "Total Synthesis of C31-Methyl Ketone Apocarotenoids 3. On the Structure of Hopkinsiaxanthin: First Total Synthesis of (all-E)-(3S)-and (9Z)-(3S)-7'-Apohopkinsiaxanthin." Acta Chemica Scandinavica (1997), 51, 1201-1216.

Jackson et al. "Efficient Total Synthesis of Lycophyll (psi,psi-carotene-16,16'-diol)." Organic Process Research & Development (2005), 9, 830-836.

Liotta et al. "Pyridinium Dichromate-Induced 1,3-Oxidative Rearrangements of Enynols." Tetrahedron Letters (1987), 28, 10, 1069-1072.

Srikrishna et al. J. Chem. Soc. Perkin Trans. 1; EN; 11, (1996), 1305-1312.

Takahashi et al. Agric. Biol. Chem.; EN; 51, 4, (1987), 1143-1148.

Von Arx et al. "Unprecedented Selectivity Behavior in the Hydrogenation of an alpha,beta-unsaturated Ketone: Hydrogenation of Ketoisophorone Over Alumina-Supported Pt and Pd." J. of Molecular Catalysis A: Chemical 148 (1999), 275-283.

* cited by examiner 2A (Beta-carotene)

2B (Lutein)

2C Zeaxanthin 2D (Canthaxanthin)

2E (Astaxanthin)

METHODS FOR THE SYNTHESIS OF ASTAXANTHIN

PRIORITY CLAIM

This application claims priority to U.S. Provisional Patent Application No. 60/615,032 entitled "Methods for Synthesis of Carotenoids, Including Analogs, Derivatives, and Synthetic and Biological Intermediates" filed on Oct. 1, 2004; U.S. Provisional Patent Application No. 60/675,957 entitled "Methods for Synthesis of Carotenoids, Including Analogs, Derivatives, and Synthetic and Biological Intermediates" filed on Apr. 29, 2005; U.S. Provisional Patent Application No. 60/691,518 entitled "Methods for Synthesis of Carotenoids, Including Analogs, Derivatives, and Synthetic and Biological Intermediates" filed on Jun. 17, 2005; U.S. Provisional Patent Application No. 60/692,682 entitled "Methods for Synthesis of Carotenoids, Including Analogs, Derivatives, and Synthetic and Biological Intermediates" filed on Jun. 21, 2005; U.S. Provisional Patent Application No. 60/699,653 entitled "Methods for Synthesis of Carotenoids, Including Analogs, Derivatives, and Synthetic and Biological Intermediates" filed on Jul. 15, 2005; U.S. Provisional Patent Application No. 60/702,380 entitled "Methods for Synthesis of Carotenoids, Including Analogs, Derivatives, and Synthetic and Biological Intermediates" filed on Jul. 26, 2005; and U.S. Provisional Patent Application No. 60/712,350 entitled "Methods for Synthesis of Carotenoids, Including Analogs, Derivatives, and Synthetic and Biological Intermediates" filed on Aug. 30, 2005.

BACKGROUND OF THE INVENTION

1. Field of the Invention

The invention generally relates to the fields of medicinal and synthetic chemistry. More specifically, the invention relates to the synthesis and use of carotenoids, including analogs, derivatives, and intermediates.

2. Description of the Relevant Art

Carotenoids are a group of natural pigments produced principally by plants, yeast, and microalgae. The family of related compounds now numbers greater than 700 described members, exclusive of Z and E isomers. At least fifty (50) carotenoids have been found in human sera or tissues. Humans and other animals cannot synthesize carotenoids de novo and must obtain them from their diet. All carotenoids share common chemical features, such as a polyisoprenoid structure, a long polyene chain forming the chromophore, and near symmetry around the central double bond. Tail-to-tail linkage of two $C_{20}$ geranyl diphosphate molecules produces the parent $C_{40}$ carbon skeleton. Carotenoids without oxygenated functional groups are called "carotenes", reflecting their hydrocarbon nature; oxygenated carotenes are known as "xanthophylls." Cyclization at one or both ends of the molecule yields 7 identified end groups (illustrative structures shown in FIG. 1).

Documented carotenoid functions in nature include light-harvesting, photoprotection, and protective and sex-related coloration in microscopic organisms, mammals, and birds, respectively. A relatively recent observation has been the protective role of carotenoids against age-related diseases in humans as part of a complex antioxidant network within cells. This role is dictated by the close relationship between the physicochemical properties of individual carotenoids and their in vivo functions in organisms. The long system of alternating double and single bonds in the central part of the molecule (delocalizing the π-orbital electrons over the entire length of the polyene chain) confers the distinctive molecular shape, chemical reactivity, and light-absorbing properties of carotenoids. Additionally, isomerism around C=C double bonds yields distinctly different molecular structures that may be isolated as separate compounds (known as Z ("cis") and E ("trans"), or geometric, isomers). Of the more than 700 described carotenoids, an even greater number of the theoretically possible mono-Z and poly-Z isomers are sometimes encountered in nature. The presence of a Z double bond creates greater steric hindrance between nearby hydrogen atoms and/or methyl groups, so that Z isomers are generally less stable thermodynamically, and more chemically reactive, than the corresponding all-E form. The all-E configuration is an extended, linear, and rigid molecule. Z-isomers are, by contrast, not simple, linear molecules (the so-called "bent-chain" isomers). The presence of any Z in the polyene chain creates a bent-chain molecule. The tendency of Z-isomers to crystallize or aggregate is much less than all-E, and Z isomers may sometimes be more readily solubilized, absorbed, and transported in vivo than their all-E counterparts. This has important implications for enteral (e.g., oral) and parenteral (e.g., intravenous, intra-arterial, intramuscular, intraperitoneal, intracoronary, and subcutaneous) dosing in mammals.

Carotenoids with chiral centers may exist either as the R (rectus) or S (sinister) configurations. As an example, astaxanthin (with 2 chiral centers at the 3 and 3' carbons) may exist as 3 possible stereoisomers: 3S, 3'S; 3R, 3'S and 3S, 3'R (identical meso forms); or 3R, 3'R. The relative proportions of each of the stereoisomers may vary by natural source. For example, *Haematococcus pluvialis* microalgal meal is 99% 3S, 3'S astaxanthin, and is likely the predominant human evolutionary source of astaxanthin. Krill (3R, 3'R) and yeast sources yield different stereoisomer compositions than the microalgal source. Synthetic astaxanthin, produced by large manufacturers such as Hoffmann-LaRoche AG, Buckton Scott (USA), or BASF AG, are provided as defined geometric isomer mixtures of a 1:2:1 stereoisomer mixture (3S, 3'S; 3R, 3'S, (meso); 3R, 3'R) of non-esterified, free astaxanthin. Natural source astaxanthin from salmonid fish is predominantly a single stereoisomer (3S, 3'S), but does contain a mixture of geometric isomers. Astaxanthin from the natural source *Haematococcus pluvialis* may contain nearly 50% Z isomers. As stated above, the Z conformational change may lead to a higher steric interference between the two parts of the carotenoid molecule, rendering it less stable, more reactive, and more susceptible to reactivity at low oxygen tensions. In such a situation, in relation to the all-E form, the Z forms: (1) may be degraded first; (2) may better suppress the attack of cells by reactive oxygen species such as superoxide anion; and (3) may preferentially slow the formation of radicals. Overall, the Z forms may initially be thermodynamically favored to protect the lipophilic portions of the cell and the cell membrane from destruction. It is important to note, however, that the all-E form of astaxanthin, unlike β-carotene, retains significant oral bioavailability as well as antioxidant capacity in the form of its dihydroxy- and diketo-substitutions on the β-ionone rings, and has been demonstrated to have increased efficacy over β-carotene in most studies. The all-E form of astaxanthin has also been postulated to have the most membrane-stabilizing effect on cells in vivo. Therefore, it is likely that the all-E form of astaxanthin in natural and synthetic mixtures of stereoisomers is also extremely important in antioxidant mechanisms, and may be the form most suitable for particular pharmaceutical preparations.

The antioxidant mechanism(s) of carotenoids, (e.g., astaxanthin), includes singlet oxygen quenching, direct radical scavenging, and lipid peroxidation chain-breaking. The polyene chain of the carotenoid absorbs the excited energy of singlet oxygen, effectively stabilizing the energy transfer by delocalization along the chain, and dissipates the energy to the local environment as heat. Transfer of energy from triplet-state chlorophyll (in plants) or other porphyrins and proto-porphyrins (in mammals) to carotenoids occurs much more readily than the alternative energy transfer to oxygen to form the highly reactive and destructive singlet oxygen ($^1O_2$). Carotenoids may also accept the excitation energy from singlet oxygen if any should be formed in situ, and again dissipate the energy as heat to the local environment. This singlet oxygen quenching ability has significant implications in cardiac ischemia, macular degeneration, porphyria, and other disease states in which production of singlet oxygen has damaging effects. In the physical quenching mechanism, the carotenoid molecule may be regenerated (most frequently), or be lost. Carotenoids are also excellent chain-breaking antioxidants, a mechanism important in inhibiting the peroxidation of lipids. Astaxanthin can donate a hydrogen (H) to the unstable polyunsaturated fatty acid (PUFA) radical, stopping the chain reaction. Peroxyl radicals may also, by addition to the polyene chain of carotenoids, be the proximate cause for lipid peroxide chain termination. The appropriate dose of astaxanthin has been shown to completely suppress the peroxyl radical chain reaction in liposome systems. Astaxanthin shares with vitamin E this dual antioxidant defense system of singlet oxygen quenching and direct radical scavenging, and in most instances (and particularly at low oxygen tension in vivo) is superior to vitamin E as a radical scavenger and physical quencher of singlet oxygen.

Carotenoids, (e.g., astaxanthin), are potent direct radical scavengers and singlet oxygen quenchers and possess all the desirable qualities of such therapeutic agents for inhibition or amelioration of ischemia-reperfusion injury. Synthesis of novel carotenoid derivatives with "soft-drug" properties (i.e. active as antioxidants in the derivatized form), with physiologically relevant, cleavable linkages to pro-moieties, can generate significant levels of free carotenoids in both plasma and solid organs. In the case of non-esterified, free astaxanthin, this is a particularly useful embodiment (characteristics specific to non-esterified, free astaxanthin below):

Lipid soluble in natural form; may be modified to become more water soluble;
Molecular weight of 597 Daltons (size <600 daltons (Da) readily crosses the blood brain barrier, or BBB);
Long polyene chain characteristic of carotenoids effective in singlet oxygen quenching and lipid peroxidation chain breaking; and
No pro-vitamin A activity in mammals (eliminating concerns of hypervitaminosis A and retinoid toxicity in humans).

The administration of antioxidants which are potent singlet oxygen quenchers and direct radical scavengers, particularly of superoxide anion, should limit hepatic fibrosis and the progression to cirrhosis by affecting the activation of hepatic stellate cells early in the fibrogenetic pathway. Reduction in the level of "Reactive Oxygen Species" (ROS) by the administration of a potent antioxidant can therefore be crucial in the prevention of the activation of both "hepatic stellate cells" (HSC) and Kupffer cells. This protective antioxidant effect appears to be spread across the range of potential therapeutic antioxidants, including water-soluble (e.g., vitamin C, glutathione, resveratrol) and lipophilic (e.g., vitamin E, β-carotene, astaxanthin) agents. Therefore, a co-antioxidant derivative strategy in which water-soluble and lipophilic agents are combined synthetically is a particularly useful embodiment. Examples of uses of carotenoid derivatives and analogs are illustrated in U.S. patent application Ser. No. 10/793,671 filed on Mar. 4, 2004, entitled "CAROTENOID ETHER ANALOGS OR DERIVATIVES FOR THE INHIBITION AND AMELIORATION OF DISEASE" to Lockwood et al. published on Jan. 13, 2005, as Publication No. US-2005-0009758 and PCT International Application Number PCT/US2003/023706 filed on Jul. 29, 2003, entitled "STRUCTURAL CAROTENOID ANALOGS FOR THE INHIBITION AND AMELIORATION OF DISEASE" to Lockwood et al. (International Publication Number WO 2004/011423 A2, published on Feb. 5, 2004) both of which are incorporated by reference as if fully set forth herein.

Vitamin E is generally considered the reference antioxidant. When compared with vitamin E, carotenoids are more efficient in quenching singlet oxygen in homogeneous organic solvents and in liposome systems. They are better chain-breaking antioxidants as well in liposomal systems. They have demonstrated increased efficacy and potency in vivo. They are particularly effective at low oxygen tension, and in low concentration, making them extremely effective agents in disease conditions in which ischemia is an important part of the tissue injury and pathology. These carotenoids also have a natural tropism for the heart and liver after oral administration. Therefore, therapeutic administration of carotenoids should provide a greater benefit in limiting fibrosis than vitamin E.

Problems related to the use of some carotenoids and structural carotenoid analogs or derivatives include: (1) the complex isomeric mixtures, including non-carotenoid contaminants, provided in natural and synthetic sources leading to costly increases in safety and efficacy tests required by such agencies as the FDA; (2) limited bioavailability upon administration to a subject; and (3) the differential induction of cytochrome P450 enzymes (this family of enzymes exhibits species-specific differences which must be taken into account when extrapolating animal work to human studies). Selection of the appropriate analog or derivative and isomer composition for a particular application increases the utility of carotenoid analogs or derivatives for the uses defined herein.

Synthesis of an appropriate analog or derivative and isomer composition requires a supply of starting materials (e.g., carotenoids, carotenoid synthetic intermediates). Any new synthetic route which is more efficient to a carotenoid analog or derivative and/or synthetic intermediate would be beneficial. More efficient synthetic routes would provide a more stable source of starting materials (e.g., carotenoids) which may be difficult or expensive to extract from natural sources. Synthetic routes to natural products may facilitate the synthesis of analogs and derivatives of the natural products.

SUMMARY

A synthetic route to a carotenoid, carotenoid analog or derivative and/or synthetic intermediate is presented. In some embodiments, methods and reactions described herein may be used to synthesize naturally-occurring carotenoids. Naturally-occurring carotenoids may include astaxanthin as well as other carotenoids including, but not limited to, zeaxanthin, carotenediol, nostoxanthin, crustaxanthin, canthaxanthin, isozeaxanthin, hydroxycanthaxanthin, tetrahydroxy-carotene-dione, lutein, lycophyll, and lycopene.

In one embodiment, a method of making astaxanthin includes: contacting a diketone compound having the structure

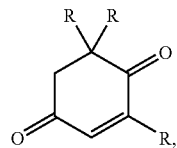

where each R is independently alkyl, phenyl, or aryl, with a chiral catalyst, to stereoselectively reduce the ketone to give a hydroxy product having the general structure:

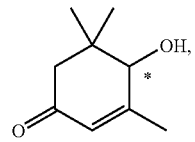

wherein R is alkyl, phenyl, or aryl and wherein the "*" represents a chiral carbon atom that exists, predominantly, as a single stereoisomer; and contacting the hydroxy product with a reducing agent to form the dihydroxy compound

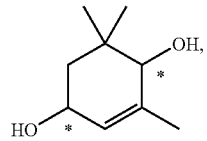

wherein the "*" represents chiral carbon atoms that exist, predominantly, as a single stereoisomer.

In some embodiments, each R is methyl. The chiral catalyst, in some embodiments, includes a metal and an optically active chiral ligand. The metal may be any transition metal. In some embodiments, the metal is ruthenium. A chiral catalyst may include ruthenium and an optically active chiral ligand. In some embodiments, an optically active chiral ligand is an optically active amine. Examples of optically active amines include: amino acids, $H_2N$-CHPh-CHPh-OH, $H_2N$-CHMe-CHPh-OH, MeHN-CHMe-CHPh-OH, $H_2N$-CHPh-CHPh-OH, $H_2N$-CHMe-CHPh-OH, MeHN-CHMe-CHPh-OH.

The reducing agent may include any reducing agent capable of reducing a ketone to a hydroxyl functional group. In some embodiments the reducing agent is borohydride reducing agent. The borohydride reducing agent may be a lithium trialkyl borohydride reducing agent. In alternate embodiments, the reducing agent may be an aluminum hydride reducing agent.

Use of a chiral catalyst to reduce the diketone starting material may lead to optically active stereoisomers that include the hydroxy ketone compound

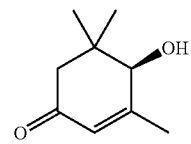

which may be further transformed into the optically active dihydroxy compound

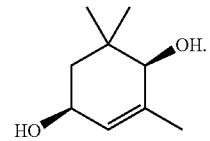

In an embodiment, the dihydroxy compound may be converted into protected ketone having the structure

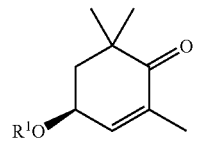

where $R^1$ is alkyl, phenyl, aryl or silyl.

The protected ketone may be converted into the unsaturated ketone having the structure:

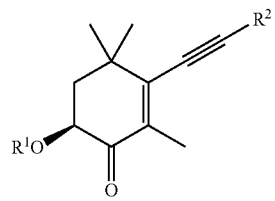

where $R^1$ is alkyl, phenyl, aryl or silyl, and $R^2$ is

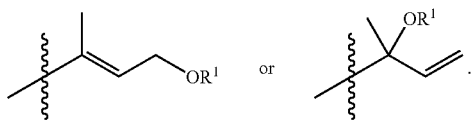

Formation of the unsaturated ketone may be accomplished by reacting the protected ketone with an acetylinic compound having the structure:

$M^+$—C≡C—$R^2$, where M is a metal and $R^2$ is

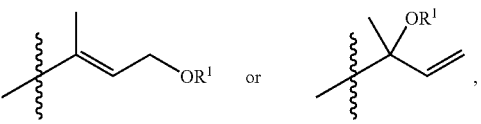

to give an addition product having the structure:

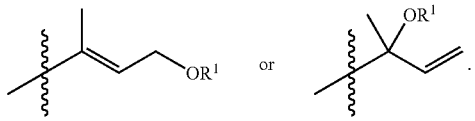

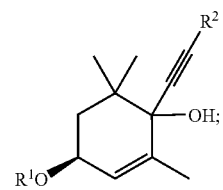

and reacting the addition product with an oxidant to give the unsaturated ketone. The unsaturared ketone may then be converted into an aldehyde reactive compound having the structure:

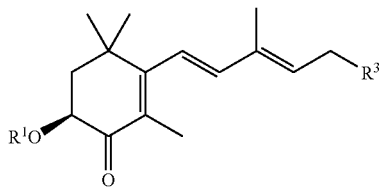

where $R^1$ is is alkyl, phenyl, aryl or silyl; and $R^3$ is $PR^4_3$, $P(O)R^4_3$, $SO_2R^4$, or $M^+$ where $R^4$ is alkyl, phenyl, or aryl and M is Li, Na, or MgBr. The aldehyde reactive compound may then be reacted with the dialdehyde having the structure

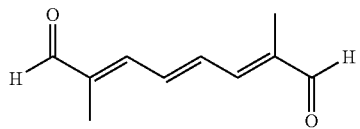

to form astaxanthin. All stereoisomers of astaxanthin may be selectively formed using this method including the 3S, 3'S stereoisomer and the 3R, 3'R stereoisomer.

BRIEF DESCRIPTION OF THE DRAWINGS

The above brief description as well as further objects, features and advantages of the methods and apparatus of the present invention will be more fully appreciated by reference to the following detailed description of presently preferred but nonetheless illustrative embodiments in accordance with the present invention when taken in conjunction with the accompanying drawings.

Figure 1:
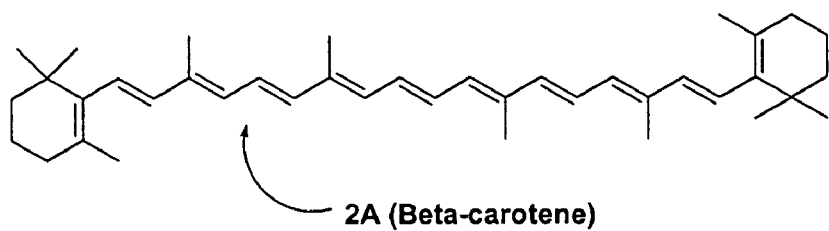
FIG. 1 depicts a graphic representation of several examples of "parent" carotenoid structures as found in nature.
Figure 1:
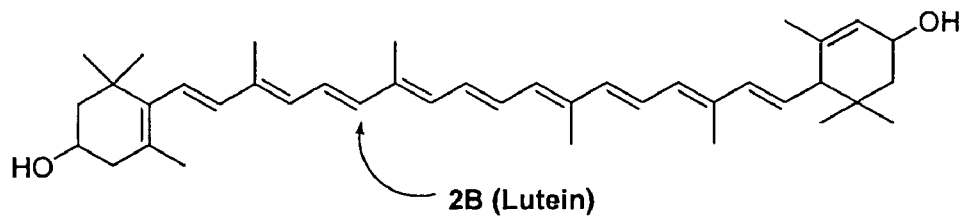
Figure 1:
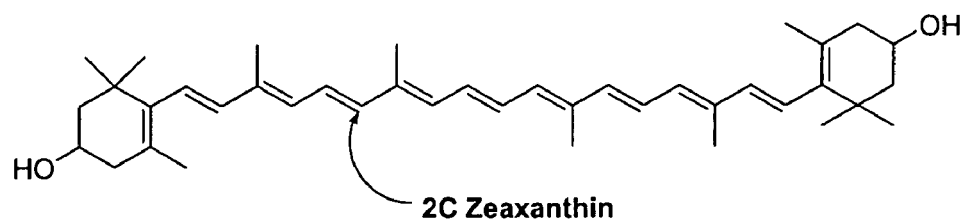
Figure 1:
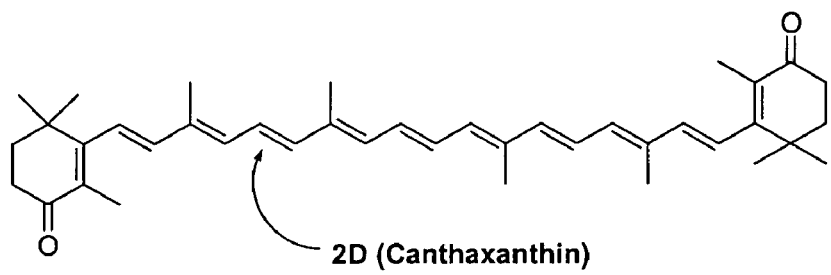
Figure 1:
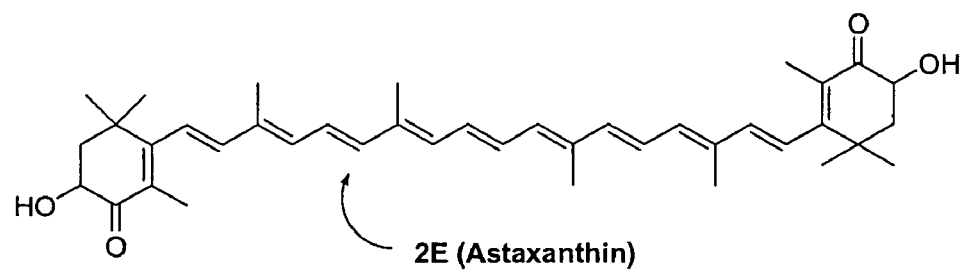

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

Compounds described herein embrace both racemic and optically active compounds. Chemical structures depicted herein which do not designate specific stereochemistry are intended to embrace all possible stereochemistries.

It will be appreciated by those skilled in the art that compounds having one or more chiral center(s) may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound. As used herein, the term "single stereoisomer" refers to a compound having one or more chiral center that, while it can exist as two or more stereoisomers, is isolated in greater than about 95% excess of one of the possible stereoisomers. As used herein a compound that has one or more chiral centers is considered to be "optically active" when isolated or used as a single stereoisomer.

The following definitions are used, unless otherwise described. Halo, as used herein refers to fluoro, chloro, bromo, or iodo. "Alkyl," "alkoxy," etc. denote both straight and branched groups; but reference to an individual radical such as "propyl" embraces only the straight chain radical, a branched chain isomer such as "isopropyl" being specifically referred to.

Specific and preferred values listed below for radicals, substituents, and ranges, are for illustration only; they do not exclude other defined values or other values within defined ranges for the radicals and substituents. Specifically, "alkyl" includes, but is not limited to: methyl, ethyl, propyl, isopropyl, butyl, iso-butyl, sec-butyl, pentyl, 3-pentyl, hexyl, heptyl, octyl, nonyl, decyl, undecyl, dodecyl, tridecyl, tetradecyl or pentadecyl; "alkenyl" includes but is not limited to vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl; 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, 11-dodecenyl, 1-tridecenyl, 2-tridecenyl, 3-tridecenyl, 4-tridecenyl, 5-tridecenyl, 6-tridecenyl, 7-tridecenyl, 8-tridecenyl, 9-tridecenyl, 10-tridecenyl, 11-tridecenyl, 12-tridecenyl, 1-tetradecenyl, 2-tetradecenyl, 3-tetradecenyl, 4-tetradecenyl, 5-tetradecenyl, 6-tetradecenyl, 7-tetradecenyl, 8-tetradecenyl, 9-tetradecenyl, 10-tetradecenyl, 11-tetradecenyl, 12-tetradecenyl, 13-tetradecenyl, 1-pentadecenyl, 2-pentadecenyl, 3-pentadecenyl, 4-pentadecenyl, 5-pentadecenyl, 6-pentadecenyl, 7-pentadecenyl, 8-pentadecenyl, 9-pentadecenyl, 10-pentadecenyl, 1-pentadecenyl, 12-pentadecenyl, 13-pentadecenyl, or 14-pentadecenyl. "Alkoxy" includes but is not limited to methoxy, ethoxy, propoxy, isopropoxy, butoxy, iso-butoxy, sec-butoxy, pentoxy, 3-pentoxy, hexoxy, heptyloxy, octyloxy, nonyloxy, decyloxy, undecyloxy, dodecyloxy, tridecyloxy, tetradecyloxy, or pentadecyloxy. "Cycloalkyl" includes, but is not limited to cyclopropyl, cyclobutyl, cyclopentyl, cyclohexyl, cycloheptyl, or cyclooctyl. "Aryl" includes but is not limited to phenyl, substituted benzene, naphthyl, substituted naphthyl, anthracene, or substituted anthracene.

The synthesis of certain naturally-occurring carotenoids is presented herein. In some embodiments, methods and reactions described herein may be used to synthesize naturally-occurring carotenoids. Naturally-occurring carotenoids may include astaxanthin as well as other carotenoids. Some of the other carotenoids may include carotenoids such as, for example, zeaxanthin, carotenediol, nostoxanthin, crustaxanthin, canthaxanthin, isozeaxanthin, hydroxycanthaxanthin, tetrahydroxy-carotene-dione, lutein, and lycopene. Carotenoids having the general formula (I) below may be synthesized using the methods described herein.

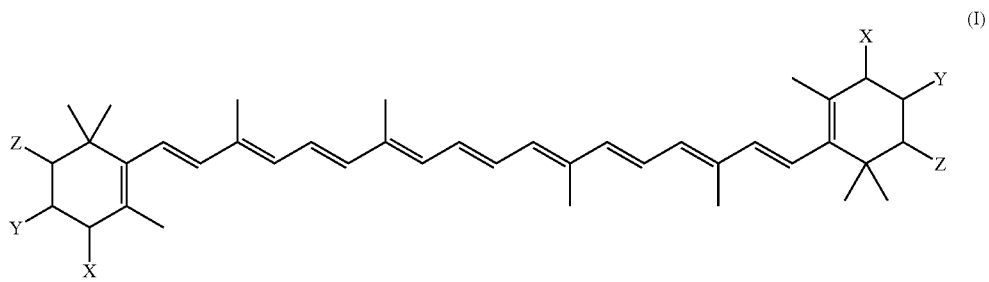

(I)

X, Y, and Z may be independently H, —OH or =O.

The compound of formula I embraces "racemic" (e.g. statistical mixture of stereoisomers), optically inactive (e.g. meso forms) and optically active (e.g. enantiomeric) compounds. In some embodiments, carotenoids may be isolated using methods described herein with an enantiomeric excess of greater than 99%. In some embodiments, carotenoids may be isolated using methods described herein with an enantiomeric excess of greater than 95%. In some embodiments, carotenoids may be isolated using methods described herein with an enantiomeric excess of greater than 90%.

In some embodiments, Z is H, Y is —OH, and X is =O such that the carotenoid has the general structure depicted below. The carotenoid below is commonly referred to as astaxanthin.

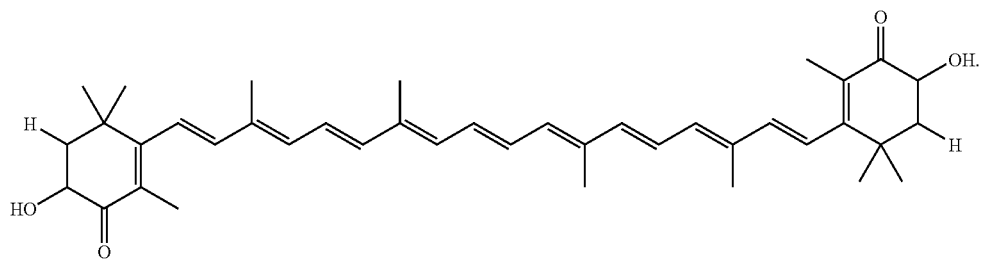

In some embodiments, Z is H, Y is OH, and X is OH such that the carotenoid has the general structure depicted below. The carotenoid below is commonly referred to as crustaxanthin.

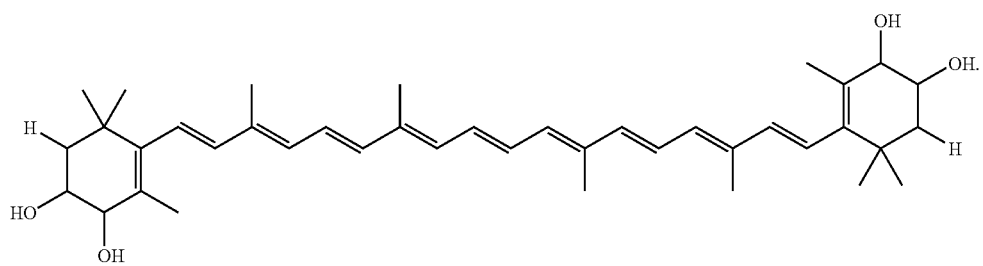

In some embodiments, Z is H, Y is H, and X is =O such that the carotenoid has the general structure depicted below. The carotenoid below is commonly referred to as canthaxanthin.

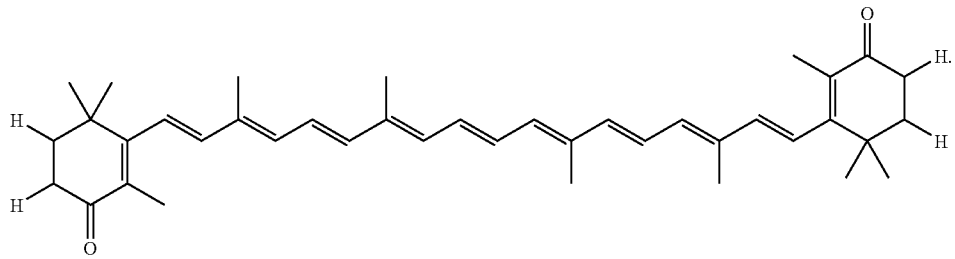

In some embodiments, Z is H, Y is H, and X is —OH such that the carotenoid has the general structure depicted below. The carotenoid below is commonly referred to as isozeaxanthin.

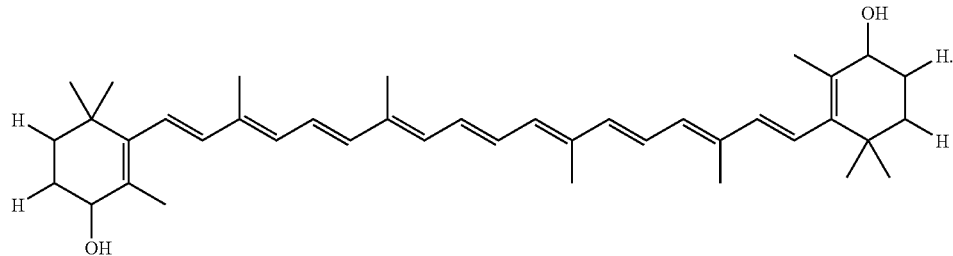

In some embodiments, Z is OH, Y is H, and X is ═O such that the carotenoid has the general structure depicted below. The carotenoid below is commonly referred to as hydroxycanthaxanthin.

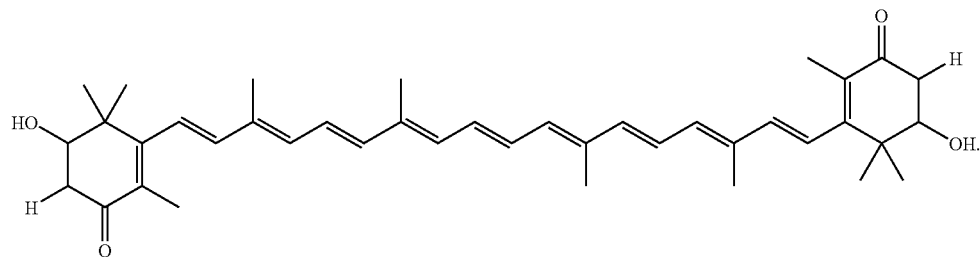

In some embodiments, Z and Y are —OH and X is ═O such that the carotenoid has the general structure depicted below. The carotenoid below is commonly referred to as tetrahydroxy-carotene-dione

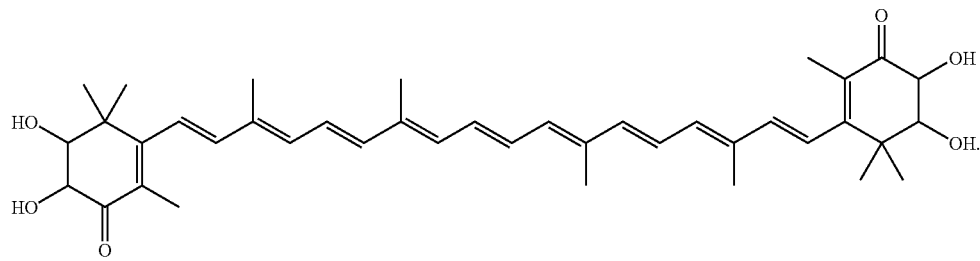

In an embodiment, carotenoids may be synthesized using the general process shown in Scheme I below.

SCHEME I

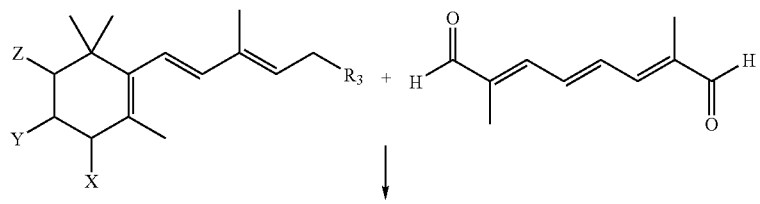

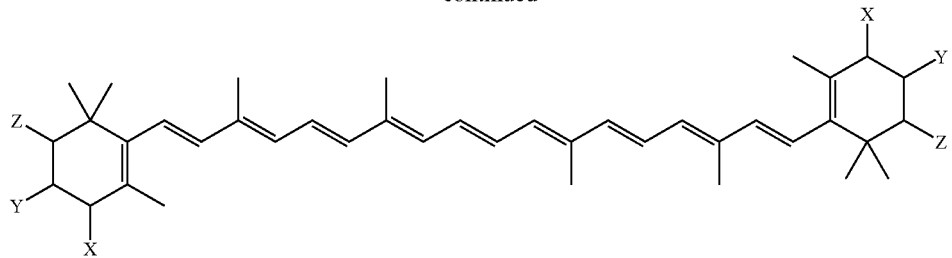

X, Y, and Z may be independently H, —OH or =O. $R^3$ may be $PR^4_3$, $SO_2R^4$, or $M^{30}$. $R^4$ may be alkyl, phenyl, or aryl. M is Li, Na, or MgBr. Coupling of two "head units" with the $C_{10}$-aldehyde yields a carotenoid. Coupling may be accomplished using a Wittig coupling ($R^3$ is $PR^4_3$), sulphone coupling ($R^3$ is $SO_2R^4$), or condensation reaction ($R^3$ is $M^+$). The $C_{10}$ aldehyde is commercially available. Described herein are various methods of synthesizing the appropriate headpiece. The following U.S. patents, all of which are incorporated herein by reference, describe the synthesis of various carotene and carotenoid synthesis intermediates: U.S. Pat. No. 4,245,109 to Mayer et al., U.S. Pat. No. 4,283,559 to Broger et al, U.S. Pat. No. 4,585,885 to Bernhard et al., U.S. Pat. No. 4,952,716 to Lukac et al., and U.S. Pat. No. 6,747,177 to Ernst et al.

In one embodiment, a headpiece useful for the synthesis of astaxanthin may be formed using the process depicted in Scheme II.

SCHEME II

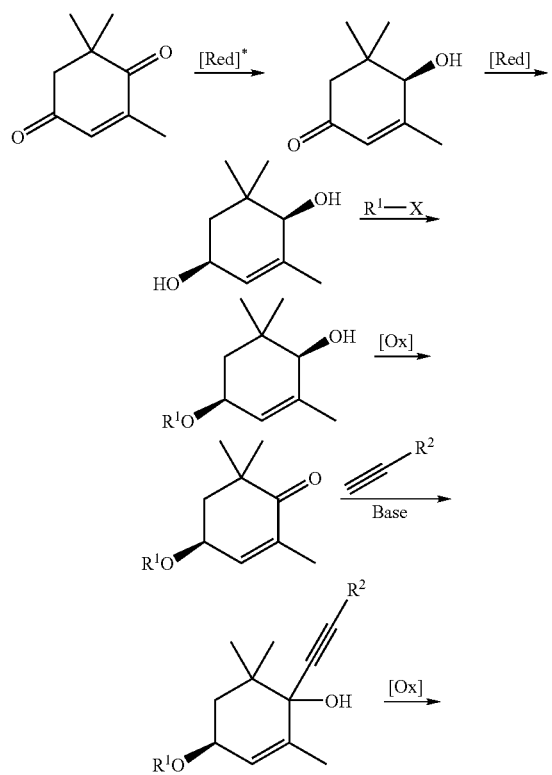

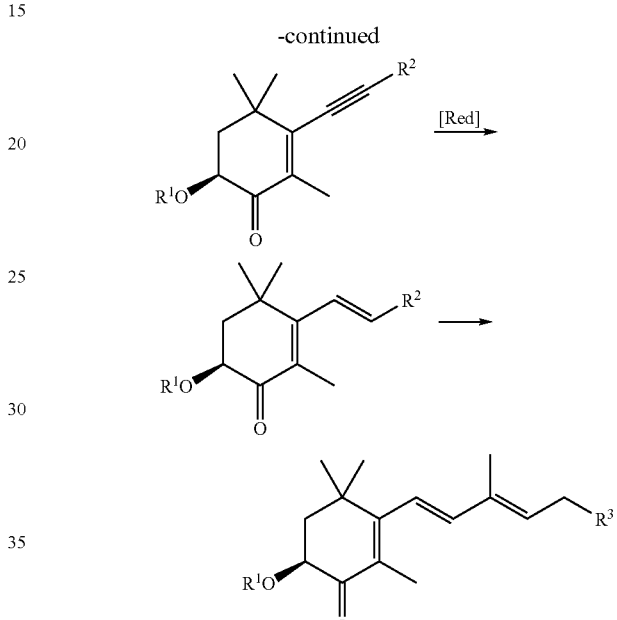

While the compounds shown in Scheme II are generally depicted as single stereoisomers, it should be understood that Scheme II may be used to synthesize the racemic headpiece. An intermediate in the synthesis of astaxanthin is shown below as compound 108A.

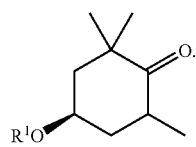

108a $R^1$ may include hydrogen, alkyl, or aryl. $R^3$ may also include any alcohol protecting groups known to one skilled in the art. Protecting groups may include, but are not limited to, silyl protecting groups such as tert-butyldimethylsilane (i.e., TBDMS). In some embodiments, compound 108a may be synthesized from commercially available keto-α-isopherone 109 having a general formula of

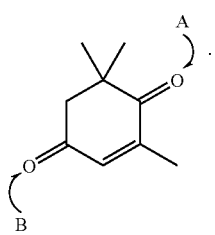

109

Keto-α-isopherone may be selectively reduced. The more sterically hindered ketone may be reduced to an alcohol. The more sterically hindered ketone A may be stereoselectively reduced to an alcohol. In some embodiments, a complexing reagent may be used to react with the less sterically hindered ketone. In so doing this, the complexing agent may protect the less sterically hindered ketone B from reacting with a reagent (e.g., a reducing agent), thereby directing the reagent to react with the more sterically hindered ketone A.

In some embodiments, a complexing agent may also be optically pure or form an optically pure complex with an activating metal, either of which may react with the less sterically hindered ketone B, such that the reduction of more sterically hindered ketone A results in an optically pure product. It should be noted that within the description herein absolute terms or phrases used (e.g., optically pure) are understood to include at least a range typically acceptable to one skilled in the art. In one example, the optically pure product referred to regarding the reduced ketone may be >90% pure. In an example, the optically pure product referred to regarding the reduced ketone may be >95% pure. In an example, the optically pure product referred to regarding the reduced ketone may be >99% pure. In an example, the optically pure product referred to regarding the reduced ketone may be >99.9% pure.

In some embodiments a reduction catalyst may be a chiral catalyst. A "chiral catalyst" as defined herein is a catalyst that includes a single stereoisomer of a chiral molecule. In one embodiment, a chiral catalyst includes a transition metal and an optically active chiral ligand. Transition metals that may be used to form a chiral catalyst for reduction of ketones include Ti, Zr, Hf, V, Nb, Ta, Cr, Mo, W, Mn, Re, Fe, Ru, Os, Co, Rh, Ir, Ni, Pd, Pt, Cu, Ag, and Au. In some embodiments, a ruthenium chiral catalyst may be used to effect a stereoselective reduction of keto-α-isopherone. The ruthenium chiral catalyst may be formed from a mixture of [RuX$_2$(η$^6$-Ar)]$_2$ with an optically active amine, where X represents a halogen (e.g., F, Cl, Br, I) and Ar represents benzene or a substituted benzene (e.g., alkyl substituted benzene). In some embodiments, the optically active amine includes both (S)- and (R)-amino acids, and other optically active amines such as as H$_2$N-CHPh-CHPh-OH, H$_2$N-CHMe-CHPh-OH, MeHN-CHMe-CHPh-OH. Reduction of keto-α-isopherone with a chiral catalyst may yield the optically active hydroxy ketone 116. While hydroxy ketone 116 is depicted in the (R)- form, it should be understood that the (S)- form may be formed by using the opposite optically active compound to form a chiral catalyst. For example, forming a ruthenium catalyst using (1R, 2S)-(−)-norephedrine leads to the (R)-form of the hydroxy ketone depicted below, while forming a ruthenium catalyst using (1S, 2R)-(+)-norephedrine leads to the (S)-form of the hydroxy ketone below. Further details regarding the use of ruthenium catalyst for the reduction of keto-α-isopherone may be found in the paper "Synthesis of (R)- and (S)-hydroxyisophorone by ruthenium-catalyzed asymmetric transfer hydrogenation of ketoisopherone" by Hennig et al., Tetrahedron: Asymmetry, 11 (2000) 1849–1858, which is incorporated herein by reference.

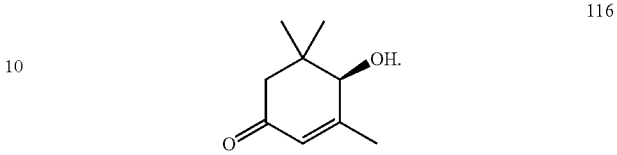

116

Compound 116 may be further reduced. The remaining ketone of compound 116 may be reduced to an alcohol. The resulting alcohol to which the remaining ketone of compound 116 has been reduced may be optically pure. Any type of reducing agent suitable for reducing a ketone to a hydroxy group may be used. The reducing agent may be a chiral reducing agent or an achiral reducing agent. The stereoselectivity of the reduction at hydroxyl (D) is controlled, at least in part, by the stereochemistry of the hydroxy group (C) as depicted in 118.

In some embodiments, a borohydride reducing agent may be used to reduce the ketone group of compound 116. In an embodiment, a hindered borohydride reducing agent may be used to assist in achieving an enantiomerically pure reduction of the remaining ketone of compound 116. In an embodiment, the hindered borohydride reducing agent is a lithium trialkyl borohydride. Examples of lithium trialkyl borohydrides include, but are not limited to, lithium tri-sec-butylborohydride and lithium trisiamylborohydride. Reduction of the remaining ketone of 116 results in compound 118 having a general formula of

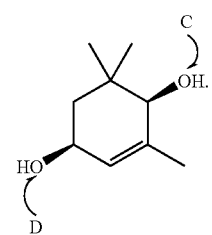

118

Other types of hindered reducing agents may be used such as hindered aluminum hydride reducing agents may also be used to reduce ketone 116.

Alcohol D of compound 118 may be selectively protected using any number of alcohol protecting groups known to one skilled in the art to produce compound 120 having the general structure of

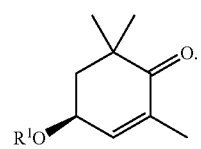

120 where R$^1$ is alkyl, phenyl, aryl or silyl. In some embodiments, protecting groups may include sterically hindered protecting groups. Examples of sterically hindered protecting groups include hindered silyl protecting groups. Silyl protecting groups may include, but are not limited to, trimethylsilane, triethylsilane, triisopropylsilane, tert-butyl dimethyl silane (i.e., TBDMS), and diphenyl-t-butylsilane. If $R^1$ is a TBDMS group, the resulting protected compound has the structure of 120a

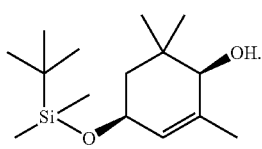

120a

Upon protecting less sterically hindered alcohol D, more sterically hindered alcohol C may be oxidized to a ketone. Oxidation of hydroxyl C may be accomplished using a variety of oxidizing reagents such as chromium oxidants, manganese oxidants, and selenium oxidants. In one embodiment, the oxidizing agent may include, for example, pyridinium dichromate (PDC). Oxidation of hydroxyl group C leads to optically active ketone 108a, where $R^1$ is alkyl, phenyl, aryl or silyl.

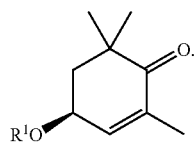

108a

In some embodiments, $R^1$ may include a protecting group (e.g., TBDMS) such that 108a has a general structure of 108b

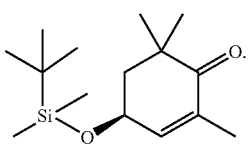

108b

In some embodiments, an enantiomeric excess of compound 108a may be determined. Enantiomeric excess may be determined by first removing any protecting groups, then measuring the optical purity using circular dichroism (CD) spectroscopy.

As depicted in Scheme II protected hydroxy ketone 108 may be used to synthesise astaxanthin, as well as other carotenoid derivatives, as described herein. In an embodiment, ketone 108 is reacted with a nucleophilic acetylenic derivative to form an addition product 112 depicted below

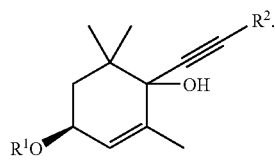

112 where $R^1$ is alkyl, phenyl, aryl or silyl. Compound 112 may be formed by reacting ketone 108 with a nucleophile. The nucleophile may selectively react with the carbonyl group of compound 108, transforming the carbonyl to an alcohol, as well as forming a new substituent at the 2 position of the carbonyl. In a specific embodiment compound 108 may be alkynylated. An alkyne may be reacted with compound 108 in an inert solvent (e.g., tetrahydrofuran ("THF")). The reaction is preferably carried out at low temperatures. Alkynes may include compounds having the general formula H—C≡C—$R^2$ where $R^2$ includes:

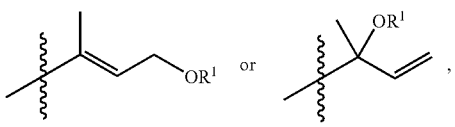

and where $R^1$ is alkyl, phenyl, aryl or silyl. In some embodiments, $R^2$ may include other substituents known to one skilled in the art (e.g., H, silane substituents, alkynes, alkenes, alkyls, aryl substituents, heteroaryl substituents).

Addition of alkyne H—C≡C—$R^2$ to ketone may be accomplished by forming a metal anion of the acetylene, to form the reactive nucleophilic acetylenic compound $M^{+-}$C≡C—$R^2$, where $M^+$ may be, but is not limited to, Li, Na, MgBr, Cd, or Zn. A lithium salt of alkyne H—C≡C—$R^2$ may be formed by reacting the alkyne with, for example, BuLi. Other metal salts of alkynes may be made using methods known to one of ordinary skill in the art. The nucleophilic acetylenic compound $M^{+-}$C≡C—$R^2$ may be reacted with ketone 108 to form a coupling product 112 as depicted below.

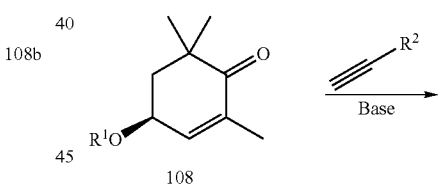

108

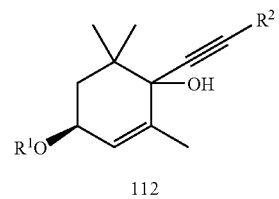

112

$R^2$ may include:

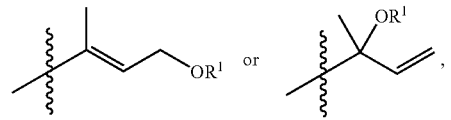

and where $R^1$ may be alkyl, phenyl, aryl or silyl.

Compound 112 may be subjected to rearrangement conditions and oxidized to be converted into unsaturated ketone 114, as depicted below.

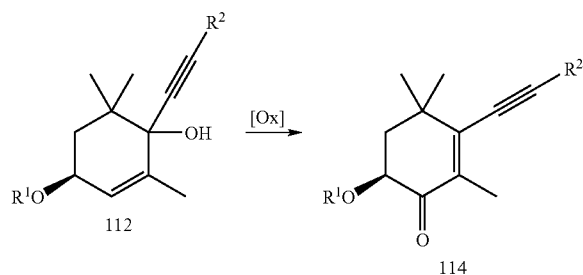

R² may include:

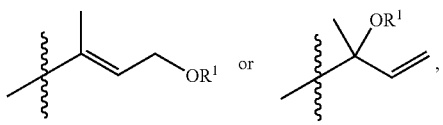

and where R¹ may be alkyl, phenyl, aryl or silyl. Unsaturated ketone 114 may be formed by a two step process or in a novel one step rearrangement oxidation. In one embodiment, compound 112 is subjected to rearrangement conditions (e.g., treatment with aqueous acid) to effect rearrangement of the alcohol to an allylic alcohol (not shown). Subsequent oxidation of the allylic alcohol leads to the unsaturated ketone 114. This two step procedure reduces the efficiency of the process.

In an alternate embodiment, treatment of compound 112 with an oxidant affords the unsaturated ketone 114. This ketone is formed by simultaneous rearrangement and oxidation of the alcohol. The oxidizing agent used in a one-step process may include, for example, chromium oxidant (e.g., pyridinium dichlorochromate (PDC)), selenium oxidant, or manganese oxidant.

Unsaturated ketone 114 may be reduced to olefin 104 as depicted below.

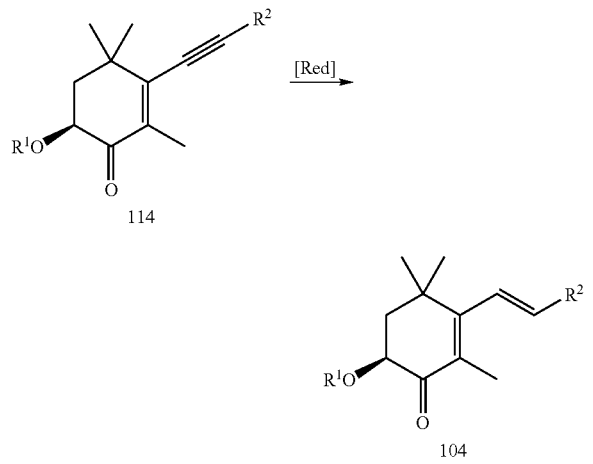

Compound 114 may be used to synthesize compound 104. Treatment of compound 114 with an appropriate reducing agent may reduce the alkyne substituent to give an E-olefin as depicted above. Reducing metal reductions are particularly suited for forming E-olefins from alkynes. Reducing metal reductions may be accomplished using reagents such as Li/NH$_3$, Na/NH$_3$ and Zn/acid. In some embodiments, zinc and an acid may be used to reduce the alkyne to an alkene. The acid may include, for example, glacial acetic acid, ammonium acetate and/or ammonium chloride. The reduction yields the E-isomer predominantly. In some embodiments, one or more protecting groups (e.g., alcohol protecting groups (R¹)) may be removed before partially reducing the alkyne to an alkene.

Upon formation of conjugated alkene 104, the intermediate may be converted into compound 102 having a functional group capable of reacting with an aldehyde to form a double bond.

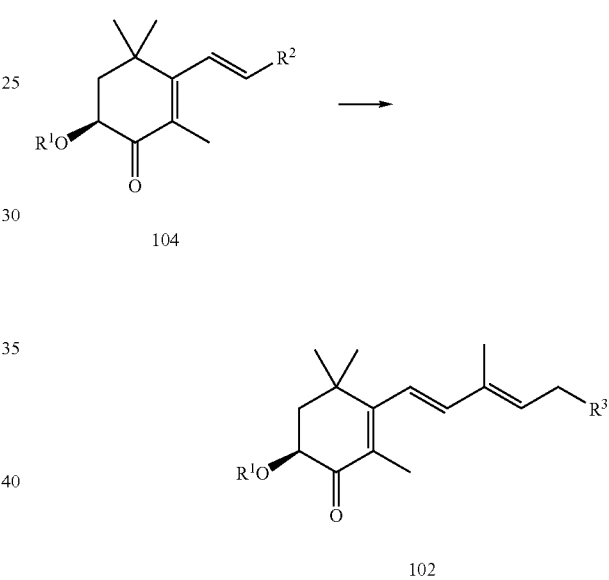

Examples of functionalities that may be reacted with an aldehyde include PR⁴$_3$, SO$_2$R⁴, or M⁺ where R⁴ is alkyl, phenyl, or aryl and M is Li, Na, or MgBr. Coupling of two "head units" with a C$_{10}$—aldehyde yields a carotenoid. Coupling may be accomplished using a Wittig coupling (R³ is PR⁴$_3$), sulphone coupling (R³ is SO$_2$R⁴), or condensation reaction (R³ is M⁺). A phosphonium salt may be synthesized from compound 104. Phosphines and acid may be used to synthesize the phosphonium salt. Phosphines may have the general structure —PR⁵$_3$ or —CH$_2$—P(=O)(OR⁵)$_2$ where R⁵ is alkyl, phenyl, or aryl. Acids may include any of a number of acids known to one skilled in the art. One example of an acid which may be used is hydrogen bromide ("HBr").

Compound 102 may be reacted with a molecule containing an aldehyde functionality. The functional group (e.g., the phosphonium salt) may react with an aldehyde functionality under appropriate conditions to couple compound 102 to the dialdehyde. Compound 102 may be reacted with a dialdehyde in order to perform a double coupling as depicted below.

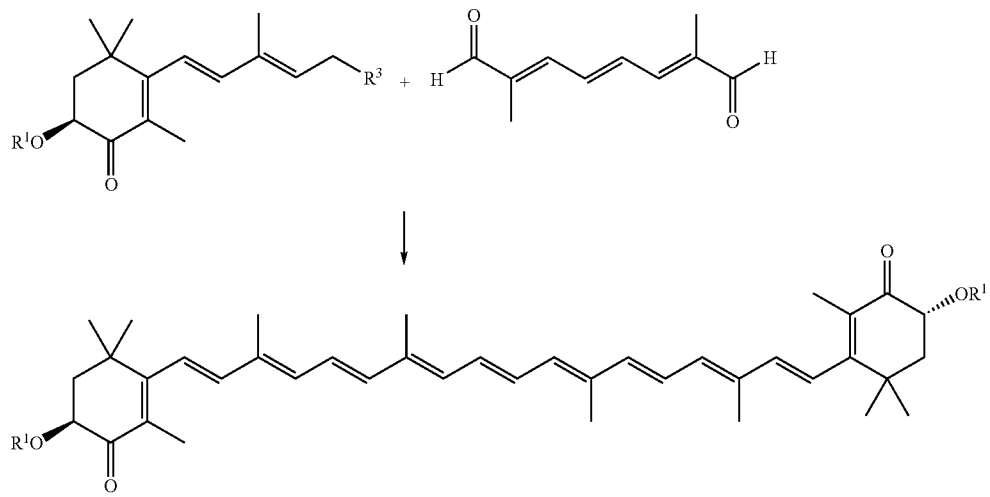

As shown above, the above-described sequence for the formation of astaxanthin may be accomplished in a stereoselective manner to give a single desired stereochemistry. While depicted as a stereoselective synthesis, it should be understood that the above described synthesize of astaxanthin may also be accomplished without control of the stereochemistry to give a statistical distribution of stereoisomers. In some embodiments, a method may include analyzing the distribution of stereoisomers of a carotenoid (e.g., astaxanthin). A method allowing analysis of the distribution of possible stereoisomers of a carotenoid may be used to determine the outcome of a synthetic method for preparing a carotenoid. The method may also be useful for checking the purity of carotenoid materials provided by chemical manufacturers. In one embodiment, a chiral HPLC column may be used to determine the stereoisomeric distribution of a carotenoid.

In an alternate embodiment, coupling of the headpiece unit with a coupling agent may be accomplished by forming pendant aldehyde groups on the headpiece and reacting them with a coupling agent as depicted below. In some embodiments, a carotenoid, may be synthesized by condensing a compound of the general formula with a compound of the general formula

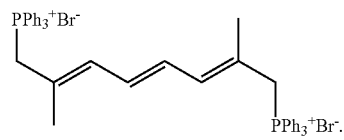

Condensation reactions using compounds such as those pictured above may, in some embodiments, be coupled under what are commonly known as Wittig condensation conditions. For example, the condensation may be carried out in the presence of an alkali metal alcoholate (e.g., sodium methylate, lithium carbonate, or sodium carbonate). The condensation may be carried out in the presence of an alkyl substituted alkylene oxide (e.g., ethylene oxide, 1,2-butylene oxide). Appropriate solvents may be used, such as alkanols (e.g., methanol, ethanol, isopropanol). The condensation may be carried out over a range of temperatures. In some embodiments, the condensation may be carried out below room temperature (e.g., 0° C.).

In one embodiment, intermediates used to synthesize astaxanthin may also be used to synthesize other carotenoids such as lutein and zeaxanthin. For example, lutein may be synthesized using the scheme depicted below.

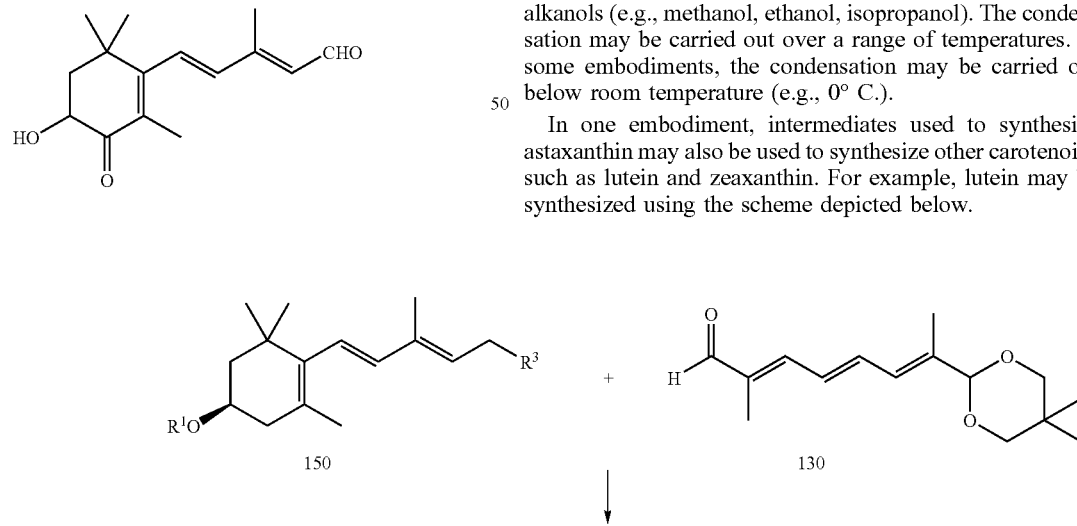

-continued

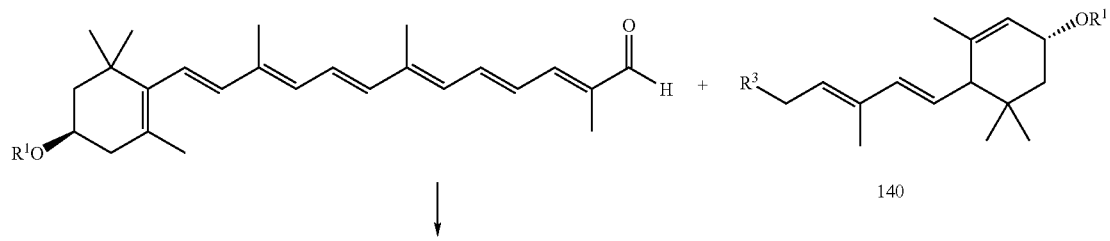

140

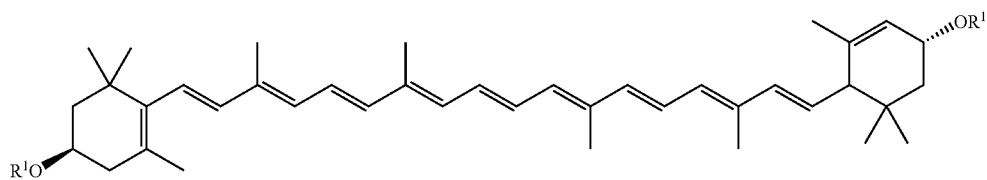

The synthesis of the intermediate 102 has been described before with respect to the synthesis of astaxanthin. Synthesis of the protected dialdehyde compound 130 and the unconjugated headpiece unit 140, have been described in literature procedures. The use of the synthetic methodologies described herein to obtain headpiece 102 may increase the efficiency and/or yield of the above-described synthesis of lutein.

In another embodiment, intermediates used to synthesize astaxanthin may also be used to synthesize other carotenoids such as zeaxanthin. For example, zeaxanthin may be synthesized using the scheme depicted below.

The synthesis of the intermediate 150 is based on a modified synthesis of the intermediate 102 used to make astaxanthin. As shown above, the final coupling of intermediate 150 with a dialdehyde yields zeaxanthin in an analogous manner to astaxanthin. Synthesis of intermediate 150 may be accomplished using the scheme depicted below.

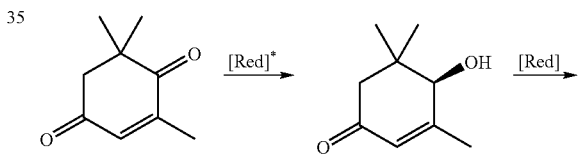

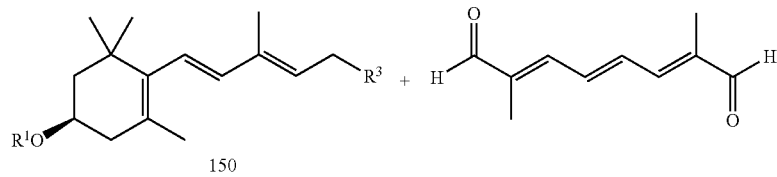

150

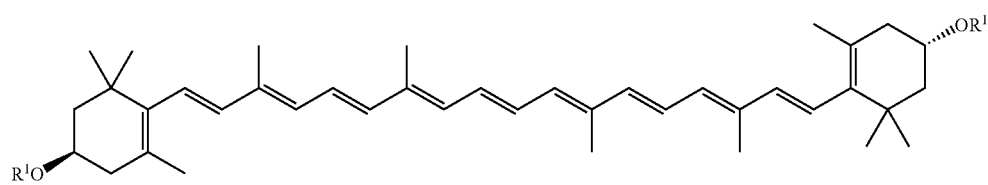

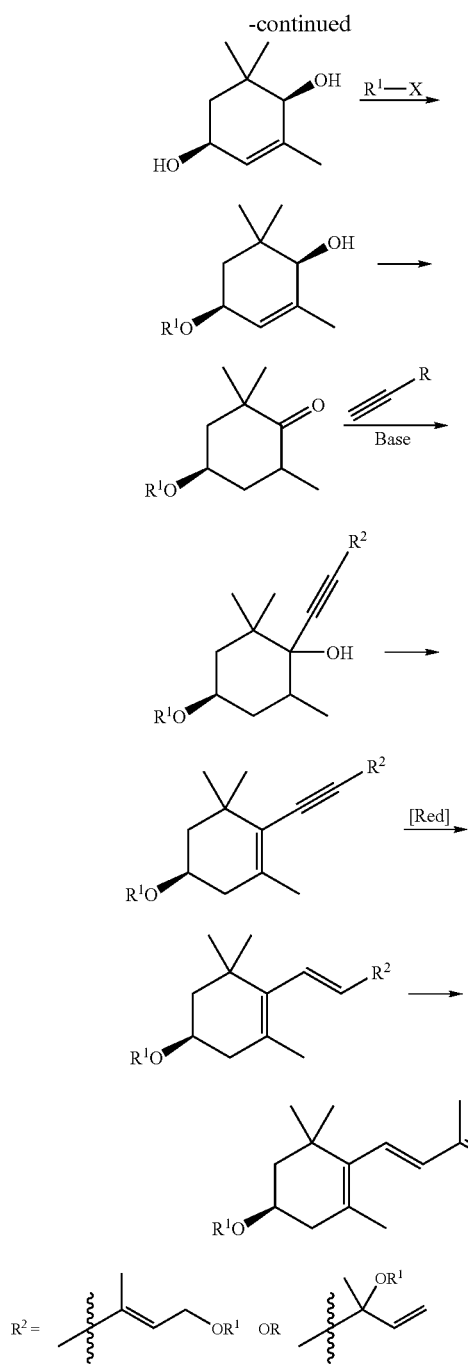

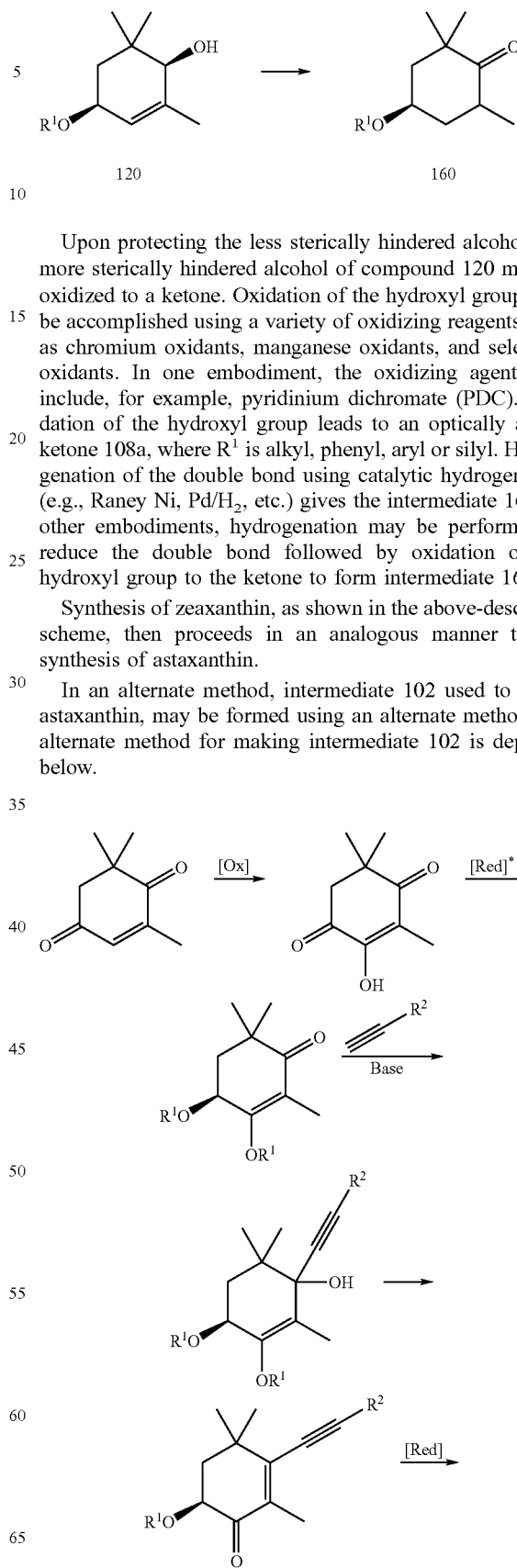

Upon protecting the less sterically hindered alcohol, the more sterically hindered alcohol of compound 120 may be oxidized to a ketone. Oxidation of the hydroxyl group may be accomplished using a variety of oxidizing reagents such as chromium oxidants, manganese oxidants, and selenium oxidants. In one embodiment, the oxidizing agent may include, for example, pyridinium dichromate (PDC). Oxidation of the hydroxyl group leads to an optically active ketone 108a, where $R^1$ is alkyl, phenyl, aryl or silyl. Hydrogenation of the double bond using catalytic hydrogenation (e.g., Raney Ni, Pd/$H_2$, etc.) gives the intermediate 160. In other embodiments, hydrogenation may be performed to reduce the double bond followed by oxidation of the hydroxyl group to the ketone to form intermediate 160.

Synthesis of zeaxanthin, as shown in the above-described scheme, then proceeds in an analogous manner to the synthesis of astaxanthin.

In an alternate method, intermediate 102 used to make astaxanthin, may be formed using an alternate method. An alternate method for making intermediate 102 is depicted below.

In some embodiments, synthesis of the intermediate 150 may be accomplished using the same synthetic techniques as have been described above for astaxanthin to obtain intermediate 120. Intermediate 120 may be converted into saturated ketone 160 using a procedure that is modified from the process used in the synthesis of astaxanthin. In an embodiment, a saturated ketone 160 may be formed by a two step procedure by oxidizing the hydroxyl group and reducing the double bond. Alternatively, the reduction of the double bond may be performed prior to oxidation of the hydroxyl group. The scheme for converting compound 120 to 160 is shown below.

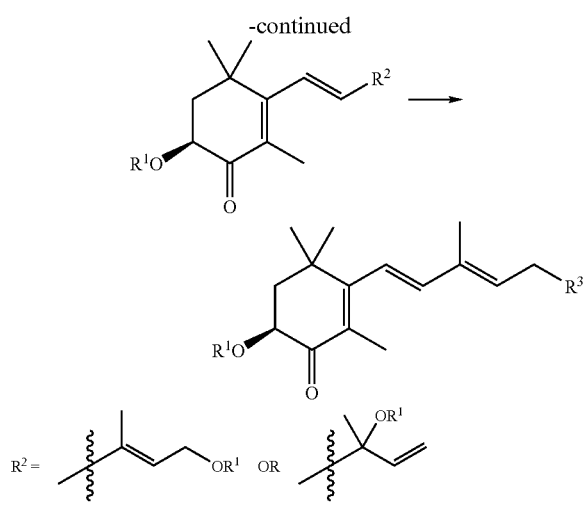

The method includes an initial step of oxidizing ketoisopherone to hydroxylated ketoisopherone as depicted below.

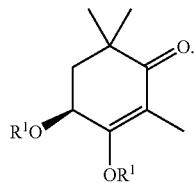

Suitable oxidants include chromium oxidants, manganese oxidants and peroxide oxidants. For example, in some embodiments, a cyclohexene derivative may be hydroxylated using hydrogen peroxide. After the compound has been oxidized, the hydroxylated product is reduced to form a dihydroxylated compound having the general structure

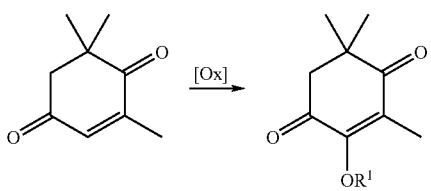

The method may also include protecting the dihydroxylated compound. In some embodiments, a dihydroxylate may be protected by reacting the dihydroxylated compound with a ketone (e.g., acetone). A ketone may be reacted with the dihydroxylated compound to form a protected dihydroxylated compound having the general structure

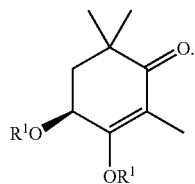

In some embodiments, $R^1$ may be alkyl (e.g., methyl), aryl or each $R^1$ together forms a cyclic ring. The method may include coupling an alkyne to the protected dihydroxylate to form an intermediate coupled product. In some embodiments, the intermediate coupled product may not be isolated.

Instead the intermediate product may be directly subjected to the next reduction process to give a product having the structure:

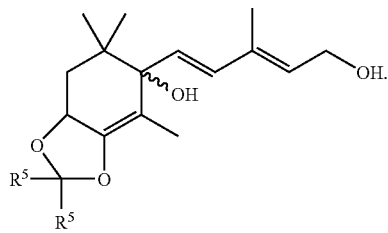

The intermediate coupled product may be transformed into a phosphonium salt product. In some embodiments, $R^5$ may be alkyl or aryl.

In some embodiments, a method may include transforming a hydroxylated product into a phosphonium salt product. Transforming the hydroxylated product into a phosphonium salt product may include reducing the hydroxylated product to form a dihydroxylated compound having the general structure

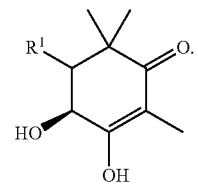

In some embodiments, the hydroxylated compound may be reduced stereoselectively.

The term "stereoselective reduction" may be generally defined as stereochemical reduction by which one of a pair of enantiomers, each having at least one asymmetric carbon atom, is produced selectively, i.e., in an amount larger than that of the other enantiomer. The stereo-differentiating reduction is classified into enantioface- and diastereo-differentiating reductions, by which optical isomers having one asymmetric carbon atom and those having two asymmetric carbon atoms are produced, respectively. The present reduction may be said to pertain to stereo-differentiating hydrogenation of carbonyl compounds.

In some embodiments, a carbonyl may be stereoselectively reduced such that the resulting chiral center comprises a stereochemistry of R or S comprising a stereoselectivity of greater than 50%. A stereoselectivity of a reduction may be greater than 75%. A stereoselectivity of a reduction may be greater than 90%. A stereoselectivity of a reduction may be greater than 95%. A stereoselectivity of a reduction may be greater than 99%.

A stereoselective reduction of a first carbonyl of ketoisophorone (KIP) may proceed as depicted:

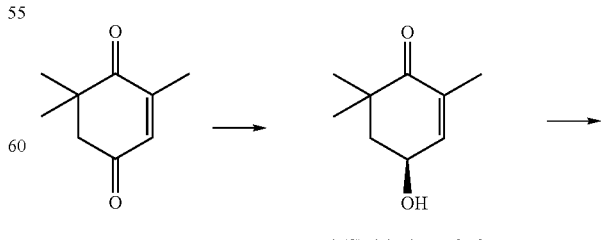

ketoisophorone     4 (S)-4-hydroxy-2, 6, 6-trimethyl-cyclohex-2-en-1-one

108c

-continued

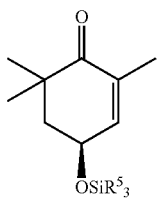

108b

In some embodiments, compound 108c (S-phorenol) may be a useful intermediate for the synthesis of certain carotenoids (e.g., zeaxanthin or astaxanthin).

Direct asymmetric reduction of KIP to 108c may save several steps relative to syntheses previously reported. Use of catalytic reagents for stereoselective reduction avoids expensive reagents used in stoichiometric amounts for reduction. Compound 108c may be useful for synthesis of carotenoids such as astaxanthin via derivative 108b.

KIP is known and commercially available and therefore a prime candidate for beginning a synthesis of some carotenoids with.

Reduction of ketoisophorone can occur at C-1 and/or C-4 and/or at the double bond, thus problems of regioselectivity and stereoselectivity must be solved.

1,2-reduction at C-4 has been achieved with a stoichiometric amount of the reagents sodium borohydride/cerium chloride (JOC, 1986, 491, incorporated herein by reference) to give racemic product. 1,2-reduction at C-4 has been achieved with 2-propanol in the presence of zirconium oxide catalyst to give racemic product (Bull Chem Soc Jap, 1988, 3283, incorporated herein by reference).

Compound 108c has been obtained by bioprocesses. Typical are product mixtures from non-selective reduction and over-reduction. See for example Agr Biol Chem, 1988, 2929 with *Aspergillus niger*, incorporated herein by reference, the product was the undesired 4R enantiomer. 108c has been obtained in up to 99% enantiomeric excess by esterase hydrolysis of the racemic chloroacetate ester. The maximum yield reported was 30%. The maximum theoretical yield is 50% (Tetr Assy. 1999, 3811, incorporated herein by reference). 108c has been obtained in homochiral form by asymmetric catalytic reduction of the enol acetate of KIP (U.S. Pat. No. 5,543,559 to Broger et al., incorporated herein by reference). This requires preparation of the enol acetate and hydrolysis of the product acetate to obtain 108c.

Direct asymmetric catalytic reduction of KIP has been reported using chirally modified ruthenium catalysts to obtain 108c in low selectivity and maximum 76% ee (Tetr Assy, 2000, 1849, incorporated herein by reference).

There are many methods known to one skilled in the art for stereoselectively reducing a carbonyl group. Stereoselective reductions may be carried out using catalytic reagents (e.g., chemical, biological). Biological catalysts may include for example living organisms (e.g., yeast) capable of facilitating a reduction of a carbonyl. Catalytic reagents may be used due to their efficiency. Efficiency may be related to more than just a yield of a reaction or turnover, but also may include cost of the reagent as well as total cost of running the reaction (e.g., cost of catalyst, mole percentage of catalyst required, ease of reclaiming catalyst). Catalysts may be more attractive as possible reducing agents on an industrial scale due to a reduction in related expenses.

In some embodiments, direct stereoselective reduction of KIP (including derivatives and analogs of KIP) to the alcohol product (including protected alcohols, such as ethers) may include the use of reagents such as boranes. Boranes may include at least one B—H bond (e.g., diborane, borane-THF complex, borane-methyl sulfide complex, phenoxyboranes (such as catechol borane), amine-borane complexes, or alkoxyboranes).

In some embodiments, borane reagents may include chiral substituents. Chiral catalysts may include chiral derivatives which form weak complexes with the borane reductant. Chiral catalysts which form weak complexes with borane reductants may include amine derivatives.

In some embodiments, chiral oxazaborolidine catalysts with borane-THF may be used to stereoselectively reduce KIP and its analogs and derivatives (as described by Prof EJ Corey in U.S. Pat. No. 4,943,635 and reviewed in Angew Chem Intl Engl, 1998, 37, 1986, both of which are incorporated herein by reference). In some embodiments, oxazaborolidine catalysts may include a compound having a general structure

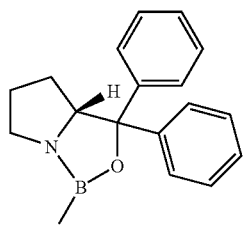

202

Using oxazaborolidine catalyst 202 with borane-THF as reductant, complete conversion may be achieved with 100% regioselectivity of reduction of the carbonyl at C-4 and a minimum of 25% enantiomeric excess.

Enantiomeric excesses of over 55% may be achieved using compound 202. In some embodiments, regioselectivity and enatiomeric excess may vary with temperature, the B–H source, and/or the structure of the catalyst.

Enantiomeric excesses may be improved with purification techniques known to one skilled in the art. In some embodiments, a chiral product may be purified via crystallization. Compound 108c is a crystalline solid whereas the racemate is typically obtained as non-crystalline. Therefore crystallization of product to chiral purity may be a useful means of achieving this end.

A stereoselective reduction of a first carbonyl of substituted ketoisophorone (KIP) may proceed as depicted:

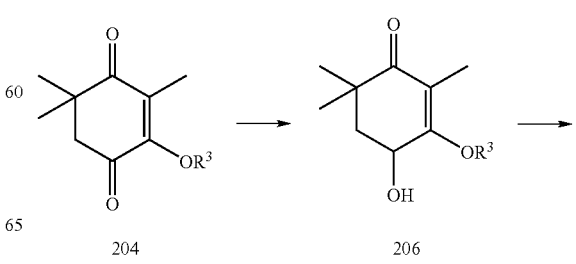

204      206

-continued

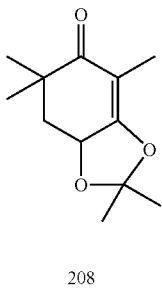

208

$R^3$ may be $SiR^5_3$, H, alkyl, or aryl. Compound 204 ($R^3$=H) is a known substance, found naturally and prepared synthetically. The only other known example of structure 204 is the methyl ether ($R^3$=CH$_3$) which was prepared as an analytical derivative for characterization of natural product 204 ($R^3$=H).

206 ($R^3$=H) and 208 are known substances (racemic and enantiomers) and demonstrated useful intermediates for the synthesis of racemic or homochiral astaxanthins (Helv Chim Acta, 1981, 240, 2447, 2463, incorporated by reference herein). Derivatives and analogs of 206 ($R^3$=H) and 208 provide useful intermediates for the synthesis of racemic or homochiral carotenoids, as well as, other natural products and their derivatives and analogs.

Preparation of 204 ($R^3$=H) from ketoisophorone was described in Helv Chim Acta, 1981, 2436, which is incorporated herein by reference. Reduction of 204 to racemic 206 ($R^3$=H) using zinc in acid or hydrogen and Raney nickel and subsequent conversion to racemic 208 are also described therein. Preparation of the pure enantiomers of 206 ($R^3$=H) by resolution of racemic 206 ($R^3$=H) via diastereomeric alpha-phenylamine salts are described therein.

Desirable is direct asymmetric reduction of 204 to 206 and conversion to homochiral 208 for use in the synthesis of homochiral carotenoids (e.g., astaxanthin). This sequence avoids the need for problematic oxidation steps which are required when the 3-hydroxy or 3-alkoxy substituents are absent. The presence of a C-3 substituent may facilitate the asymmetric reduction of the carbonyl at C-4.

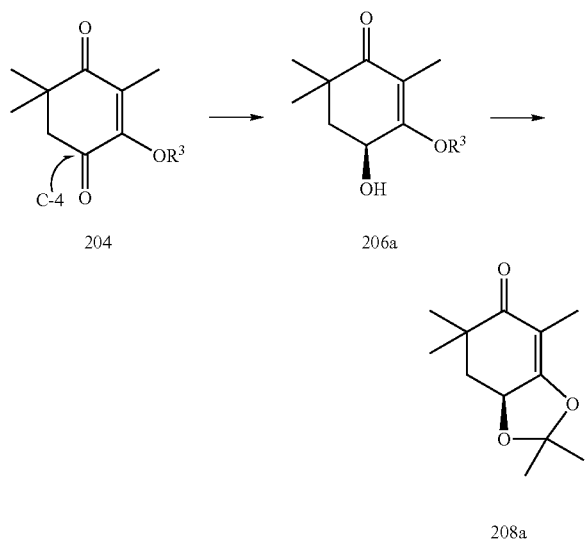

The only prior asymmetric reduction of 204 reported is a bioreduction of 204 ($R^3$=H) reported to give the 4S isomer of 206a ($R^3$=H) in 65% enantiomeric excess (Helv Chim Acta, 1981, 240, 2447, incorporated by reference herein).

In some embodiments, a method may include preparation of epoxyketoisophorone from ketoisophorone.

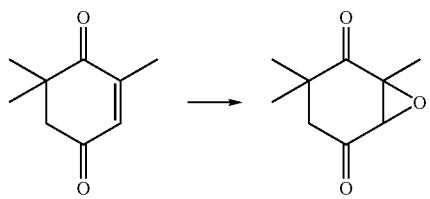

An epoxide of ketoisophorone may be prepared using reagents including, but not limited to, peroxides (e.g., hydrogen peroxide). There are many epoxidation reactions known to one skilled in the art, many of which include peroxides (e.g., m-ClC$_6$H$_4$CO$_3$H). There are other epoxidation reagents described in references such as "Comprehensive Organic Transformations: A Guide to Functional Group Preparations" Larock, R. C. VCH Publishers, Inc. pages 456–461, which is incorporated herein by reference.

In some embodiments, a method may include preparation of 3-hydroxyketoisophorone from epoxyketoisophorone.

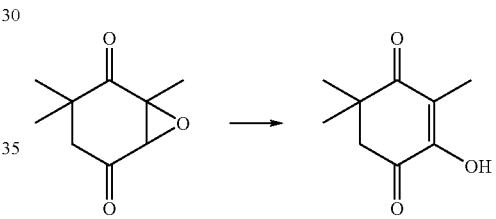

A hydroxide anion (e.g., sodium hydroxide), followed by acidification of the solution may be employed to convert the epoxide to the hydroxide.

In some embodiments, a method may include preparation of 3-methoxyketoisophorone from 3-hydroxyketoisophorone.

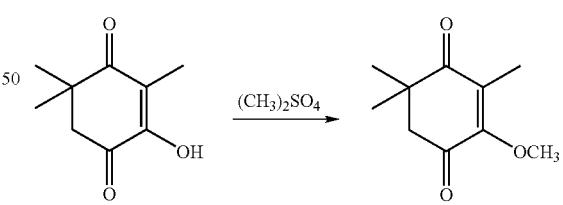

A base (e.g., sodium hydroxide, sodium carbonate) may be used to deprotonate the hydroxide in a solvent (e.g., dimethyl formamide, methanol). A methylating reagent (e.g., dimethylsulfate) may then be added to the oxide anion in order to prepare the methoxy substituent. The methyl group may act as a protecting group masking the hydroxy group from reagents used in later transformations. There are many protecting groups for hydroxy groups known to one skilled in the art (e.g., silyl protecting groups).

In other embodiments, the hydroxy substituent of 3-hydroxyketoisophorone may be methylated using diazomethane. Other alkylation methods may include going through an intermediate (e.g., a mesylate) which is subsequently subtituted with a methoxy substitutent. An alkylation (e.g., methylation) may also be accomplished by using a methylating agent such as trimethyl orthoformate and an acid (e.g., trifluoroacetic acid) in a solvent (e.g., methanol).

In some embodiments, the alkylation step may be circumvented by opening the epoxy group of, for example, epoxyketoisophorone with a methoxide salt (e.g., sodium methoxide) along with simultaneous dehydration.

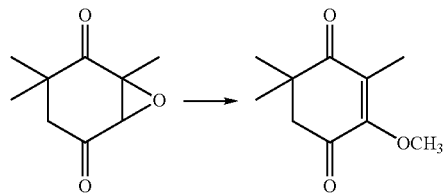

In some embodiments, a method may include preparation of 4-(S)-hydroxy-ketoisophorone from 3-methoxyketoisophorone.

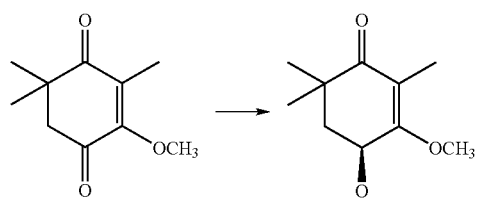

A hydrogen source (e.g., H$_2$) may be used to reduce a carbonyl to a hydroxide group. A catalyst may be used to catalyze the reduction. In some embodiments, an enantiomeric excess of a particular enantiomer may be achieved without the use of stereoselective reagents. In some embodiments, stereoselective reagents (e.g., chiral catalysts) may be used to produce a specific enantiomer. In some embodiments, reagents which are not typically stereoselective reagents may be used to reduce a carbonyl to a hydroxy group. The reaction may not be stereoselective. The reaction may be stereoselective, but may be stereoselective due to the inherent nature of the molecule. For example sodium borohydride may be used to reduce the carbonyl to the hydroxy compound.

In some embodiments, a method may include preparation of 4-hydroyxketoisophorone acetone ketal from 4-(S)-hydroxy-ketoisophorone.

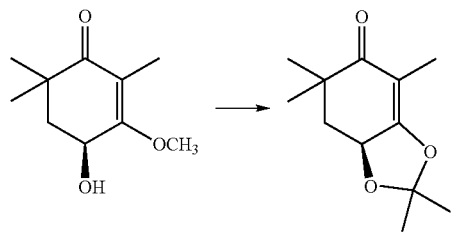

A diol may be converted to an acetal using a ketone (e.g., acetone) and an acid (e.g., p-toluenesulfonic acid hydrate). The acetal group may act as a protecting group masking the diol from reagents used in later transformations. There are other protecting groups for diols known to one skilled in the art. In some embodiments, one or more of the synthetic steps of a method for preparing 4-hydroyxketoisophorone acetone ketal may be combined into a "one-pot reaction" and/or an intermediate may not be isolated and/or purified before exposing it to another set of reagents.

In some embodiments, a method may include stereoselectively reducing a carybonyl 1 of a compound 210 having the general structure

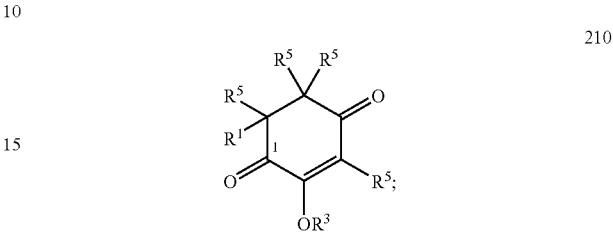

to form a chiral center 2 of a compound 212 having the general structure

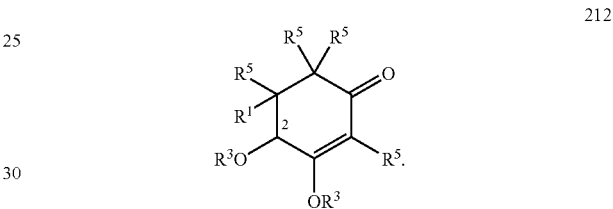

$R^1$ may be H or $OR^3$. $R^3$ may be $SiR^5_3$, H, alkyl, or aryl. $R^5$ may be H, alkyl, or aryl.

In some embodiments, $R^3$ of compound 204 may include alkyl, substituted alkyl, aryl. Alkyl may include alkyl substituents, where alkyl comprises two or more carbons. Compound 204, where $R^3$=H (or salts thereof) and $R^3$=alkyl, heteroalkyl, aryl, heteroaryl, aralkyl, or heteroaralkyl, are useful substrates for asymmetric reduction for preparation of isomers of compound 206. $R^3$ may include other substituents not listed known to one skilled in the art, even substituents typically unstable during reductive conditions may be used if protected properly using known functional protection methodology.

In some embodiments, salts formed from compound 204 ($R^3$=H) may include metals of period I or II or transition metals compatible with the reductants, ammonia, or amines (e.g., alkyl, substituted alkyl, aryl, heteroaryl, primary, secondary, or tertiary), or phosphines (e.g., alkyl, substituted alkyl, aryl, heteroaryl, primary, secondary, or tertiary). Salts formed from compound 204 ($R^3$=H) may contain chirality in their structures or as associated ligands.

In some embodiments of ethers of compound 204, $R^3$ may be any alkyl, aryl, heteroaryl, aralkyl, or heteroaralkyl group compatible with the reduction conditions. Any of the R groups may contain chiral centers or associated chiral ligands. In certain embodiments, $R^3$ may be an alkyl group comprising from one to eight carbons.

A reductant may be selected from among the classes of: hydrogen, a non-gaseous hydrogen source (e.g., reduction with an alcohol, formic acid, etc.), a nucleophilic metal hydride (e.g., NaBH$_4$ etc.), a covalent metal hydride (e.g., Dibal), a non-metal hydride (e.g., boranes or silanes) or metal catalyzed transfer of hydride from alcohols (e.g., Meerwein-Pondorf-Verley reduction). The reductant may be chiral. In certain embodiments, reductants, may include hydrogen, formic acid, isopropanol, or sec-butanol.

Catalysts for hydrogenation or transfer hydrogenation may be chosen from among transition metals or metal ions (e.g., such as nickel, cobalt, platinum, palladium, iridium, rhodium, and ruthenium, modified with chiral ligands or surface modifiers) capable of facilitating reduction of ketones selectively over reduction of other moieties (e.g., esters). In certain embodiments, catalysts for hydrogenation or transfer hydrogenation may be complexes of rhodium (I) or Ruthenium (II) with $C_2$-symmetric ligands or platinum metal modified with chiral cinchona alkaloids. Examples of ligands are known to one skilled in the art.

At least some of the intermediates 206 ($R^3$=alkyl, etc.) are found to be crystalline. It is a desirable feature that the chiral purity of compound 206 may be upgraded by recrystallization.

It has been previously reported that compound 206 ($R^3$=H) may be converted to 208 by treatment with acetone or acetone ketals in the presence of acid catalysts in either the racemic or chiral series. It is reported here that compound 206 ($R^3$=alkyl, etc.) may be converted to compound 206 ($R^3$=H) under acidic hydrolytic conditions. It was surprisingly found that compound 206 ($R^3$=alkyl, etc.) may be converted to compound 208 when treated with acetone in the presence of acidic catalyst.

Compound 204 may be prepared from commercially available ketoisophorone by several means:

1. alkylation of 204 ($R^3$=H) with alkyl halides or sulfates in the presence of base and solvent as appropriate. Preferred is dimethylsulfate with sodium hydroxide in water, in the optional presence of methanol;
2. treatment of 204 ($R^3$=H) with alcohols or phenols in the presence of an acid catalyst under conditions for physical removal of water (e.g., distillation or azeotropic distillation) or chemical removal of water (e.g., presence of a ketal or orthoester); and
3. epoxidation of ketoisophorone followed by treatment with alkoxide or phenoxide.

In some embodiments, a carbonyl may be stereoselectively reduced, as for example:

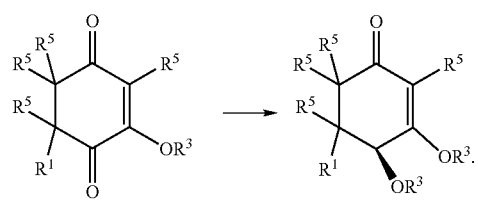

In some embodiments, $R^1$ may be $R^5$, $OSiR^5_3$, or $OR^5$. $R^3$ may be $SiR^5_3$, aryl, or alkyl. Alkyl may comprise two or more carbons. $R^5$ may be H, alkyl, or aryl. In some embodiments, $R^5$ may be methyl. $R^3$ may be methyl or hydrogen. A carbonyl may be stereoselectively reduced as below

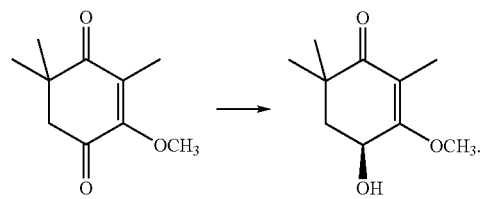

In some embodiments, a method for reducing a carbonyl may include selectively reducing a first carbonyl in the presence of a second carbonyl. The second carbonyl may be chemically distinguishable from the first carbonyl. For example the first carbonyl may be electronically distinguishable from the second carbonyl. The second carbonyl may not be reduced using the described method for reducing the first carbonyl. For example the second carbonyl may be described as a vinylic ester and/or and ester. The second carbonyl may be sterically hindered. For reasons such as these, a first carbonyl may be regioselectively reduced.

In some embodiments a reduction catalyst may be a chiral catalyst. In one embodiment, a chiral catalyst includes a transition metal and an optically active chiral ligand. Transition metals that may be used to form a chiral catalyst for reduction of ketones include Ti, Zr, Hf, V, Nb, Ta, Cr, Mo, W, Mn, Re, Fe, Ru, Os, Co, Rh, Ir, Ni, Pd, Pt, Cu, Ag, and Au. In some embodiments, a ruthenium chiral catalyst may be used to effect a stereoselective reduction of keto-α-isopherone. The ruthenium chiral catalyst may be formed from a mixture of $[RuX_2(\eta^6-Ar)]_2$ with an optically active amine, where X represents a halogen (e.g., F, Cl, Br, I) and Ar represents benzene or a substituted benzene (e.g., alkyl substituted benzene). In some embodiments, the optically active amine includes both (S)- and (R)-amino acids, and other optically active amines such as as $H_2N$—CHPh-CHPh-OH, $H_2N$—CHMe-CHPh-OH, MeHN-CHMe-CHPh-OH, and TsNH-CHPh-CHPh-$NH_2$.

In some embodiments, a chiral catalyst may include a catalyst having the structure

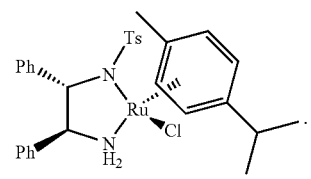

In some embodiments, a method may include a stereoselective reduction such as

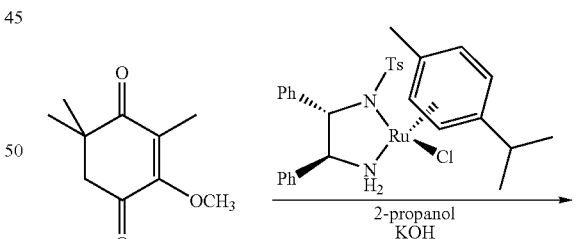

204b
2-Methoxy-3,5,5-trimethyl-cyclohex-2-ene-1,4-dione

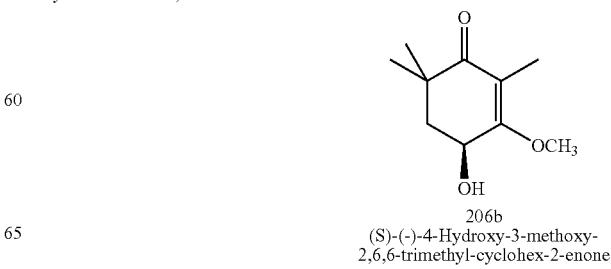

206b
(S)-(-)-4-Hydroxy-3-methoxy-2,6,6-trimethyl-cyclohex-2-enone

In some embodiments, a solution of (1S,2S)-N-p-toluene-sulfonyl-1,2-diphenylethylenediamine may be added to dichloro(p-cymene)ruthenium(II)dimer. The suspension may be heated as necessary during which time the solids may go into solution. The reaction may be cooled to room temperature, a solution of 204b may be added followed by KOH.

The method may include protecting the dihydroxylated compound. In some embodiments, a dihydroxylate may be protected by reacting the dihydroxylate with a ketone (e.g., acetone). A ketone may be reacted with the dihydroxylate compound to form a protected dihydroxylate compound having the general structure

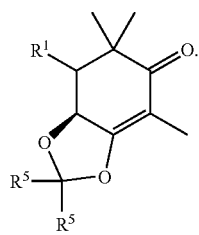

In some embodiments, $R^5$ may be alkyl (e.g., methyl) or aryl. The method may include coupling the protected diol to form an intermediate coupled product. In some embodiments, the intermediate coupled product may not be isolated. The intermediate coupled product may include a compound having the general structure

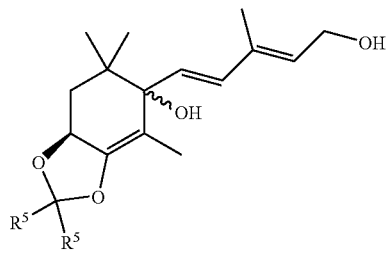

The intermediate coupled product may be transformed into a phosphonium salt product having the general structure

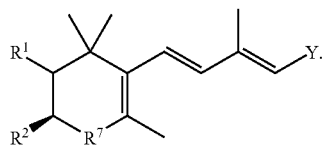

In some embodiments, a synthetic sequence may include:

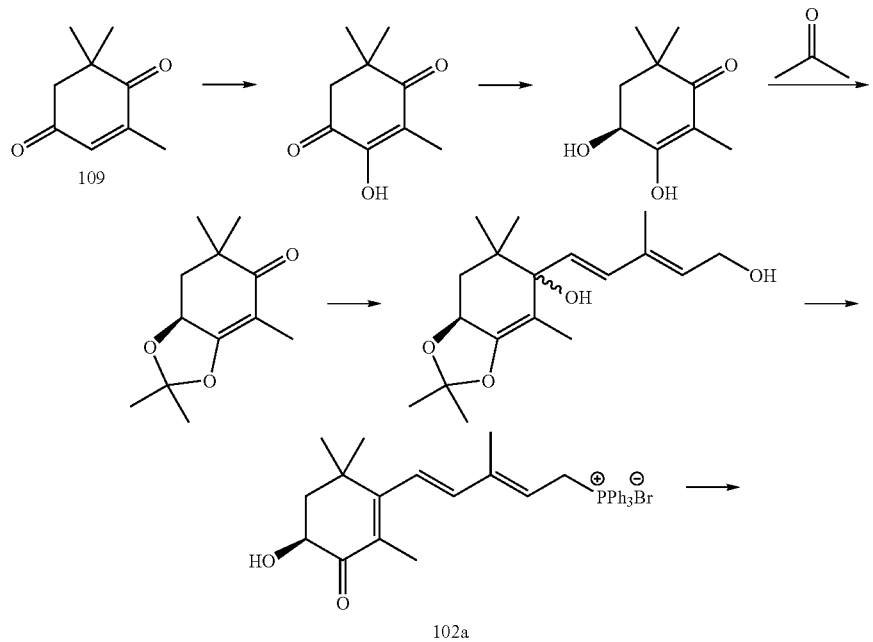

102a

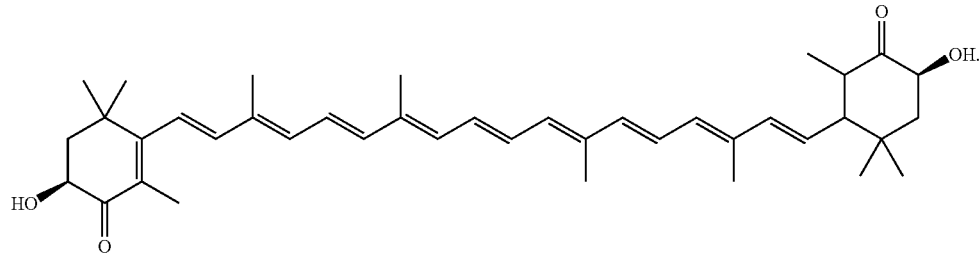

2E

In some embodiments, an alkyne may be formed via the following synthetic sequence

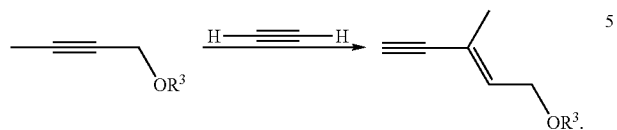

In some embodiments, $R^3$ may be $SiR^5{}_3$, H, alkyl, or aryl. $R^5$ may be alkyl (e.g., methyl) or aryl. $R^3$ may include a protecting group, such as the described silyl protecting group. There are many protecting groups known to one skilled in the art for masking or protecting hydroxy functionalities. Different protecting groups may be used depending upon what conditions one wants to protect the hydroxy group under and/or what conditions one desires to deprotect and "unmask" the hydroxy group. The above synthetic sequence may embody other types of optically active and/or non optically active endproducts. In some embodiments, at least some of the synthetic steps may be carried out in a similar manner to similar chemical reactions as described in other synthetic schemes as described herein above and/or in the Examples section.

In some embodiments, an isomer of the alkyne coupled to the protected diol as described above may be employed to couple to the protected diol. The isomer of the alkyne may include a compound having the general structure

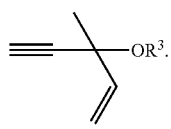

In some embodiments, the isomer of the alkyne may be synthesized by coupling acetylene and methyl vinyl ketone. In some embodiments, the acetylene may be added to the methyl vinyl ketone via 1,2 addition.

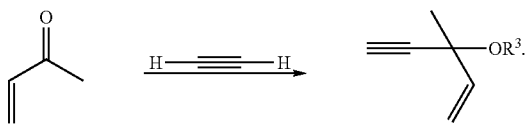

Due to the instability of methyl vinyl ketone other synthetic routes my be employed to provide the desired product. In some embodiments, stable chemical equivalents of methyl vinyl ketone may be used. Stable equivalents may include 2-(beta-bromoethyl)-2-methyl-1,3-dioxolane.

In certain embodiments, carotenoids which may be synthesized using methods described herein may include carotenoids based on a chemical intermediate having the general structure

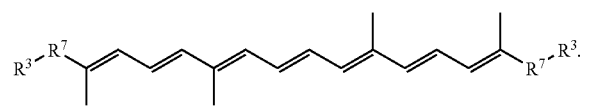

The compound depicted above embraces racemic, optically active stereoisomers and optically inactive stereoisomers. In some embodiments, $R^3$ may be $OR^5$, $OSiR^5{}_3$, H, alkyl, or aryl. $R^5$ may be H, alkyl, or aryl. In some embodiments, $R^7$ may include C—$R^3$ or C=O. A method of synthesizing such a compound may include transforming a halogenated derivative having the general structure

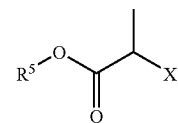

into a phosphorous compound having the general structure

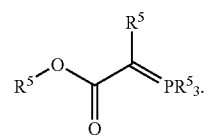

In some embodiments, $R^5$ may be alkyl or aryl. X may be a halogen (e.g., Br, Cl). The method may include reacting the phosphorous compound with an aldehyde or an aldehyde equivalent having a general structure

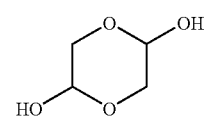

to form a alcohol coupling product having the general structure

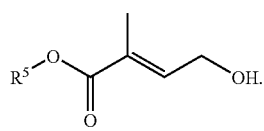

The method may include transforming the alcohol coupling product into a halogenated coupling product having the general structure

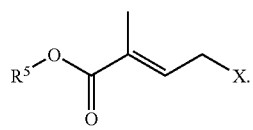

In some embodiments, $R^5$ may be alkyl or aryl. X may be a halogen (e.g., Br, Cl).

In some embodiments, a method may include transforming the halogenated coupling product into a phosphonium salt product having the general structure

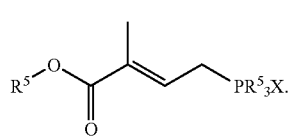

$R^5$ may be alkyl or aryl. X may be a halogen (e.g., Br, Cl).

In some embodiments, a method may include reacting the phosphonium salt product with a dialdehyde having the general structure

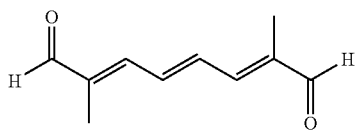

to form a carotenoid chemical intermediate having the general structure

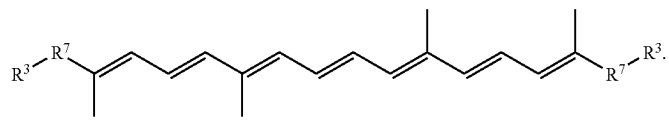

In some embodiments, $R^3$ may be $OR^5$, $OSiR^5{}_3$, H, alkyl, or aryl. $R^5$ may be H, alkyl, or aryl. In some embodiments, $R^7$ may include C—$R^3$ or C=O.

In some embodiments, a carotenoid chemical intermediate may include a compound having the general structure

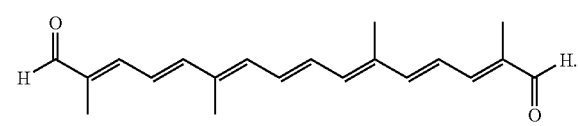

In some embodiments, a synthetic sequence may include:

In some embodiments, carotenoid chemical intermediates may be used to synthesize naturally occurring carotenoids as well as carotenoid analogs and carotenoid derivatives. Carotenoid chemical intermediates may be used to synthesize naturally occurring carotenoids such as lycopene and lycophyll, and lycopene/lycophyll analogs and lycopene/lycophyll derivatives.

In some embodiments of a method to synthesize lycopene and lycophyll, and its derivatives and/or analogs, the chemical intermediate pictured above having the general structure

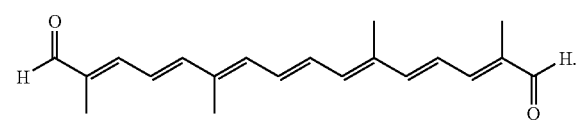

may be coupled with a phosphonium salt product having the general structure

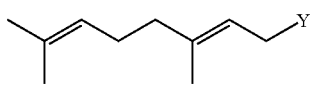

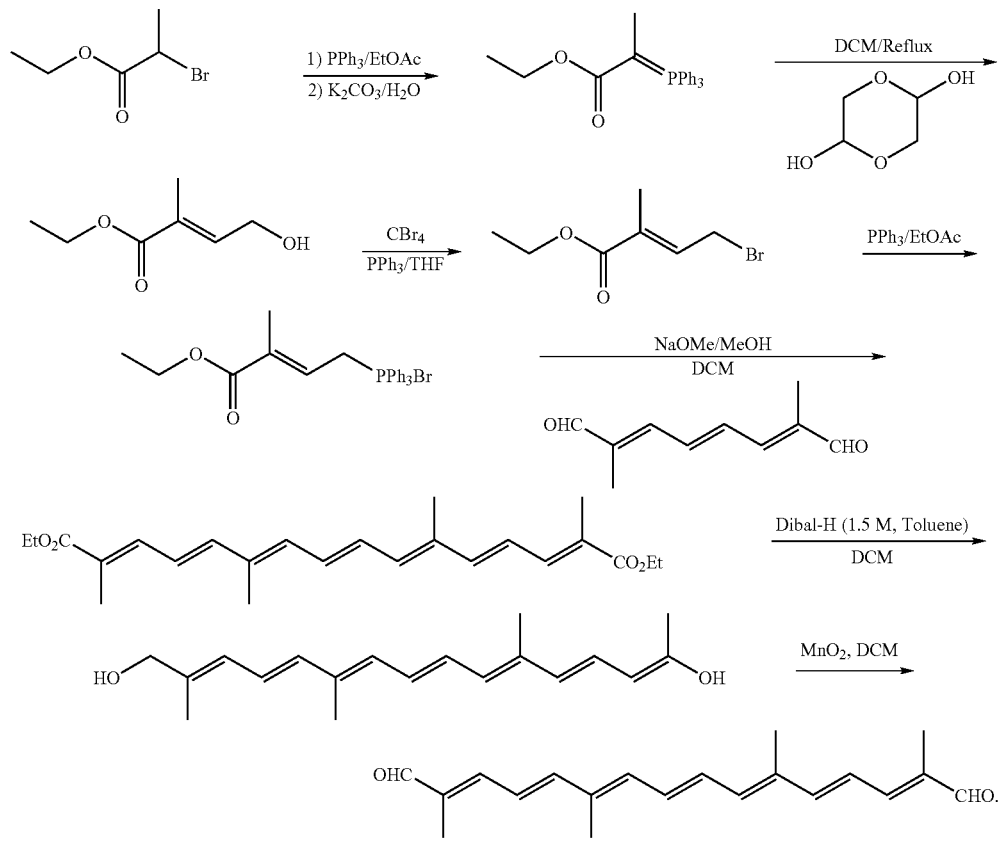

to form lycopene having the general structure

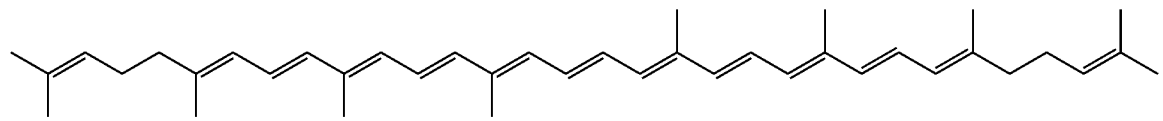
2F

In some embodiments, Y may include —CH$_2$—PR$^5_3$ or —CH$_2$—P(=O)(OR$^5$)$_2$. R$^5$ may be alkyl or aryl.

In some embodiments, methodologies as described herein (e.g., methods for synthesizing lycopene) may be used to prepare acyclic carotenoids, as well as, derivatives and/or analogs of acyclic carotenoids. Of course it is understood that at least some of the intermediates used to synthesize acyclic carotenoids are also useful in the preparation of carotenoids containing cyclic rings (referred to herein sometimes as cyclic carotenoids, e.g., astaxanthin).

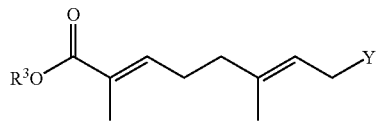
216 to form protected carotenoid 218 having the general structure

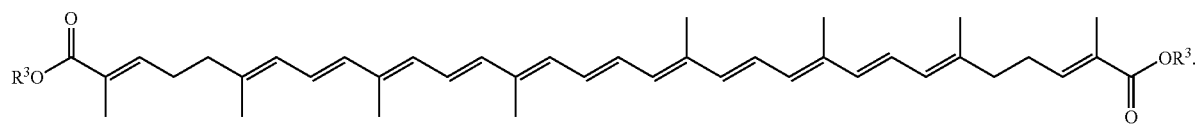
218

In some embodiments, a compound prepared by the method described herein may include an enantiomeric excess of at least one of the possible stereoisomers of the compound.

In some embodiments, a compound prepared by the method described herein may include an excess of a stereoisomer relative to the stereoisomer's statistical abundance.

In certain embodiments, carotenoids, carotenoid derivatives, or carotenoid analogs which may be synthesized using methods described herein may include carotenoids based on a chemical intermediate having the general structure

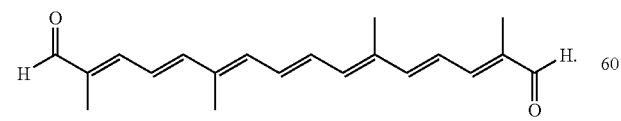
214

Compound 214 may be coupled to a phosphonium salt product 216 having the general structure In some embodiments, Y may be PR$^5_3$ or P(=O)(OR$^5$)$_2$. R$^3$ may be SiR$^5_3$, H, alkyl, or aryl. R$^5$ may be alkyl or aryl. In some embodiments, a solution of LiOMe (e.g., in methanol) may be used to couple the two compounds to prepare the protected carotenoid.

In some of the phosphonium salt product 216 embodiments, Y may be PR$^5_3$, R$^5$ may be phenyl, and such that phosphonium salt product 216 has the general structure

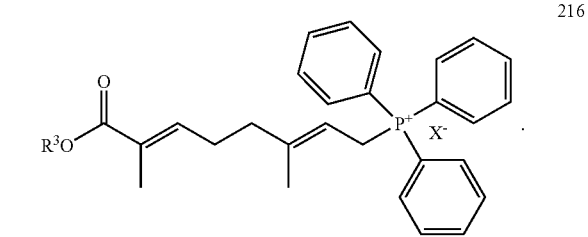
216

In some embodiments, X may be F, Cl, Br, or I. In some embodiments, R$^3$ may be methyl and X may be Br.

In some embodiments, a method may include reducing protected carotenoid 218 to form carotenoid 220 having the structure

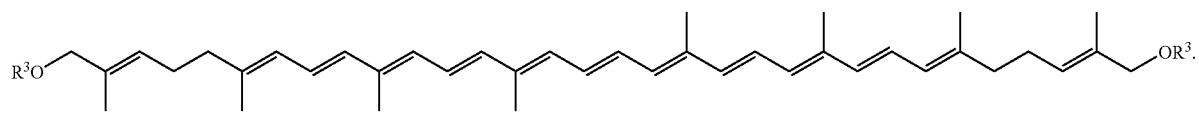

220

In some embodiments, $R^3$ may be $SiR^5{}_3$, H, alkyl, or aryl. $R^5$ may be alkyl or aryl. In some embodiments, $R^3$ may be H when protected carotenoid 218 is reduced to an alcohol forming carotenoid 2H. Reducing agents (e.g., DIBAL or Diisobutylaluminium hydride) known to one skilled in the art may be used to reduce the protected carotenoid 218 to form the carotenoid 220. Other reducing agents known to one skilled in the art may be used.

In some embodiments, carotenoid derivatives and analogs may be synthesized from naturally occurring carotenoids. These carotenoids may be synthetically produced and/or isolated from natural sources.

In some embodiments, a method may include condensing carotenoid 220 with succinic anhydride to prepare compound 222 having the general structure 222. In some embodiments, $R^3$ may be $SiR^5{}_3$, H, alkyl, or aryl. $R^5$ may be alkyl or aryl. In some embodiments, $R^3$ may include a co-antioxidant (e.g., Vitamin C, Vitamin C analogs and derivatives) and/or other substituents described herein. A base (e.g., N,N-diisopropylethylamine in a solvent such as $CH_2Cl_2$) may be used to facilitate condensation of carotenoid 220 to succinic anhydride. A non-nucleophilic base may be used. The method may include forming a salt 224 of compound 222 having a general structure 224. wherein X is a counterion. In some embodiments, X may be a counterion. X may include inorganic salts and/or organic salts. X may include, but is not limited to, Li, Na, or K. NaOMe may be used to convert the acid to the salt. Other reagents such as LiOMe, NaOEt, as well as other based may be used to prepare the salt.

In some embodiments, a method may include phosphorylating carotenoid 220 to form compound 226 having the general structure 221. In some embodiments, Y may be PR$^5_3$ or P(=O)(OR$^5$)$_2$. R$^3$ may be SiR$^5_3$, H, alkyl, or aryl. R$^3$ may be H, alkyl, benzyl, or aryl. The method may include forming a salt 223 of compound 226 having a general structure

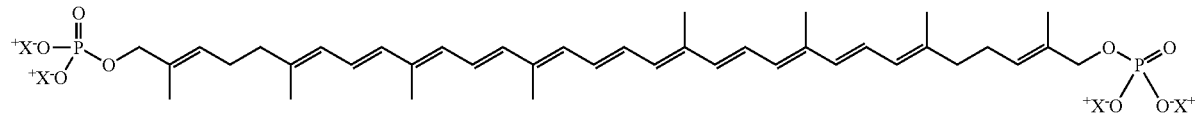

223. In some embodiments, X may be a counterion. X may include inorganic salts and/or organic salts. X may include, but is not limited to, Li, Na, or K. NaOMe may be used to convert the acid to the salt. Other reagents such as LiOMe, NaOEt, as well as other bases may be used to prepare the salt.

In some embodiment, a method may include preparing phosphonium salt product 216 by oxidizing ester 228 having the general structure

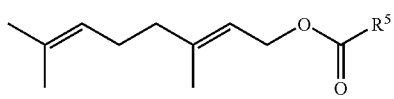

to form aldehyde 230 having the general structure

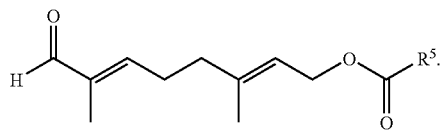

Selective oxidizing agents (e.g., SeO$_2$ in a solution of for example 95% ethanol) may be used to oxidize up to the aldehyde. The method may include oxidizing aldehyde 230 to form oxidized product 232 having the general structure

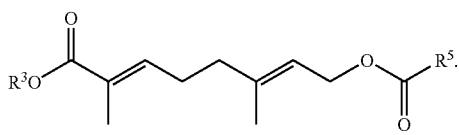

Selective oxidizing agents (e.g., NaClO$_2$, Na$_2$HPO$_4$, Me$_2$C=CHMe, t-BuOH/H$_2$O) may be used to oxidize up to the acid and/or ester. Oxidized product 232 may be selectively deprotected to form product 234 having the general structure

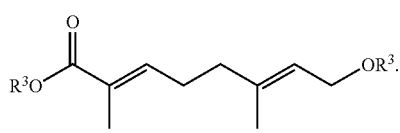

Selective bases (e.g., K$_2$CO$_3$, MeOH/H$_2$O) may be used to convert oxidized product 232 (e.g., to the alcohol and/or ether). Conversion of product 232 to product 234 may be viewed as more of a deprotection of an alcohol. The method may include halogenating product 234 to form halogenated product 236 having the general structure

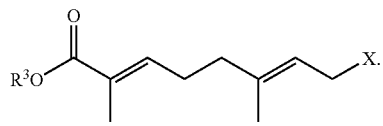

In an embodiment where product 234 includes an alcohol, halogenation of alcohols may be accomplished by a variety of methods (e.g., CBr$_4$/Ph$_3$P in a polar solvent such as THF). Halogenated product 236 may be converted to the phosphonium salt product 216. Conversion of the halogen to the phosphonium salt may include using Ph$_3$P in a solvent such as EtOAc. In some embodiments, X may be a counterion. X may include inorganic salts and/or organic salts. X may include F, Cl, Br, or I. R$^3$ may be SiR$^5_3$, H, alkyl, or aryl. R$^5$ may be alkyl, benzyl, or aryl.

In some embodiments, a multi-gram scale total synthesis of lycophyll (16,16'-dihydroxy-lycopene; ψ,ψ-carotene-16,16'-diol) may be based on a 2 (C10)+C20 synthetic methodology using the commercially available materials geraniol (C10) and crocetindialdehyde (C20). A late-stage double Wittig olefination of crocetindialdehyde may be used to form the lycophyll scaffold. The double Wittig may generate a mixture of polyenic geometric isomers that may be separated (e.g., using HPLC). The all-tranis lycophyll may be achieved in >95% purity using about 8 linear synthetic steps. The disuccinate and diphosphate sodium salts of the rare carotenoid may then be prepared. Carotenoid derivatives and analogs (e.g., disuccinate and diphosphate sodium salts) may be readily dispersible in water without need for heat, detergents, co-solvents, or other additives. Retrometabolic in design, these novel derivatives could find utility in those applications where parenteral delivery of therapeutically relevant forms of lycophyll are desired.

Studies in cultured human cells have shown that lycopene 2F, the primary carotenoid in tomatoes, can be growth inhibitory against transformed cells as well as normal prostatic epithelium, alone and/or in combination with other antioxidants (e.g. vitamin E). In animal studies, the results regarding protection against proliferation of transformed cells induced with various carcinogenic agents have been positive. For example, in the ferret, the most representative model in terms of absorption-distribution-metabolism-excretion (ADME) for humans, lycopene was in fact protective against cigarette-smoke induced lung pathology. Epidemiological studies in humans clearly support an association between dietary consumption of lycopene-containing food products and a lower risk of prostate cancer. These lycopene-containing food products also contain lycophyll, albeit in lower relative amounts. In some cases, the natural dietary mixture of carotenoid compounds has efficacy in these settings, and synthetically-prepared or naturally-isolated lycopene does not. In some embodiments, a method of treating disease in a human subject may include administering to the human subject a pharmaceutical or nutraceutical composition including a predetermined ratio of two or more geometric and/or stereoisomers of a structural analog or derivative or synthetic intermediate of a carotenoid. In some embodiments, a method of treating disease in a human subject may include administering to the human subject a pharmaceutical or nutraceutical composition including a predetermined ratio of two or more structural analogs or derivatives or synthetic intermediates of a carotenoid. Prospective, randomized clinical trials in humans also demonstrate improved indices of proliferation and oxidative stress across a range of oral doses in cancer patients. Delivery of a highly potent radical scavenger to prostatic tissue may restore or augment endogenous antioxidant levels.

Lycoxanthin 2G and lycophyll 2H, which can be isolated from the red, ripe berries of *Solanum dulcamara*, as well as tomatoes and watermelon, are C40 lycopene-like xanthophylls functionalized with primary hydroxyl groups. The originally proposed chemical structures of the xanthophylls however lacked complete assignment and required further studies that were realized in the early 1970's. Utilizing high-resolution mass spectroscopy and NMR, the regiochemistry of the hydroxyl groups was characterized. Unambiguous confirmation of both structures were obtained approximately one year later, facilitated by the total syntheses of lycoxanthin and lycophyll reported by Kjøsen and Liaaen-Jensen in 1972. The original total synthesis was based on a C10+C20+C10 synthetic paradigm, in part due to the commercial availability of C20 dialdehyde (crocetindialdehyde). Up to the present, little additional chemical or biological information has accumulated in the primary literature for either compound.

Lycophyll was prepared by total synthesis at multiple gram scale for the current testing and derivatization to novel water-soluble, water-dispersible compounds. Isolation from natural sources demonstrates high cost, significant manpower, and generally low yields. Retrosynthetic analysis of the target xanthophyll revealed an efficient methodology utilizing at least some commercially available materials. In cases where commercial material was not available, these intermediates were synthesized in appropriate amounts. In some embodiments, commercially available materials may include geranyl acetate, a protected form of geraniol (C10), and/or crocetindialdehyde (C20). A method may include a total synthesis of acyclic carotenoids (e.g., lycophyll). In some embodiments, a synthesis of, for example, lycophyll may be realized in about 8 synthetic steps (Schemes III and IV). Synthetic steps may include an "endgame" double-Wittig olefination that successfully forms the target C40 scaffold while generating a mixture of geometric isomers (Scheme IV). The isomeric mixture may be deconvoluted to yield the target all-trans lycophyll. Deconvolution may include, but is not limited to, thermal or liquid chromatographic methods. The methodology shown in Schemes III and IV for synthesizing lycophyll may be used to synthesize other acyclic carotenoids, carotenoid derivatives, and carotenoid analogs.

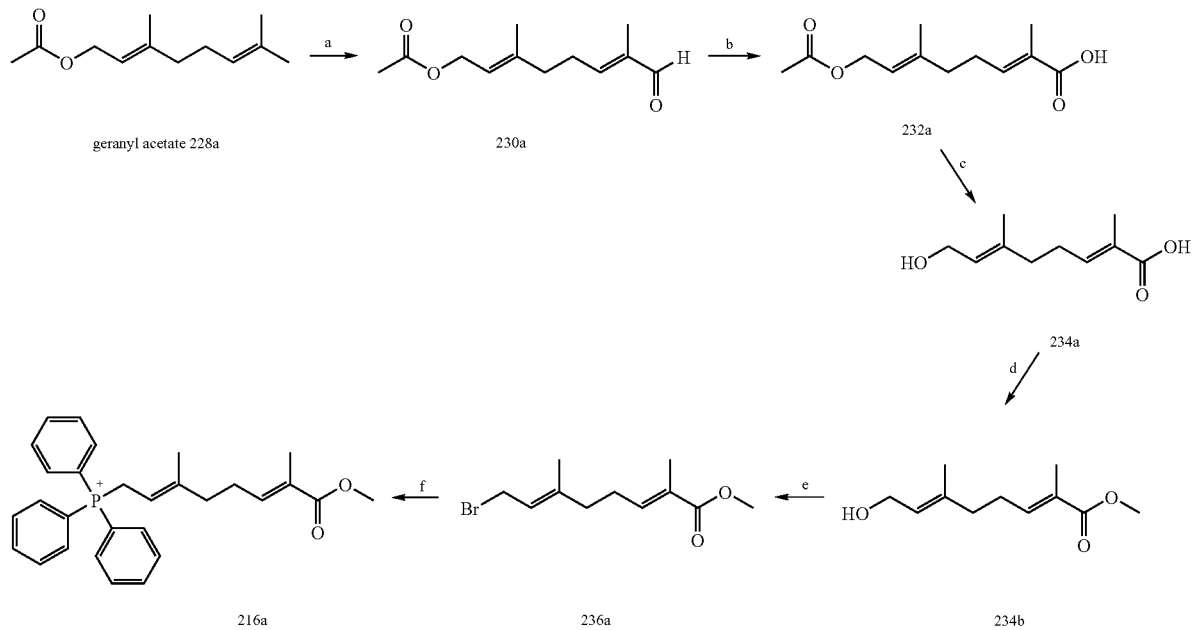

a. SeO$_2$, 95% EtOH;
b. NaClO$_2$, Na$_2$HPO$_4$, Me$_2$C=CHMe, t-BuOH/H$_2$O;
c. K$_2$CO$_3$, MeOH/H$_2$O;
d. CH$_3$I, K$_2$CO$_3$, DMF/H$_2$O;
e. CBr$_4$/Ph$_3$P, THF;
f. Ph$_3$P, EtOAc.

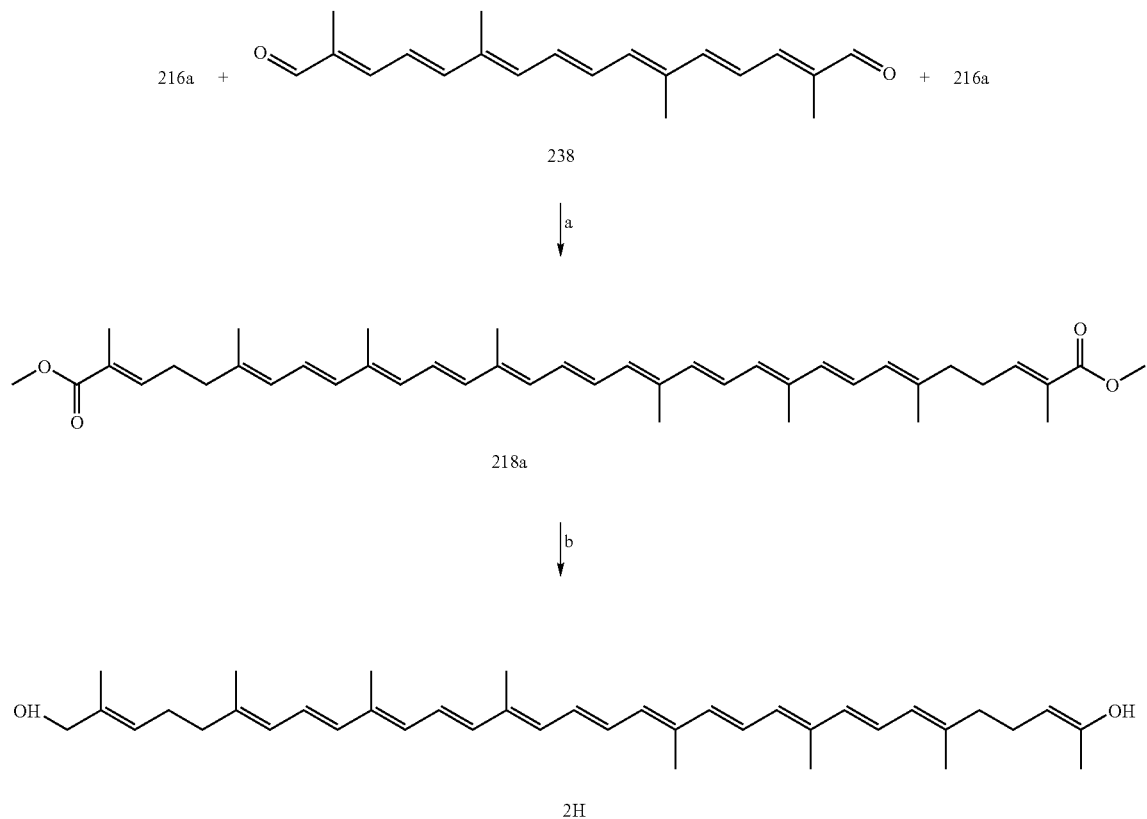

a. LiOMe in MeOH, toluene; b. DIBAL, THF.

Research has shown that targeted derivatization of carotenoids can successfully increase the aqueous solubility and/or dispersibility of the highly lipophilic natural scaffolds. These compounds have demonstrated beneficial effects as direct aqueous radical scavengers, as myocardial salvage agents in experimental infarction models, as agents ameliorating and/or preventing chronic liver injury, and/or as cancer chemopreventive agents. The derivatives have shown increased utility as parenteral agents in these settings, as well as improved oral bioavailability in model animal studies. Currently, our efforts have extended along these lines to include the derivatization of the rare xanthophyll lycophyll, specifically directed by principles of retrometabolic drug design. Acquisition of lycophyll through total synthesis (Scheme III and IV) facilitated the generation of water-dispersible lycophyll succinic and phosphoric diester salts (Scheme V). These novel compounds are readily dispersible in water without need of heat, detergents, co-solvents, or other additives. Such derivatives will likely find application in those indications in which parenteral delivery of highly-potent radical scavengers possessing the lycopene scaffold are necessary to achieve their intended purpose. Specifically, these compounds will be evaluated for efficacy in contemporary in vitro and in vivo cancer chemoprevention models, utilizing the natural tissue tropism of these compounds in mammals.

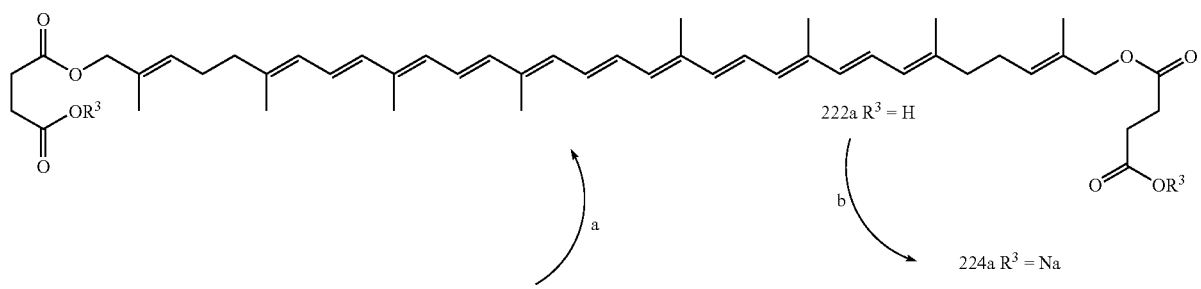

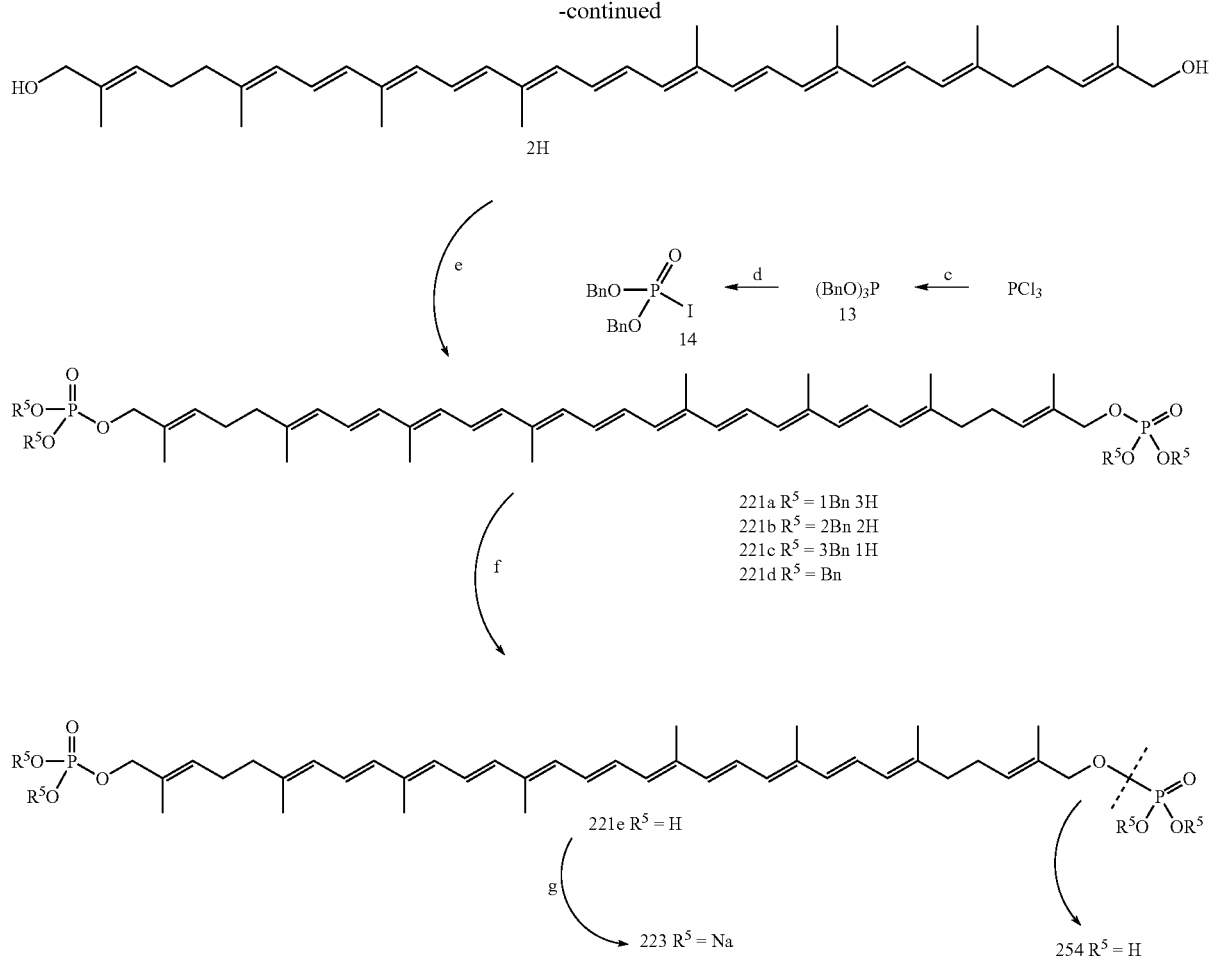

a. succinic anhydride, N,N-diisopropylethylamine, CH$_2$Cl$_2$;
b. NaOMe, CH$_2$Cl$_2$/MeOH (4/1);
c. benzyl alcohol, triethylamine, Et$_2$O;
d. I$_2$, CH$_2$Cl$_2$;
e. pyridine, CH$_2$Cl$_2$, then 14;
f. bromotrimethylsilane, N,O-bis(trimethylsilyl)acetamide, CH$_2$Cl$_2$ (254/222e (1/4)), then reverse-phase HPLC;
g. NaOMe, MeOH.

In some embodiments of a method to synthesize lycopene and its derivatives and/or analogs, a phosphonium salt product having the general structure

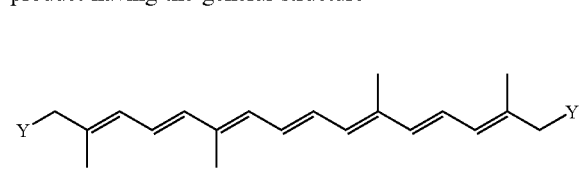

may be coupled with an aldehyde product having the general structure

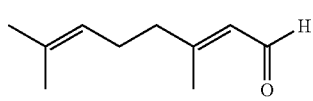

to form lycopene having the general structure

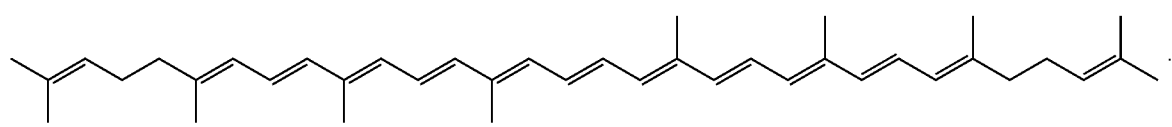

In some embodiments, Y may include —CH$_2$—PR$^5{}_3$ or —CH$_2$—P(=O)(OR$^5$)$_2$. R$^5$ may be alkyl or aryl.

In some embodiments, a lycopene analog or a lycopene derivative may include one or more substituents. At least one of the substituents may include hydrophilic substituents. In some embodiments, substituents may include chemically reactive substituents which serve as chemical intermediates.

In some embodiments, carotenoid chemical intermediates may be used to synthesize naturally occurring carotenoids such as xanthophylls. A method may include coupling a phosphonium salt product having the general structure

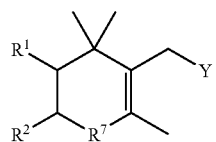

with a dialdehyde having the general structure

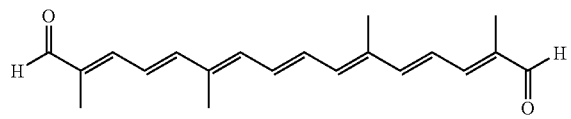

to form a carotenoid having the general structure

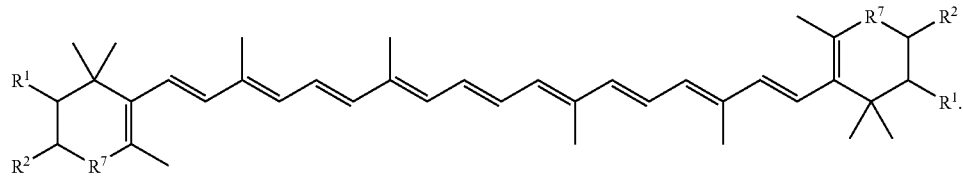

In some embodiments, R$^1$ and R$^2$ may be H or OR$^3$. R$^3$ may be SiR$^5{}_3$, H, alkyl, or aryl. R$^5$ may be alkyl or aryl. Y may include —CH$_2$—PR$^5{}_3$ or —CH$_2$—P(=O)(OR$^5$)$_2$. R$^7$ may include C—OR$^3$ or C=O. Examples of xanthophyll carotenoids than may be synthesized using this methodology include, but are not limited to, astaxanthin, lutein, zeaxanthin, and canthaxanthin.

In some embodiments, one or more of the conversions and/or reactions discussed herein may be carried out within one reaction vessel increasing the overall efficiency of the synthesis of the final product. In some embodiments, a product of one reaction during a total synthesis may not be isolated and/or purified before continuing on with the following reaction. A reaction may instead only partially be worked up. For example, solid impurities which fall out of solution during the course of a reaction may be filtered off and the filtrate washed with solvent to ensure all of the resulting product is washed through and collected. In such a case the resulting collected product still in solution may not be isolated, but may then be combined with another reagent and further transformed. In some cases multiple transformations may be carried out in a single reaction flask simply by adding reagents one at a time without working up intermediate products. These types of "shortcuts" will improve the overall efficiency of a synthesis, especially when dealing with large scale reactions (e.g., along the lines of pilot plant scale and/or plant scale).

An example of increasing the overall efficiency of a synthesis may include reducing the alkyne of compound 114 to an alkene forming compound 104. In some embodiments, zinc and an acid may be used to reduce the alkyne to an alkene. The acid may include, for example, glacial acetic acid. The resulting zinc acetate may then be filtered off, and the filter cake washed with an organic solvent (e.g., methylene chloride) to ensure collection of as much of the resulting product compound 104 as possible. The resulting product compound 104, still in solution, may then be added dropwise over a period of time (e.g., 30 minutes) to an aqueous solution of acid (e.g., HBr) and the resulting mixture stirred (e.g., for 10 minutes). The organic phase may be separated from the aqueous phase and triphenylphosphine added to the organic phase without isolating the previous product from solution. The addition of triphenylphosphine may result in compound 102. Dialdehyde compound 112 may be added to the resulting solution of compound 102 and cooled down (e.g., to about 0° C.). A base in solution may be added to the solution (e.g., sodium methoxide in methanol) dropwise. After stirring (e.g., about 5 hours), the solution may be finally fully worked up to acquire the purified isolated compound 104.

It has been stated that the compound of formula 100 embraces racemic and optically active and optically inactive stereoisomers. In some embodiments, a specific example of may include the synthesis of astaxanthin having a general formula of

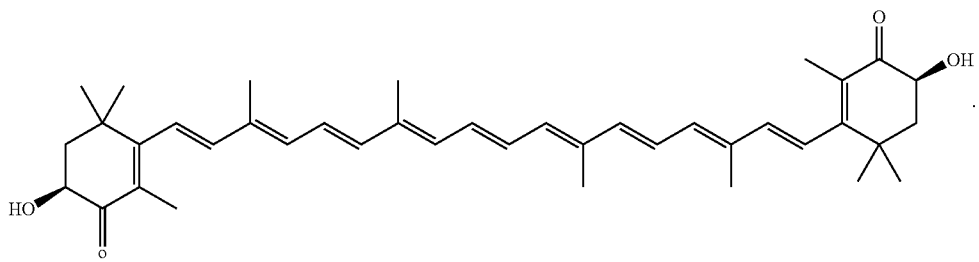

In an embodiment, carotenoid derivatives may be synthesized from naturally-occurring carotenoids. The carotenoids may include structures 2A–2F depicted in FIG. 1. In some embodiments, the carotenoid derivatives may be synthesized from a naturally-occurring carotenoid including one or more alcohol substituents. In other embodiments, the carotenoid derivatives may be synthesized from a derivative of a naturally-occurring carotenoid including one or more alcohol substituents. The synthesis may result in a single stereoisomer. The synthesis may result in a single geometric isomer of the carotenoid derivative. The synthesis/synthetic sequence may include any prior purification or isolation steps carried out on the parent carotenoid. Synthesis of carotenoid derivatives can be found in U.S. Published Patent Application Nos. 2004–0162329 and 2005–0113372, both of which are incorporated herein by reference.

EXAMPLES

Having now described the invention, the same will be more readily understood through reference to the following example(s), which are provided by way of illustration, and are not intended to be limiting of the present invention.

Example 1

Preparation of (R)4-hydroxyisophorone (R)-116

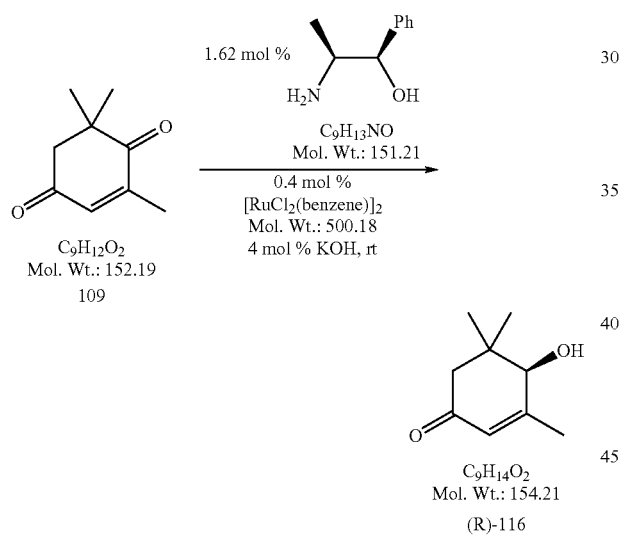

All solvents were free of $O_2$. And the reactions were done under $N_2$. Benzeneruthenium (II) dimer (19.72 g, 39.42 mmol, 0.4 mol %) and (1R, 2S)-(−)-norephedrine (99%) (24.14 g, 159.67 mmol, 1.62 mol %) were dissolved in a 12 L three-necked flask containing 2-propanol (7.5 L). After stirring the red solution for 45 min at 80° C., the heat was removed. It was transferred to a 50 L three-necked flask containing 2-propanol (28 L). 109 (1500 g, 9.86 mol) and 0.1 M potassium hydroxide in 2-propanol (3945 ml, 0.0395 mol, 4 mol %) were added. After 3 h (TLC showed the reaction was done), the red solution was filtered through a short silica gel pad and the filtrate was evaporated to dryness to obtain solids (about 1600 g). After five times recrystallization from $^iPr_2O$ (500 ml×5), 912 g of (R)-116 was obtained. The yield: 60%. $^1H$ NMR (CDCl$_3$, 300 MHz): δ 1.02 (s, 3H), 1.07 (s, 3H), 1.97 (s, 1H), 2.04 (t, J=1.2 Hz, 3H), 2.21 (d, J=16.3 Hz, 1H), 2.39 (d, J=16.4 Hz, 1H), 4.03 (d, J=6.6 Hz, 1H), 5.86 (br s, 1H). $^{13}C$ NMR (CDCl$_3$, 75 MHz): δ 21.22, 21.46, 26.89, 38.48, 48.97, 76.89, 126.29, 160.81, 198.79. $[α]_D^{23}$+105.34 (c=1.006, MeOH), literature $[α]_D^{22}$+105.9 (c=1.00, MeOH).

Example 2

Preparation of (1R,4S)-2,6,6-trimethyl-2-cyclohexen-1,4-diol (1R,4S)-118

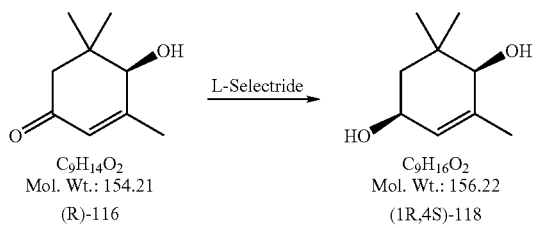

To a solution of L-Selectride (5674 mL, 1 M in THF, 1.25 equiv), a solution of compound (R)-116 (700 g, 4.54 mol, 1 equiv) in THF (3000 mL) was added dropwise at −78° C. After stirring for 1.5 h, the mixture was sequentially treated with $H_2O$ (600 mL), 4N NaOH (1450 mL). After extractions with AcOEt (500 ml×5) and the combined organic phase was dried and concentrated. To the residue was charged 3000 mL of hexanes, then the mixture was filtered. The solid was washed with hexanes (200 mL×3). The solid crude product was purified by flash chromatography using Hexanes/AcOEt (3/1) as an eluent. 645 g of compound (1R, 4S)-118 was obtained (yield: 91%). Recrystallized from 1000 ml of EtOAc to obtain 504 g (70%) of (1R, 4S)-118. $^1H$ NMR (CDCl$_3$, 500 MHz): δ 0.86 (s, 3H), 1.02 (s, 3H), 1.45 (dd, J=12.8, 9.5 Hz, 1H), 1.67 (ddt, J=12.8, 6.3, 1.1 Hz, 1H), 1.84 (t, J=1.7 Hz, 3H), 3.34 (s, 1H), 4.18 (m, 1H), 5.54 (br s, 1H). $[α]_D^{23}$+68.63 (c=1.6000, CHCl$_3$), literature $[α]_D^{24}$+67.4 (c=0.27, CHCl$_3$).

Example 3

Preparation of (1R,4S)4-tert-Butyidimethylsilyloxy-2,6,6-trimethyl-2-cyclohexen-1-ol (1R,4S)-120a

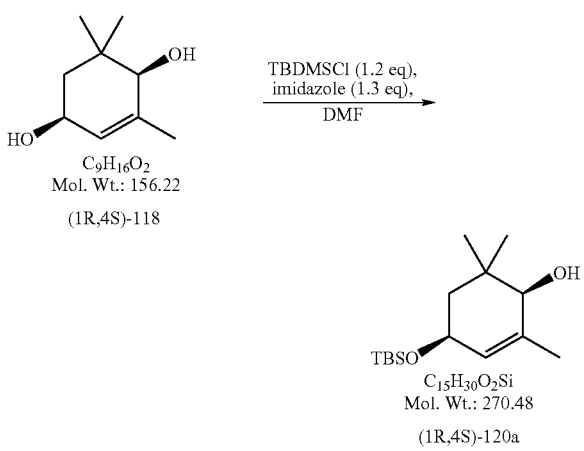

A mixture of enantiomerically pure (1R, 4S)-118 (1000 g, 6.40 mol), TBDMSCl (1194 g, 7.68 mol, 1.2 eq) and imidazole (566.37 g, 8.32 mol, 1.3 eq) in DMF (9 L) was stirred at room temperature for 1 hr and 20 min. Water (2 L) was added, aqueous phase was extracted with diethyl ether (2000 ml×3). The combined organic layer was dried over $Na_2SO_4$. After concentration, the crude product (1R, 4S)-120a was subjects to next step without further purification.

Example 4

Preparation of (S)-4-tert-Butyidimethylsilyloxy-2-cyclohexenone (S)-108b

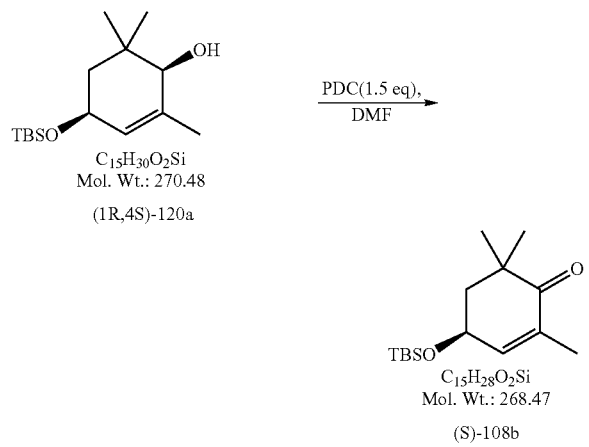

(1R, 4S)-120a (~6.40 mol) was added to a mixture of PDC (3613 g, 1.5 eq) and DMF (8000 ml), which was cooled by ice-water. And then, the mixture was stirred for 1 h and 10 min at rt. Ether (8 L) was added. The mixture was passed through a pad of celite. Then solution was washed with water (3 L×2). The organic phase was dried over $Na_2SO_4$. 1718.2 g of(S)-108b (Yield: 100%, two steps from 118 to 108b) was obtained after column chromatography (hexanes/ethyl acetate, 50/1~30/1). $^1$H NMR ($CDCl_3$, 500 MHz): δ 0.12 (s, 3H), 0.13 (s, 3H), 0.92 (s, 9H), 1.11 (s, 3H), 1.14 (s, 3H), 1.78 (brs, 3H), 1.87 (dd, J=12.9, 9.8 Hz, 1H), 1.99 (ddd, J=12.9, 5.4, 1.8 Hz, 1H), 4.55 (m, 1H), 6.50 (br s, 1H).

Example 5

Determine the ee Value of Compound (S)-108b

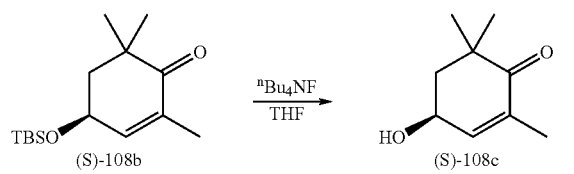

To a solution of compound 108b (40 g, 112 mmol) in THF (450 ml), $^nBu_4NF$ (29.22 g, 112 mmol in 150 ml of THF was added. After 30 min, 200 ml of water and 500 ml of EtOAc was added. The organic phase was then washed with a half-saturated brine (400 ml×2) and brine (400 mL). It was dried and concentrated and subjected to column chromatography (hexane/ethyl acetate, 5/1) to give 20.25 g of (S)-108c (92%). $[α]_D^{23}$ −48.0 (c=1.98, EtOH), literature $[α]_D^{20}$ -46.7 (c=1.0, EtOH). The racemic 108c was separated using a chiral HPLC column; baseline separation was not achieved. Reverse phase HPLC column, Pirkle covalent, (S, S) Whelk-O 1, spherical silica; Eluent, 3:97 2-propanol:hexane, 1 ml/min. For racemic 108c, $t_1$=14.07 min, $t_2$=14.67 min. Only one peak was detected for (S)-108c using the same HPLC condition $T_s$(108c)=14.74 min.

Example 6

Preparation of Compounds 112a

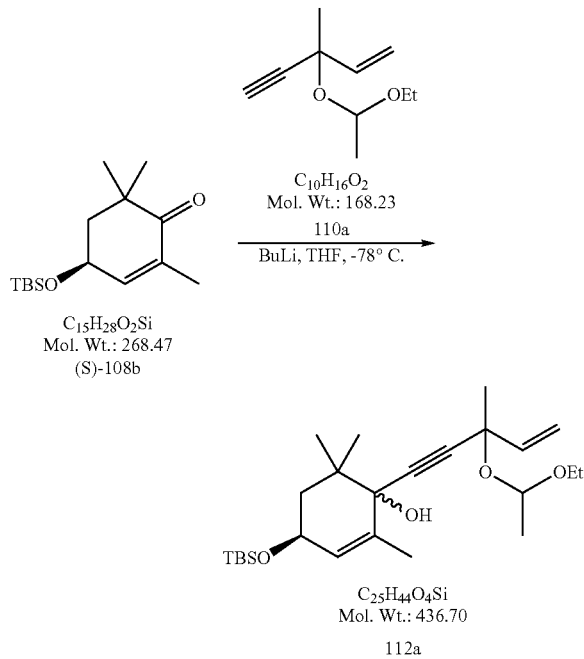

A mixture of alkyne 110a (689.3 g, 4.10 mol, 1.1 eq) and THF (13 L) was cooled to −78° C., BuLi (1640 mL, 2.5 M, 4.10 mL, 1.1 eq) was added dropwise. After 2 h, compound (S)-108b (1000 g, 3.725 mol) in 2 L of THF was added dropwise. In the 4 hrs, the temperature was allowed to raise from −78° C. to −25° C. $NH_4Cl$ saturated solution (500 mL) and brine (500 mL) was added and extracted with EtOAc (3000 mL×1). Dried. After concentration, the crude product 112a (~1770 g) was subjected to next step without further purification.

Example 7

Preparation of Compounds 114a

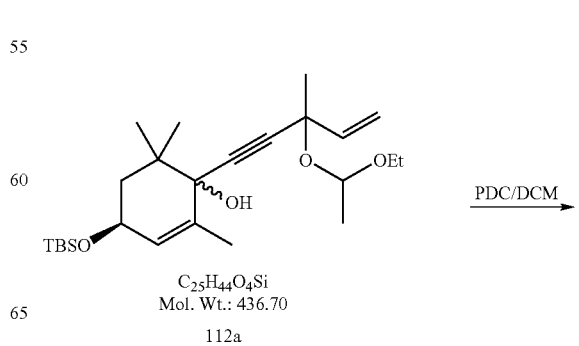

-continued

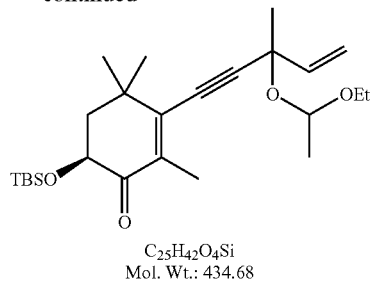

C$_{25}$H$_{42}$O$_4$Si
Mol. Wt.: 434.68
114a

A solution of compounds 112a (~3.75 mol) in DCM (2 L) was added dropwise to a mixture of PDC (2101.86 g, 5.58 mol, 1.5 eq), NaOAc (458.16 g, 5.58 mol, 1.5 eq), 4 Å MS (1000 g) and DCM (10 L). After 24 h, ethyl acetate (2000 ml) was added and it was subjected to a short silica gel pad and washed with ethyl acetate. After concentration, the crude product 114a (1710 g) was subjects to next step without further purification. $^1$H NMR (CDCl$_3$, 300 MHz): δ 0.44 (s, 3H), 0.13 (s, 3H), 0.87 (s, 9H), 1.12 (td, J=6.9, 2.7 Hz, ~3H), 1.21–1.32 (m, ~10H), 1.59 (s, ~1.5H), 1.62 (s, ~1.5H), 1.83–2.2 (m, ~4H), 3.32–3.70 (m, ~2H), 4.29 (dd, J=11.1, 6.9 Hz, 1H), 4.87 (q, J=5.4 Hz, ~0.5H), 4.95 (q, J=5.4 Hz, ~0.5H), 5.18 (d, J=9.9 Hz, 1H), 5.49 (dd, J=17.4, 9.9 Hz, 1H), 5.83 (dd, J=17.1, 10.2 Hz, 0.5H), 5.95 (dd, J=17.1, 10.2 Hz, ~0.5H). [α]$_D^{26}$-106.13 (c=1.446, 1,4-dioxane)

Example 8

Preparation of Compounds 114b

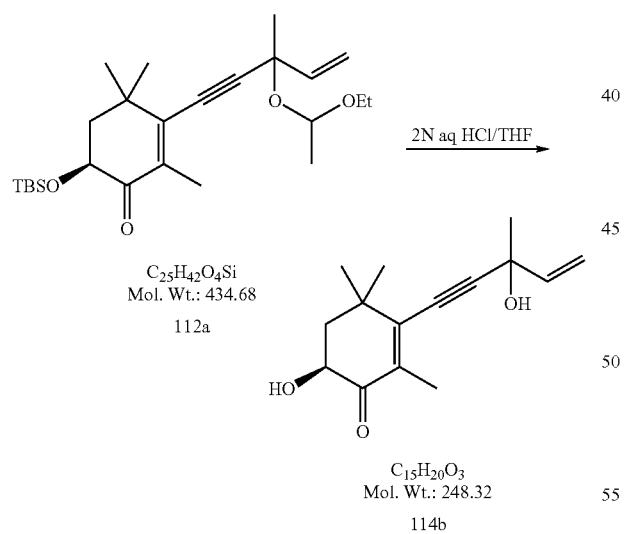

To a solution of compound 114a (1000 g, 2.303 mol) in 6000 mL of THF, was added 1450 ml of aq HCl (450 mL of con. HCl diluted with 1000 mL of water). The mixture was stirred for 4 hrs, sodium chloride (300 g) and 3 L of ethyl acetate were added. Organic phase was separated and washed with water (2000 mL×1), the mix solution of saturated NaHCO$_3$ solution (2000 mL) and brine (2000 mL). Combined aqueous phase was extracted with ethyl ether (20000 mL×1). Washed with water (500 ml), brine (500 ml). Dried. 980 g of compound 114b was obtained after column chromatography (hexanes/ethyl acetate, 100/0 to 1/1). The yield was 57% (three steps, from 108b to 114b). $^1$H NMR (CDCl$_3$, 300 MHz): δ 1.27 (s, 3H), 1.32 (s, 3H), 1.64 (s, 3H), 1.77 (t, J=13.8 Hz, 1H), 1.97 (s, 3H), 2.19 (dd, J=12.9, 6.0 Hz, 1H), 2.51 (br s, 3H), 3.62 (br s, 1H), 4.31 (dd, J=13.5, 5.4 Hz, 1H), 5.18 (d, J=10.2 Hz, 1H), 5.51 (br d, J=17.1 Hz, 1H), 6.02 (br dd, J=17.1, 10.2 Hz, 1H).

Example 9

Preparation of Phosphonium Salt (S)-102a from Alkynediol 114b

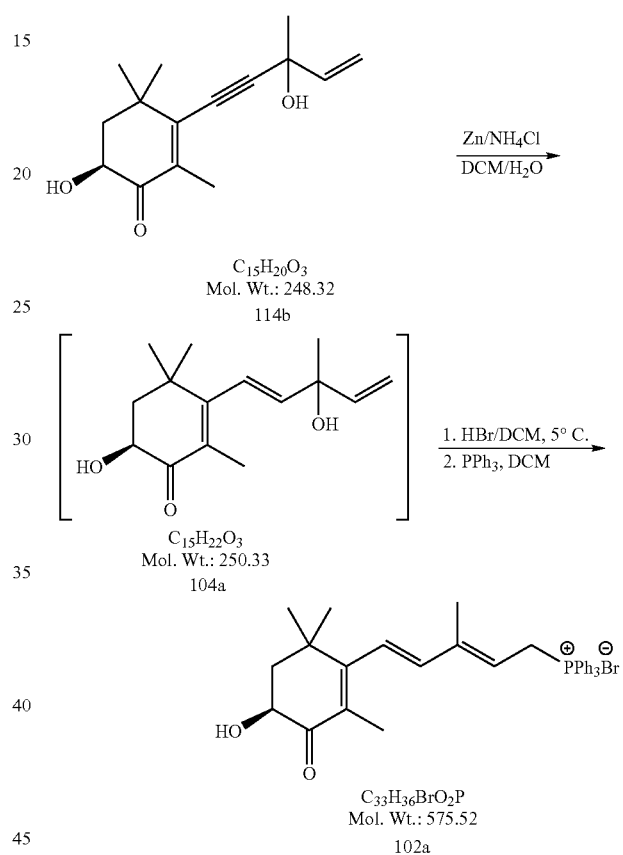

650 g of alkynediol 114b (2.62 mol) was added to a mixture of 4300 mL of methylene chloride and 4300 mL of H$_2$O. After cooling to 0° C., NH$_4$Cl (280.07 g, 5.24 mol, 2 eq) and Zn (256.67 g, 3.93 mol, 1.5 eq) was added. Then the reaction mixture was stirred for 3.5 h at 0~5° C. and the reaction was checked with HPLC. The mixture was filtered through a pad of celite, washed with DCM (500 ml×5). The organic phase was dried. To this solution, 387.6 mL of 48% aqueous HBr (3.4 mol, 1.3 eq) was added in two portions at −8° C. After 30 min, the reaction temperature was raised to −2° C. Water (1000 ml) was run in, and the organic phase was separated off. The organic phase was washed with water (1000 ml×3). To the organic solution was added 23 mL of 1,2-epoxybutane. While cooling to ~10° C., 755.3 g (2.88 mol, 1.1 eq) of triphenylphosphine was added. After PPh$_3$ was dissolved, another 23 mL of 1,2-epoxybutane was added and the mixture was stirred at rt for 3.5 h. Concentrated and $^t$BuOMe (1500 mL) was added to precipitate the phosphonium salt. The solids were filtered and washed with $^t$BuOMe (100 ml×2). 1000 g of 102a (66%, three steps from 114b to 102a) was obtained.

Example 10

Preparation of (3S,3'S)-all-E-astaxanthin

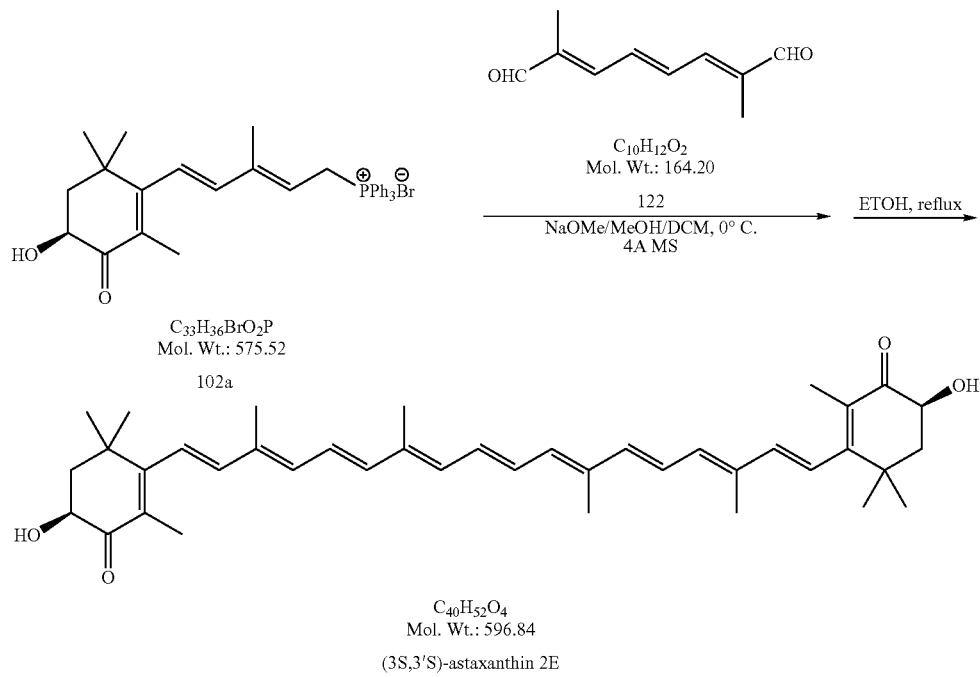

To a mixture of phosphonium salt (S)-102a (463 g, 0.804 mol, 2.2 eq), 4 Å MS (100 g) and $C_{10}$-dialdehyde (2,7-dimethyl-2,4,6-octatrienedial 122) (60 g, 0.365 mol, 1 eq) in DCM (7 L) at 0° C., MeONa in MeOH (30 wt %, 151 mL, 0.804 mol, 2.2 eq) was added dropwise. After 4 h, the additional 42 g of phosphonium salt (S)-102a (42 g, 0.2 mol) and 14 mL of MeONa in MeOH (30 wt %, 0.2 mol) was added. After 21 h, the mixture was filtered through a silica gel pad (eluents: DCM/EtOAc ~DCM/MeOH). Concentrated and filtered to obtain 110 g of crude product. The crude product (297 g) was mixed with 1000 ml of ethyl alcohol refluxed for 3 h. After cooling, filtered and washed with ethyl alcohol (50 ml×2) to obtain 221 g of (3S, 3'S)-all-E-astaxanthin. $^1$H NMR (CDCl$_3$, 300 MHz): δ 1.21 (s, 6H), 1.32 (s, 6H), 1.81 (t, J=13.2 Hz, 2H), 1.94 (s, 6H), 1.99 (s, 6H) and 2.00 (s, 6H), 2.15 (dd, J=12.6, 5.7 Hz, 2H), 4.32 (dd, J=13.8, 5.7 Hz, 2H), 6.18–6.72 (m, ~14H).

Example 11

Preparation of Compounds 110a

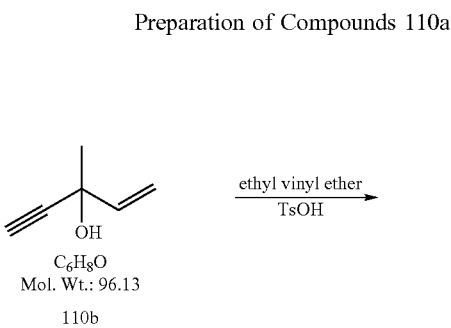

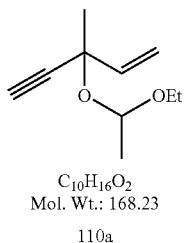

Ethyl vinyl ether (788 mL) was cooled to 5° C. and treated with PTSA (450 mg) followed by the slow addition of compound 110b (freshly distilled, 450 g, 4.68 mol). After the addition was done, the reaction mixture was kept at rt for 3 h, quenched with triethylamine (3 mL), and then distilled to yield acetal 110a (770 g, 97.8%). Bp: ~80° C./20 mmHg.

Example 12

Preparation of 2-(Triphenylphosphanylidene)-propionic acid ethyl ester

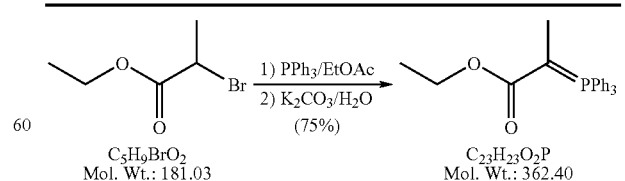

| Raw Materials | FW | Quantity Used | Moles |
|---|---|---|---|
| Ethyl 2-bromopropionate | 181.03 | 1.0 Kg | 5.52 mol |
| Triphenyl Phosphine | 262.29 | 1.6 Kg | 6.10 mol |

-continued

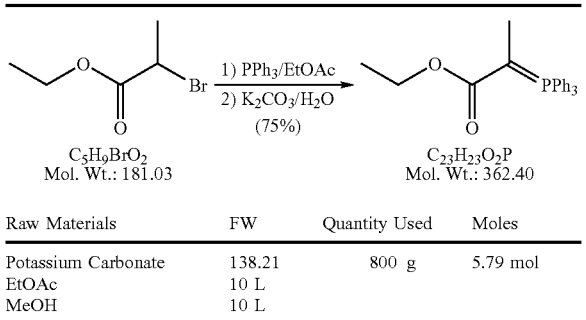

| Raw Materials | FW | Quantity Used | Moles |
|---|---|---|---|
| Potassium Carbonate | 138.21 | 800 g | 5.79 mol |
| EtOAc | 10 L | | |
| MeOH | 10 L | | |

1.6 Kg (6.10 mol) triphenyl phosphine was dissolved in 10 L ethyl acetate and 1.0 Kg of ethyl 2-bromopropionate was added into the above solution. The reaction mixture was stirred at room temperature for 2 days. White solid was filtered off and the precipitate was washed with ethyl acetate. The resulting compound was dissolved in methanol and treated with saturated aqueous potassium carbonate. After stirring for 2 h, the yellow solid was filtered off and washed with water to give 1.5 Kg (75%) of desired product.

Example 13

Preparation of 4-Hydroxy-2-methyl-but-2-enoic acid ethyl ester

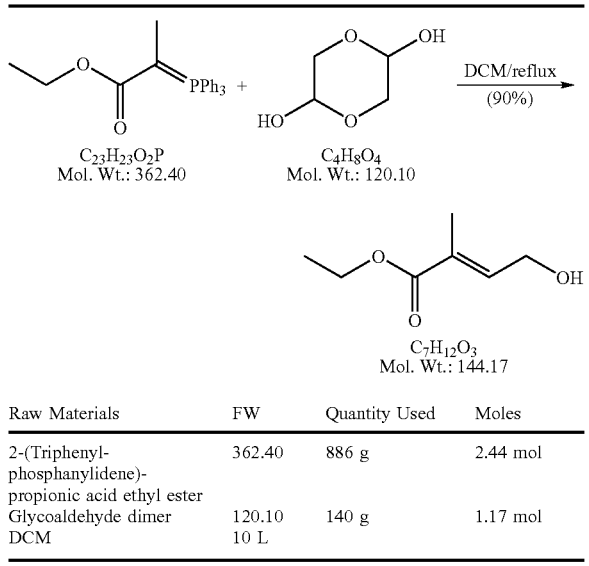

| Raw Materials | FW | Quantity Used | Moles |
|---|---|---|---|
| 2-(Triphenyl-phosphanylidene)-propionic acid ethyl ester | 362.40 | 886 g | 2.44 mol |
| Glycoaldehyde dimer | 120.10 | 140 g | 1.17 mol |
| DCM | 10 L | | |

886 g (2.44 mol) of 2-(triphenyl-phosphanylidene)-propionic acid ethyl ester in methylene chloride (4 L) was added dropwise into a refluxing solution of glycoaldehyde dimer (140 g, 1.17 mol) in methylene chloride (6 L). After refluxing for 4 h, the solvent was evaporated. Resulting crude product was fractionated (bp 108–114° C. at 2 mmHg) to give 304 g (90%) pure product as an oil. $^1$H-NMR (300 Hz CDCl$_3$) δ 6.88 (t, 1H, CH), 4.35 (d, 2H, CH$_2$OH), 4.20 (q, 2H, OCH$_2$), 1.85 (s, 3H, CH$_3$), 1.30 (t, 3H, CH$_3$).

Note: This process was repeated and 660 g title compound was collected.

Example 14

Preparation of 4-Bromo-2-methyl-but-2-enoic acid ethyl ester

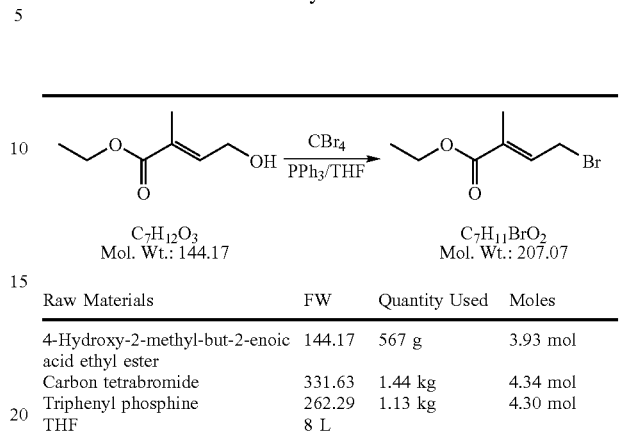

| Raw Materials | FW | Quantity Used | Moles |
|---|---|---|---|
| 4-Hydroxy-2-methyl-but-2-enoic acid ethyl ester | 144.17 | 567 g | 3.93 mol |
| Carbon tetrabromide | 331.63 | 1.44 kg | 4.34 mol |
| Triphenyl phosphine | 262.29 | 1.13 kg | 4.30 mol |
| THF | 8 L | | |

To a cooled solution (0° C.) of 4-hydroxy-2-methyl-but-2-enoic acid ethyl ester (567 g, 3.93 mol) in THF (8L) was added carbon tetrabromide followed by triphenyl phosphine. The reaction mixture was slowly warmed to room temperature and stirred overnight. White solid (identified as compound 6) was isolated by filtering. The filtration was condensed and added ether, the resulting white precipitated (identified as triphenyl phosphate and triphenyl phosphine) was filtered off and discarded. Ether was evaporated and the resulting crude product was used without further purification in the next step.

Note: This process was repeated until 660 g of 4-hydroxy-2-methyl-but-2-enoic acid ethyl ester was consumed.

Example 15

Preparation of 2-Methyl-4-(triphenyl-phosphanyl)-but-2-enoic acid ethyl ester bromide salt

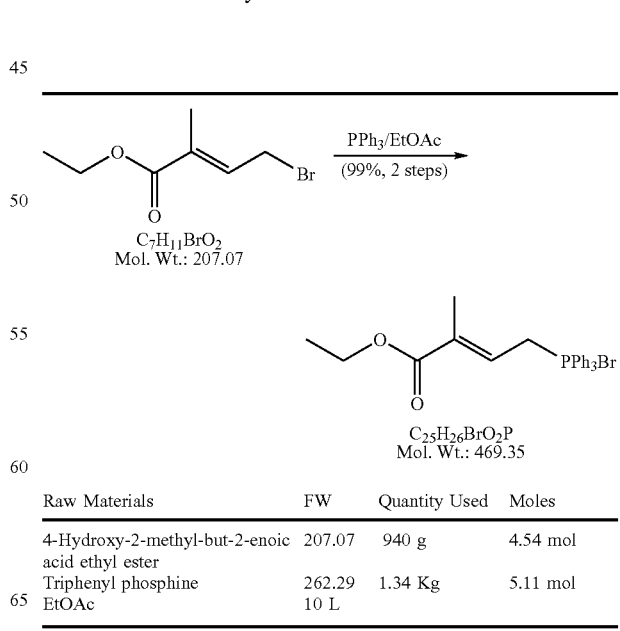

| Raw Materials | FW | Quantity Used | Moles |
|---|---|---|---|
| 4-Hydroxy-2-methyl-but-2-enoic acid ethyl ester | 207.07 | 940 g | 4.54 mol |
| Triphenyl phosphine | 262.29 | 1.34 Kg | 5.11 mol |
| EtOAc | 10 L | | |

940 g (4.54 mol) of 4-hydroxy-2-methyl-but-2-enoic acid ethyl ester was added into the solution of triphenyl phosphine (1.34 Kg, 5.11 mol) in 10 L ethyl acetate. The reaction mixture was stirred at room temperature for 2 days. The resulting white precipitate was filtered and washed with ethyl acetate to give 2.11 kg (99%) of the 5 title compound. $^1$H-NMR (300 Hz DMSO-$d_6$) δ 7.78–7.95 (m, 15H, ArH), 6.40 (q, 1H, CH), 4.76 (q, 2H, $CH_2P$), 4.10 (q, 2H, $CH_2$), 1.60 (d, 3H, $CH_3$), 1.15 (t, 3H, $CH_3$).

Note: This process was repeated and 4.2 Kg title compound was collected

Example 16

Preparation of 2,6,11,15-Tetramethyl-hexadeca-2,4,6,8,10,12,14-heptaenedioic acid diethyl ester

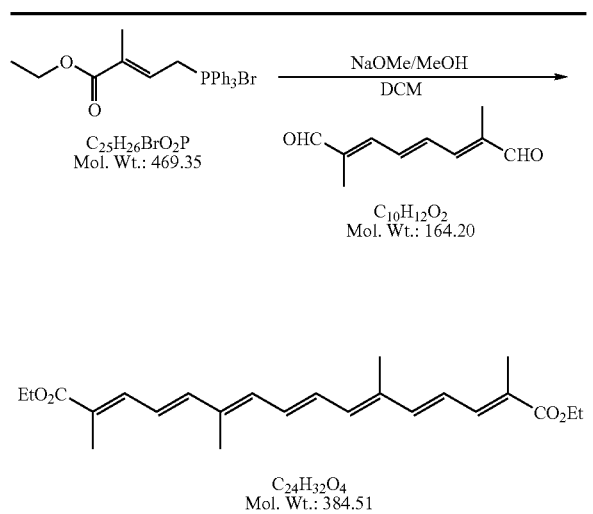

| Raw Materials | FW | Quantity Used | Moles |
|---|---|---|---|
| 2-Methyl-4-(triphenyl-phosphanyl)-but-2-enoic acid ethyl ester bromide salt | 469.35 | 2006.6 g | 4.28 mol |
| 2,7-Dimethyl-octa-2,4,6-trienedial | 164.20 | 234 g | 1.43 mol |
| NaOMe/MeOH (30%) | 54.02 | 749 mL | 4.00 mol |
| Methylene chloride | | 5 L | |

To a refluxing solution of 2-Methyl-4-(triphenyl-phosphanyl)-but-2-enoic acid ethyl ester bromide salt (2006.6 g, 4.28 mol) and 2,7-Dimethyl-octa-2,4,6-trienedial (234 g, 1.43 mol) in DCM (5 L) was added dropwise a solution of 30% by wt. NaOMe (749 mL, 4.00 mol) in methanol. The reaction mixture was refluxed for 3 hrs. The mixture was pushed through a short column of silica and the solvent was reduced in vacuo. The residue was redissolved in EtOH (3 L) and heated to reflux for 3 hrs. Cooled and filtered. The solid was washed with MeOH (100 mL×3) then diethyl ether (100 mL) and dried to give 250 g of orange powder (45%) $^1$H NMR (300 Hz, $CDCl_3$) δ 7.28 (s, 1H, CH), 7.26 (s, 1H, CH), 6.60 (m, 8H, CH), 4.23 (q, 4H, $CH_2$), 1.98 (s, 6H, $CH_3$), 1.53 (s, 6H, $CH_3$), 1.25 (t, 6H, $CH_3$).

Example 17

Preparation of 2,6,11,15-Tetramethyl-hexadeca-2,4,6,8,10,12,14-heptaene-1,16-diol

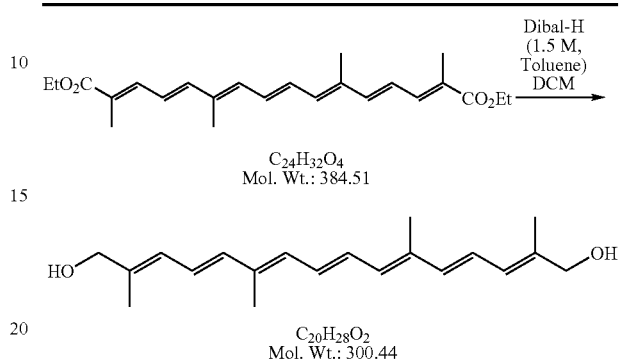

| Raw Materials | FW | Quantity Used | Moles |
|---|---|---|---|
| 2,6,11,15-Tetramethyl-hexadeca-2,4,6,8,10,12,14-heptaenedioic acid diethyl ester | 384.51 | 200 g | 0.52 mol |
| Methylene chloride | | 3000 mL | |
| Diisobutylaluminum hydride (1.5 M, Toluene) | 142.22 | 1533 mL | 2.30 mol |

To a solution of 2,6,11,15-tetramethyl-hexadeca-2,4,6,8,10,12,14-heptaenedioic acid diethyl ester (200 g, 0.52 mol) in 3000 mL of DCM was added dropwise a solution of diisobutylaluminum hydride in toluene (1.5 M, 1533 mL, 2.30 mol) at −78° C. The mixture was stirring at 0° C. for 2 h. 100 mL of water was added the 200 ml of 2N NaOH was added to quench the reaction. The suspension was filtered off and solid was washed by a large amount of THF. The combined organic layer were dried over $Na_2SO_4$ and evaporated to give 133.16 g (85%) brown solid. $^1$H NMR (300 Hz, $CDCl_3$) δ 6.41 (m, 10H, CH), 4.16 (s, 4H, $CH_2$), 1.95 (m, 12H, $CH_3$).

Example 18

Preparation of 2,6,11,15-Tetramethyl-hexadeca-2,4,6,8,10,12,14-heptaenedial

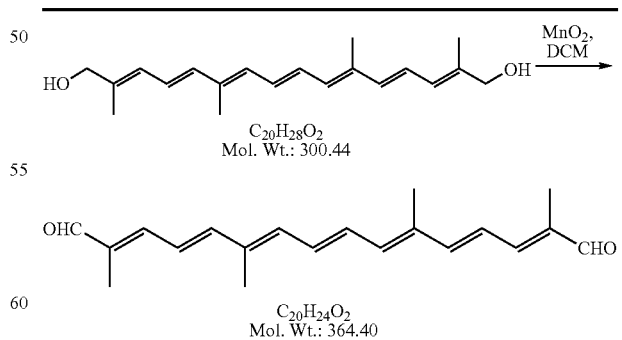

| Raw Materials | FW | Quantity Used | Moles |
|---|---|---|---|
| 2,6,11,15-Tetramethyl-hexadeca-2,4,6,8,10,12,14-heptaene-1,16-diol | 300.44 | 50 g | 0.166 mol |

-continued

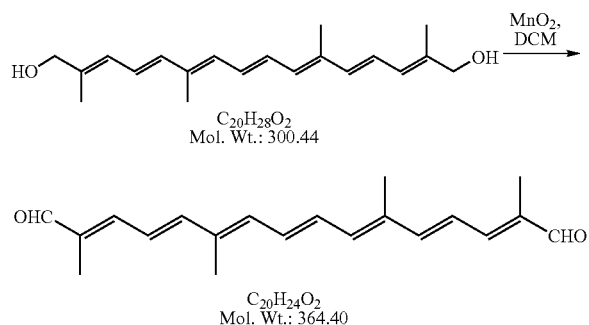

| Raw Materials | FW | Quantity Used | Moles |
|---|---|---|---|
| Manganese dioxide | 86.94 | 500 g | 5.75 mol |
| Methylene chloride | | 3000 L | |

To a suspension of 2,6,11,15-tetramethyl-hexadeca-2,4,6,8,10,12,14-heptaene-1,16-diol (50 g, 0.166 mol) in 3000 mL of DCM was added portionwise manganese dioxide (500 g, 5.75 mol) at room temperature. The mixture 15 was After heated to reflux for 2 h, the solid was filtered via celite and washed with $CH_2Cl_2$. The solvent was removed under reduced pressure to give 36 g of pure product (73%). $^1$H-NMR (300 Hz DMSO-$d_6$) δ 9.42 (s, 2H, CHO), 7.18 (s, 1H, CH), 7.16 (s, 1H, CH), 6.93 (m, 6H, CH), 2.01 (s, 6H, $CH_3$), 1.82 (s, 6H, $CH_3$).

Example 19

Preparation of (S)-(−)-4-Hydroxy-3-methoxy-2,6,6-trimethyl-cyclohex-2-enone

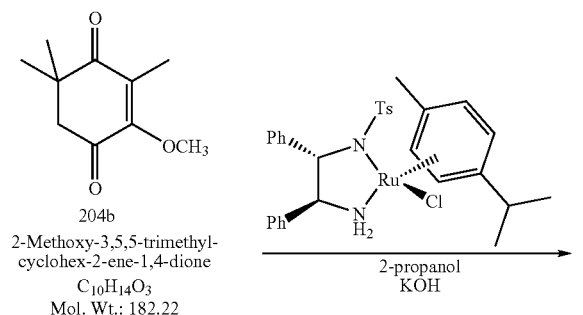

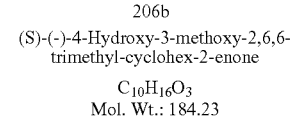

To a solution of (1S,2S)-N-p-toluenesulfonyl-1,2-diphenylethylenediamine (26.8 mg, 0.073 mmol) in Argon sparged 2-propanol (10 mL) was added dichloro(p-cymene) ruthenium(II)dimer (11.2 mg, 0.018 mmol). The suspension was heated to 80° C. for 30 min during which time the solids went into solution. The reaction was cooled to room temperature, a solution of 204b (670 mg, 3.67 mmol) in degassed 2-propanol (15 mL) was added followed by 0.1 M KOH in 2-propanol (1.8 mL) and then stirred overnight. TLC analysis (1:1 ethyl acetate:hexanes) showed the reaction was complete so the reaction was neutralized with aq. citric acid, filtered through a small pad of silica gel and then concentrated under vacuum. Purification by column chromatography (silica gel, 20:80 ethyl acetate:hexanes to 40:60 ethyl acetate:hexanes over 30 min) provided compound 206b (589 mg, 87%) as a waxy solid.

Example 20

Preparation of (S)-2,2,4,6,6-Pentamethyl-7,7a-dihydro-6H-benzo[1,3]dioxol-5-one

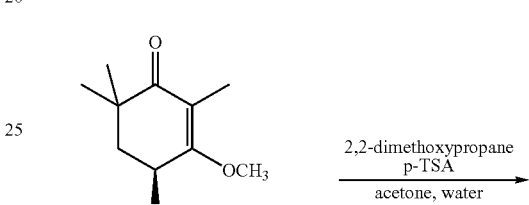

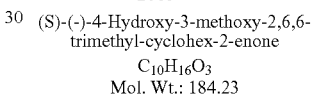

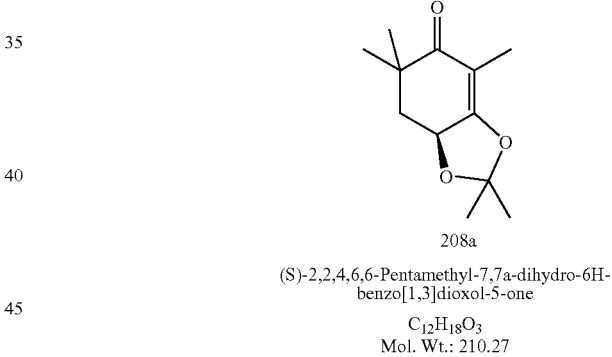

Compound 206b (587 mg, 3.18 mmol) was dissolved in acetone (5 mL), 2,2-dimethoxypropane (10 mL) and water (0.15 mL). p-Toluenesulfonic acid monohydrate (30 mg, 0.157 mmol) was added and the reaction was heated to reflux. After one hour the reaction had only gone 10% so more water (0.15 mL) was added and the reflux was continued. The reaction was monitored every hour and more water (0.15 mL) was added until a total of 0.75 mL had been added. At this point the reaction was cooled and allowed to stir over night. The next morning all the enol ether had been hydrolyzed so the reaction was heated to reflux for 1 hour to form the acetonide then cooled and quenched with saturated aq. sodium bicarbonate (0.2 mL). The volatile solvents were removed under reduced pressure then the reaction was partitioned between ethyl acetate and water then extracted with ethyl acetate, dried over sodium sulfate, filtered and concentrated under vacuum. Purification by column chromatography (silica gel, 15:85 ethyl acetate:hexanes to 25:75 ethyl acetate:hexanes over 20 column volumes) provided compound 208a (537 mg, 80%) as an oil. $^1$H NMR (CDCl$_3$) δ 4.88 (m, 1H), 2.20 (dd, J=11.5 Hz, J=5.5 Hz, 1H), 1.85 (dd, J=11.5 Hz, J=11.5 Hz, 1H), 1.69 (s, 3H), 1.63 (s, 3H), 1.56 (s, 3H), 1.19 (s, 3H), 1.16 (s, 3H); ESI, m/z 211 [M+H]$^+$, 98.2% ee by HPLC.

HPLC conditions:

Chiral method

Mobile Phase 95:5 heptane:2-propanol

Column: CHIPALCEL OD column, 4.6 mm×250 mm, 10 um. Part #14625

Flow: 1 mL/min

Detection: UV@254 nm

Example 21

Preparation of Epoxyketoisophorone

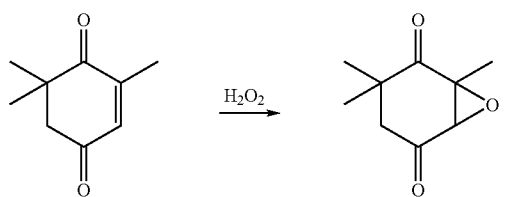

A buffer may be substituted for the controlled base feed and the pH controller as described here. To a 500 ml 3-neck Morton flask fitted with a bottom outlet, an addition funnel, a magnetic stirrer and a thermometer were charged 30 g 5 wt % aqueous sodium bicarbonate, 30 g 5 wt. % aqueous sodium carbonate, and 20 g keto-isophorone (0.132 mole). To the stirred mixture was added dropwise over one hour while maintaining the temperature between 20 and 25° C. with water-ice bath cooling 15 g 35% hydrogen peroxide (0.165 mole) and the mixture stirred an additional three hours. TLC (e.g., ethyl acetate; heptane 30:70 v/v, silica, iodine visualization, ketoisophorone Rf 0.70, epoxyketoisophorone Rf 0.77) showed complete conversion. The mixture was allowed to separate, the organic phase retained and the aqueous extracted three times, each time with 100 ml dichloromethane. The combined organic and dichloromethane phases were then washed with 50 ml 5 wt % sodium bisulfite solution then with 50 ml 20 wt % sodium chloride solution and the solution dried over anhydrous sodium sulfate. The filtered solution was then concentrated in vacuo on a rotovac to furnish 19.7 g epoxyketoisophorone. Yield is estimated at 89%. NMR of this product showed it to be >95% pure. 1H NMR: 1.08 (s, 3H), 1.3 (s, 3H), 1.55 (s, 3H), 2.26 (d, j=17, 1H), 3.05 (d, j=17, 1H), 3.52 (s, 1H).

Example 22

Preparation of 3-Hydroxyketoisophorone

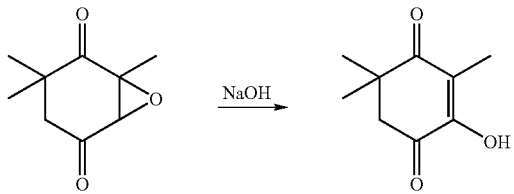

The epoxyketoisophorone product was converted to 3-hydroxyketoisophrone. To a 500 ml round bottom flask equipped with an addition funnel, a thermometer, and a magnetic stirrer were charged 30 ml water and 19.6 g epoxyketoisophorone and the mixture stirred while adding dropwise over one hour 18 ml 28 wt % sodium hydroxide solution while keeping the temperature between 30 and 35° C. with a water ice cooling bath. The yellow mixture was stirred another two hours, cooled to room temperature then acidified by dropwise addition to pH I with 37% hydrochloric acid during which a solid precipitated. The slurry was stirred for one hour, then filtered over paper, washed to neutrality with water, then dried at 50° C. and 26 inches vacuum with a nitrogen purge to furnish 17.6 g 3-hydroxyketoisophorone as a yellowish solid. The yield is estimated at 90%. mp 137–139 (lit. 141–143).

Example 23

Preparation of 3-Methoxyketoisophorone

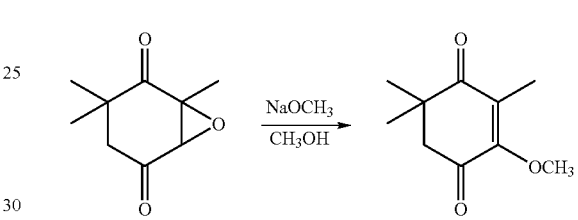

0.17 g epoxyketoisophorone (1.01 mmole) was dissolved in 2 mL dry methanol under an argon atmosphere. Sodium methoxide was added to the reaction causing the reaction to darken, after an hour at room temperature the reaction was heated to 50° C. The solvents were removed under reduced pressure, the reaction was worked up with water and methylene chloride. The methylene chloride phase was extracted with two portions of a sodium chloride solution and dried over sodium sulphate. The product resulted as a yellow oil (128 mg) with which the NMR spectra was consistent with the desired product.

Example 24

Preparation of 3-Methoxyketoisophorone

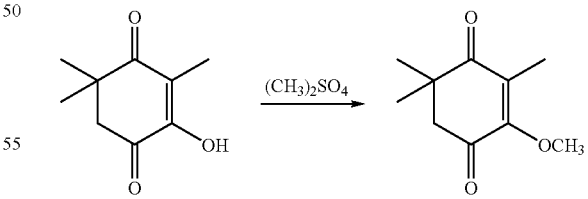

To a 3-neck round bottom flask fitted with a heating mantle, an addition funnel, a magnetic stirrer, and a reflux condenser were charged 1.68 g 3-hydroxyketoisophorone (10 mmole) and 10 mL methanol and 11 mL 1 N sodium hydroxide and the mixture stirred to furnish a yellow solution. To the solution was added dropwise 1.50 g dimethylsulfate which caused clouding. The resulting mixture was stirred vigorously for 2 hours at 20° C. then warmed to reflux. The homogeneous solution was held at reflux for 4 hours. TLC showed the reaction to be incomplete with no change after another 2 hours. On cooling the reaction mixture was combined with 25 ml water then extracted three times, each time with 50 ml dichloromethane. The combined dichloromethane phases were extracted with 25 ml 5 wt % sodium carbonate and 25 ml 20 wt % sodium chloride then dried over anhydrous sodium sulfate. The filtered solution was stripped of solvent in a rotovac to 50° C. and 26 inches vacuum to furnish a straw colored oil of 1.2 g 3-methoxyketoisophorone. Yield is estimated at 70%. NMR of the product showed it to be >90% pure. $^{1}$H NMR: 1.25 (s, 6H), 1.90 (s, 3H), 2.70 (s, 2H), 4.00 (s, 3H).

Example 25

Preparation of 3-Methoxyketoisophorone

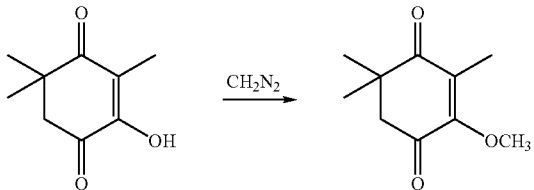

0.17 g 3-hydroxyketoisophorone (1.01 mmole) was dissolved in 3 mL methanol at 0° C. Diazomethane in ether was added dropwise to the solution to control foaming and spattering. Addition was continued until a yellow color persisted (~8 mL). Reaction was allowed to continue for one hour, and solvents removed. A yellow oil (186 mg) resulted with an NMR consistent with the desired product.

Example 26

Preparation of 3-Methoxyketoisophorone

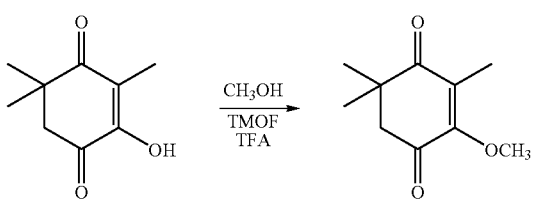

0.2 g 3-hydroxyketoisophorone (1.19 mmole) was dissolved in methanol. 0.8 g trimethyl orthoformate and 0.04 g trifluoroacetic acid were added to the solution. The reaction was heated to 50° C.

Example 27

Preparation of 3-Methoxyketoisophorone

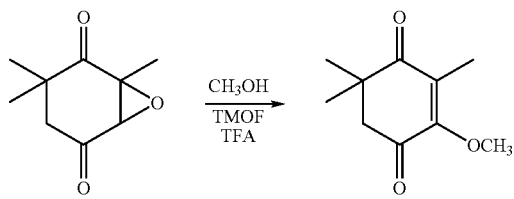

0.107 g epoxyketoisophorone (0.64 mmole) was dissolved in 1.0 mL methanol under an argon atmosphere. Trimethyl orthoformate and trifluoroacetic acid were added to the solution. The reaction was heated to 50° C. and allowed to stir overnight.

Example 28

Preparation of 3-Methoxyketoisophorone

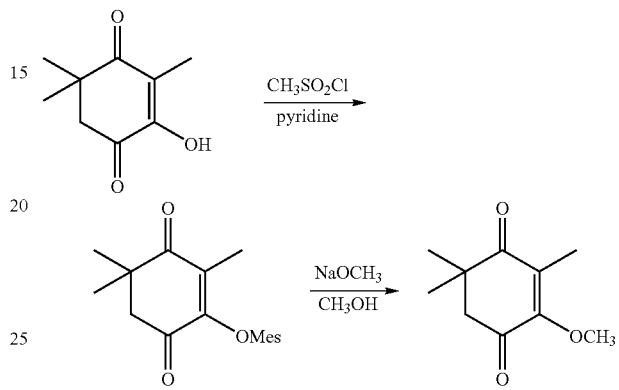

0.5 g 3-hydroxyketoisophorone (2.98 mmole) was dissolved in 2 mL dry pyridine and 9 mL methylene chloride under an argon atmosphere. MesCl was added in one portion and the reaction was stirred overnight. The reaction was stripped of solvents, and methanol under argon was added (the precipitates were not completely soluble). Sodium methoxide was added resulting in a dark red color and the reaction was stirred at room temperature for six hours. The reaction was checked by TLC, the product was present in apparently low yields.

Example 29

Preparation of 4-(S)-Hydroxy-ketoisophorone

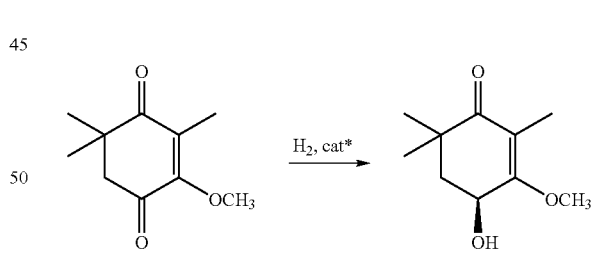

To a 50 ml round bottom flask fitted magnetic with a stirrer and a septum with Argon purge was charged 10 ml isopropanol and 11.2 mg dichloro (p-cymene) ruthenium dimer and 26.8 mg 1S, 2S (+)-N-p-luenesulfonyl, 1,2-diphenylethylenediamine and the mixture heated to 80° C. for thirty minutes then cooled to 20° C. To the mixture was charged 670 mg 3-methoxyketoisophorone in degassed 15 ml isopropanol and 1.8 ml 0.1 M potassium hydroxide in isopropanol and the reaction mixture stirred overnight. The reaction mixture was neutralized by adding a solution of 35 mg citric acid in 1 ml water, the mixture filtered through a small pad of silica gel, them stripped to dryness on a rotovac. The residue was chromatographed over 40 g silica gel using a gradient of ethyl acetate-hexanes 20:80 to 40:60 v/v. On concentration of fractions and stripping in vacuo was obtained 589 mg 4-hydroxyketoisophorone as a white crystalline solid. Yield was estimated at 87%. $^1$H NMR: 1.10 (s, 3H), 1.22 (s, 3H), 1.75 (s, 3H), 1.9 (m, 1H), 2.2 (d, d, 1H) 4.0 (s, 3H), 4.7 (m, 1H).

Example 30

Preparation of 4-Hydroxy-ketoisophorone

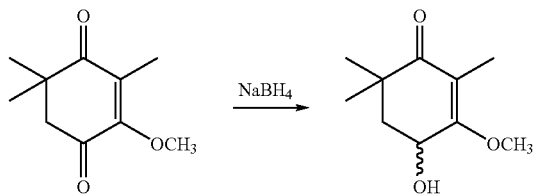

70 mg 3-methoxyketoisophorone (0.38 mmole) was dissolved in methanol (2 mL) under an argon atmosphere. Sodium borohydride (50 mg) was added to the reaction in one portion and the reaction was stirred at room temperature for 0.5 hours. Solvents were removed under reduced pressure and worked up with water (0.5 mL) and methylene chloride (2.0 mL). Methylene chloride fraction was dried over sodium sulfate and the solvent removed under reduced pressure. A colorless oil resulted (39 mg).

Example 31

Preparation of 4-Hydroyxketoisophorone acetone ketal

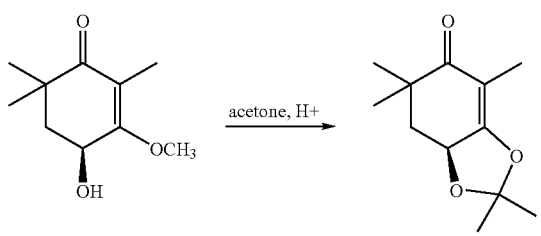

To a 50 ml round bottom flask fitted with a reflux condenser and a magnetic stirrer were charged 587 mg 4-hydroxyketoisophorone and 5 ml acetone and 10 ml 2,2-dimethoxypropane and 30 mg p-toluenesulfonic acid hydrate and 150 mg water and the mixture heated to reflux. At intervals of two hours an additional 150 mg water were added each time and after the fourth addition reflux continued for an additional two hours. The cooled reaction mixture was neutralized by addition of 0.2 ml saturated sodium bicarbonate solution then stripped in vacuo to near dryness. The residue was extracted with ethyl acetate and water, the organic phase dried with sodium sulfate then concentrated in vacuo. The residue was chromatographed on 40 g silica gel eluting with ethyl acetate-hexanes 15:85 to 25:75. The combined and stripped product fractions furnished 537 mg ketal as an oil which later crystallized. The yield is estimated at 80%. Chiral HPLC showed an enantiomeric excess of 98%. I H NMR: 1.18 (s, 3H), 1.20 (s, 3H), 1.55 (s, 3H), 1.63 (s, 3H), 1.70 (s, 3H), 1.85 (d, d, 1H), 2.20 (d, 1H), 4.90 (m, 1H).

Example 32

Bulk Chromatographic Separation of the Diastereomeric Dicamphanic Acid Ester(s) of Astaxanthin Bulk chromatographic separation of the diastereomeric dicamphanic acid ester(s) of synthetic astaxanthin at preparative chromatography scale was performed to subsequently make gram-scale quantities of each stereoisomer of disodium disuccinate ester astaxanthin. A total of 135 g of astaxanthin dicamphanate esters (ASTA-DCE) prepared by derivatization of racemic astaxanthin with (−)-camphanic acid chloride were fractionated by preparative HPLC (using a 77 mm i.d. 25 cm column formed by packing 550 g of 10 µm Kromasil 60 Å silica; Eka Chemicals, Marietta, GA) into a Varian RamPak column packing station. After the dry column packing material was mixed with 1200 mL of toluene/2-propanol (50/50) and the resulting slurry was transferred to the 77 mm i.d. column packing chamber, the column bed was formed using the dynamic axial compression of the RamPak unit. The packing solvent was flushed from the column bed for 50 min at a flow rate of 150 m/min using the preparative HPLC mobile phase consisting of 95% toluene and 5% methyl ethyl ketone (MEK). The preparative HPLC system consisted of a Waters Prep 4000 solvent delivery system and a Waters model 486 variable UV detector fitted with a prep cell (3 mm path length). Sample solution was injected directly through the pump, detection was at 580 nm, and the chromatogram was recorded on a strip chart recorder. At the preparative flow rate of 280 mL/min, the system backpressure was 840 psi. The laboratory was equipped with yellow lights, and the windows were covered to avoid any effects of light on the sample. A sample solution for preparative HPLC was prepared by dissolving 30 g of ASTA-DCE in 90 mL of methylene chloride and diluting the solution with 210 mL of toluene. A portion of the resulting solution (272 mL) was further diluted with 688 mL of preparative HPLC mobile phase to generate the sample solution that was subsequently injected onto the preparative HPLC system. The preparative HPLC injection consisted of pumping 120 mL of this ASTA-DCE sample solution (3.4 g of ASTA-DCE) through the pump and onto the preparative column. The preparative loading was selected to optimize sample throughput, and the resulting chromatogram consisted of three slightly overlapping peaks with the 3R, 3'R ester eluting at 14 min, the meso-(3R, 3'S) ester at 16.5 min, and the 3S, 3'S ester at 21.5 min. To take advantage of the blank section of the chromatogram for the first 10 min, subsequent injections were made 20 min into the previous run at the valley between the meso and 3S, 3'S peaks. Heart cuts of each of the three peaks were collected in addition to the mixed fractions at the overlap of the 3R, 3'R/meso and the meso/3S, 3'S peaks.

A total of 40 preparative injections were processed using 84 L of mobile phase. Thirty-six (36) L of effluent were collected among the five fractions. The preparative system was flushed with 100 mL of methylene chloride approximately every 6–8 injections or whenever the chromatographic separation deteriorated due to effects from mixing with mobile phase in the pump heads during the injection process. Purified materials were recovered by removing the solvents in a rotary evaporator protected from light to afford 25.4 g of 3R, 3'R ester, 47.8 g of meso-(3R, 3'S) ester, and 24.9 g of 3S, 3'S ester. The purified astaxanthin dicamphanate esters were saponified to afford 8.5 g (79.8% purity by HPLC) of 3R, 3'R-astaxanthin, 18.2 g (90.1% purity by HPLC) of meso-astaxanthin, and 9.4 g (82.0% purity by HPLC) of 3S, 3'S-astaxanthin. The major impurities of the saponification reaction were the 13- and 9-cis isomers of astaxanthin, identified by HPLC. The cis-isomers were thermally isomerized to all-trans by refluxing in heptane to afford 8.5 g (87.3% purity by HPLC) of 3R, 3'R-astaxanthin, 18.2 g (92.5% purity by HPLC) of meso-astaxanthin, and 9.4 g (86.8% purity by HPLC) of 3S, 3'S-astaxanthin.

Example 34

General Preparation of Lycophyll 2H

Crocetindialdehyde (238) was obtained from SynChem, Inc. (Des Plaines, Ill.) as a brick-red solid and was used without further purification. Lycopene was obtained from ChromaDex (Santa Ana, Calif.) as a red solid and was used without further purification. Acetic acid 3,7-dimethyl-8-oxo-octa-2,6-dienyl ester (230a) (Liu and Prestwich 2002) was synthesized by literature procedures from commercially available geranyl acetate (228a). All other reagents and solvents used were purchased from Acros Organics (Morris Plains, NJ) and Sigma-Aldrich (St. Louis, Mo.) and were used without further purification. All reactions were performed under a nitrogen atmosphere. All flash chromatographic purifications were performed on Natland International Corporation 230–400 mesh silica gel using indicated solvents. LC/MS (APCI and ESI+ modes) were recorded on an Agilent 1100 LC/MSD VL system; column: Zorbax Eclipse XDB-C18 Rapid Resolution (4.6x75 mm, 3.5 µm); temperature: 25° C.; flow rate: 1.0 mL/min.; mobile phase (A=0.025% TFA in $H_2O$, B=0.025% TFA in acetonitrile). Gradient program (for intermediates 230a–236a and 216a): 70% A/30% B (start), step gradient to 50% B over 5 minutes, step gradient to 100% B over 1.3 minutes, hold at 100% B over 4.9 minutes. Gradient program (for intermediates 218a, 2H): 70% A/30% B (start), step gradient to 50% B over 5 minutes, step gradient to 98% B over 3.3 minutes, hold at 98% B over 16.9 minutes. All-trans lycophyll was obtained from crude material using a Waters 996 Photo Diode Array detector, Millipore 600E System Controller and Waters 717 Autosampler; column: YMC C30 Carotenoid S-5, (10×250 mm, 5 µm column); temperature: 25° C.; flow rate: 4.7 mL/min; mobile phase (A=methanol (MeOH), B=methyl-t-butyl ether (MTBE)) Gradient program: 60% A/40% B (start), step gradient to 80% A over 1 minute, hold at 80% A over 119 minutes. Fractions were collected from 55-66 minutes. Fraction analysis was performed on a YMC C30 Carotenoid S-5, (4.6×250 mm, 5 µm column). Proton nuclear magnetic resonance (NMR) spectra were obtained on a Varian Unity INOVA 500 spectrometer operating at 500.111 MHz (megahertz). Electronic absorption spectra were recorded on a Cary 50 Bio UV-Visible spectrophotometer.

Example 35

Preparation of
8-Acetoxy-2,6-dimethyl-octa-2,6-dienoic acid
(232a)

To a solution of aldehyde 230a (19.5 g, 92.7 mmol) in 300 mL of tert-butyl alcohol was added 2-methyl-2-butene (98.0 mL, 925 mmol). To this was added a solution of sodium dihydrogen phosphate (44.5 g, 371 mmol) in 300 mL of water. Sodium chlorite (33.6 g, 371 mmol) was added in several portions. The resulting mixture was rapidly stirred overnight at room temperature. Ethyl acetate was added and the aqueous layer was acidified to pH 3 by addition of 1 M HCl. The organic layer was separated, and the aqueous layer was extracted with ethyl acetate (3×200 mL). The combined organic extracts were washed with brine, dried over $MgSO_4$, and reduced to dryness in vacuo. The crude product (27.4 g, 121 mmol, >100% yield) was used in the next step without further purification: $^1$H NMR (500 MHz, $CDCl_3$) δ: 6.84(t of q, J=7.25 Hz, J=1.50 Hz, 1H, =CH), 5.34 (t of q, J=7.00 Hz, J=1.50 Hz, 1H, =CH), 4.56 (d, J=7.00 Hz, 2H, —$CH_2$O—), 2.31 (q, J=7.50 Hz, 2H, —$CH_2$—), 2.15 (t, J=7.50 Hz, 2H, —$CH_2$—), 2.03 (s, 3H, —$CH_3$), 1.81 (s, 3H, —$CH_3$), 1.70 (s, 3H, —$CH_3$). LC/MS (ESI): m/z 249 [M+Na]$^+$.

Example 36

Preparation of
8-Hydroxy-2,6-dimethyl-octa-2,6-dienoic acid
(234a)

To a solution of acid 232a (20.0 g, 88.4 mmol) in 400 mL of methanol was added a solution of potassium carbonate (24.4 g, 177 mmol) in 100 mL of water. The resulting mixture was vigorously stirred overnight at room temperature. The reaction was cooled to 0° C., methylene chloride (200 mL) was added, and the aqueous layer was acidified to pH 3 with 1 M HCl. The organic layer was separated, and the aqueous layer was extracted with methylene chloride (2×200 mL). The combined organic extracts were washed with brine, dried over $MgSO_4$, and reduced to dryness in vacuo. The crude product (9.65 g, 52.4 mmol, 59% yield) was used in the next step without further purification: $^1$H NMR (500 MHz, $CDCl_3$) δ: 6.86 (t of q, J=7.25 Hz, J=1.50 Hz, 1H, =CH), 5.43 (t of q, J=7.00 Hz, J=1.50 Hz, 1H, =CH), 4.16 (d, J=7.00 Hz, 2H, —$CH_2$O—), 2.33 (q, J=7.50 Hz, 2H, —$CH_2$—), 2.16 (t, J=7.50 Hz, 2H, —$CH_2$—), 1.83 (s, 3H, —$CH_3$), 1.68 (s, 3H, —$CH_3$). LC/MS (ESI): m/z 207 [M+Na]$^+$.

Example 37

Preparation of
8-Hydroxy-2,6-dimethyl-octa-2,6-dienoic acid
methyl ester (234b)

To a solution of acid 234a (20.1 g, 109 mmol) in 400 mL of DMF was added a solution of potassium carbonate (16.6 g, 120 mmol) in 80 mL of water. The resulting mixture was vigorously stirred for several minutes. To the mixture was added iodomethane (7.50 mL, 120 mmol) via syringe. The resulting mixture was vigorously stirred overnight at room temperature. Ethyl acetate (400 mL) and water (400 mL) were added and the aqueous layer was acidified to pH 3 by addition of 1 M HCl. The organic layer was separated and the aqueous layer was extracted with ethyl acetate (3×200 mL). The combined organic extracts were washed with water (3×500 mL), saturated aqueous sodium carbonate, brine, and dried over $MgSO_4$. The solvent was removed under reduced pressure and the crude product purified by flash chromatography (MeOH/$CH_2Cl_2$, 1:49) to afford methyl ester 5 as a clear oil (19.4 g, 90% yield): $^1$H NMR (500 MHz, $CDCl_3$) δ: 6.72 (t of q, J=7.50 Hz, J=1.50 Hz, 1H, =CH), 5.43 (t of q, J=6.75 Hz, J=1.50 Hz, 1H, =CH), 4.16 (d, J=7.00 Hz, 2H, —CH$_2$O—), 3.73(s, 3H, —CH$_3$), 2.31 (q, J=7.50 Hz, 2H, —CH$_2$—), 2.15 (t, J=7.50 Hz, 2H, —CH$_2$—),1.83 (s, 3H, —CH$_3$),1.69 (s, 3H, —CH$_3$). LC/MS (ESI): m/z 221 [M+Na]$^+$.

Example 38

Preparation of 8-Bromo-2,6-dimethyl-octa-2,6-dienoic acid methyl ester (236a)

To a 0° C. solution of alcohol 234b (12.9, 64.9 mmol) in 250 mL of anhydrous tetrahydrofuran was added carbon tetrabromide (23.8 g, 71.4 mmol) in several portions. The mixture was stirred for a few minutes and then triphenylphosphine (18.7 g, 71.4 mmol) was added and the mixture allowed to warm to room temperature and stirred overnight. The solvent was removed under reduced pressure and the resulting residue was suspended in diethyl ether. The suspension was filtered through a pad of Celite. After solvent removal under reduced pressure the resulting crude product (contaminated with triphenylphosphine oxide) was used directly in the next step: $^1$H NMR (500 MHz, CDCl$_3$) δ: 6.61 (t of q, J=7.50 Hz, J=1.50 Hz, 1H, =CH), 547 (t of q, J=8.00 Hz, J=1.50 Hz, 1H, =CH), 3.92 (d, J=8.50 Hz, 2H, —CH$_2$Br), 3.63 (s, 3H, —CH$_3$), 2.22 (q, J=8.00Hz, 2H, —CH$_2$—),2.10 (t, J=8.00 Hz, 2H, —CH$_2$—),1.75 (d, J=1.00 Hz, 3H, —CH$_3$),1.66 (d, J=1.00 Hz, 3H, —CH$_3$).

Example 39

Preparation of (2,6-Dimethyl-8-octa-2,6-dienoic acid methyl ester)triphenylphosphonium bromide (216a)

To a solution of bromide 236a (9.20 g, 35.2 mmol) in ethyl acetate (200 mL) was added triphenylphosphine (10.2 g, 38.8 mmol). The resulting mixture was vigorously stirred for a few minutes, at which time an insoluble material began to oil out from the solution, adhering to the sides of the flask. The reaction solution was then decanted into a clean reaction vessel. This procedure was repeated every 5 to 10 minutes until no more oily insoluble residue was noted, at which time a white solid started to precipitate from the solution. The cloudy mixture was then stirred overnight at room temperature. The mixture was filtered and the filter cake was rinsed with ethyl acetate and dried in vacuo to afford phosphonium salt 7 as a white solid (9.60 g, 52% yield). $^1$H NMR (500 MHz, CDCl$_3$) δ: 7.88–7.84 (m, 6 arom. H), 7.79–7.75 (m, 3 arom. H), 7.68–7.64 (m, 6 arom. H), 6.51 (t of q, J=5.00 Hz, J=1.00 Hz, 1H, =CH), 5.10 (q, J=7.00 Hz, 1H, =CH), 4.70 (d of d, J=15.0, J=8.00 Hz, 2H, —CH$_2$PPh$_3$Br), 3.67 (s, 3H, —CH$_3$), 2.16 (q, J=7.00 Hz, 2H, —CH$_2$—), 2.08 (t, J=6.00 Hz, 2H, —CH$_2$—), 1.70 (s, 3H, —CH$_3$),1.35 (d, J=4.00 Hz, 3H, —CH$_3$). LC/MS (ESI): m/z 443 [M]+.

Example 40

Preparation of Dimethyl ψ,ψ-Carotene-16,16'-dioate (218a)

To a solution of crocetindialdehyde (238) (0.810 g, 2.74 mmol) and 216a (4.30 g, 8.21 mmol) in toluene (100 mL) was added 1 M LiOMe in MeOH (7.67 mL, 7.67 mmol) via syringe. The resulting mixture was refluxed for 24 hours, cooled to room temperature, and then water (100 mL) was added. The organic phase was collected, extracted with water twice, and then dried over anhydrous sodium sulfate. After filtration and removal of the solvent in vacuo, the resulting residue was purified by flash chromatography (ethyl acetate:toluene, 1:99) to afford dimethyl ester 240 as a red solid (1.15 g, 67% yield). LC/MS (APCI): m/z 625 [M+H]$^+$.

Example 41

Preparation of ψ,ψ-Carotene-16,16'-diol (I)

To a solution of dimethyl ester 218a (1.14 g, 1.83 mmol) in anhydrous tetrahydrofuran (100 mL) at 0° C. was added DIBAL (20% by wt. in toluene) (9.13 mL, 11.0 mmol) via syringe. The mixture was warmed to room temperature and stirred for one hour. The reaction was quenched by the sequential addition of H$_2$O (440 µL), 15% aqueous NaOH (440 µL), and H$_2$O (1.10 mL). The resulting mixture was stirred for 30 minutes and then dried over anhydrous MgSO$_4$. After filtration and removal of solvent in vacuo, the resulting crude diol 2H (0.39 g, 38%) was used in the next step without further purification. $^1$H NMR (500 MHz, CDCl$_3$) δ: 6.63 (d of d, J=15.0 Hz, J=11.5 Hz, 2H, H11, H11'), 6.63 (d, J=11.0 Hz, 2H, H15, H15'), 6.48 (d of d, J=15.0 Hz, J=11.0 Hz, 2H, H7, H7'), 6.36 (d, J=15.0 Hz, 2H, H12, H12'), 6.25 (d, J=15.0 Hz, 2H, H8, H8'), 6.19 (d, J=11.5 Hz, 2H, H10, H10'), 5.95 (d, J=11.0 Hz, 2H, H6, H6'), 5.40 (t of q, J=6.50 Hz, J=1.50 Hz, 2H, H2, H2'), 4.00 (s, 4H, —CH$_2$O—), 2.19 (t, J=Hz, 4H, —CH$_2$—), 2.16 (t, J=Hz, 4H, —CH$_2$—), LC/IMS (APCI): m/z 569 [M+H]$^+$.

Example 42

General Preparation of Lycophyll Derivatives

LC/MS (APCI) and LC/MS (ESI) were recorded on an Agilent 1100 LC/MSD VL, PDA detector system; column: Zorbax Eclipse XDB-C18 Rapid Resolution (4.6×75 mm, 3.5 µm); temperature: 25° C.; flow rate: 1.0 mL/min; mobile phase (% A=0.025% trifluoroacetic acid in H$_2$O, % B=0.025% trifluoroacetic acid in acetonitrile) Gradient program: 70% A/30% B (start), step gradient to 50% B over 5 min, step gradient to 98% B over 8.30 min, hold at 98% B over 25.20 min, step gradient to 30% B over 25.40 min. A catalytic amount of trifluoroacetic acid is used in the eluents to improve chromatographic resolution. The presence of trifluoroacetic acid facilitates the protonation of synthesized lycophyll dissucinate and diphosphate salts to give the free diacid forms (as represented by the theoretical molecular ions M$^+$=768 for lycophyll disuccinate salt and M$^+$=728 for lycophyll disphosphate salt). LRMS:+mode; ESI: electrospray chemical ionization, ion collection using quadrapole; APCI: atmospheric pressure chemical ionization, ion collection using quadrapole. Reverse-phase HPLC was performed on a Waters 996 HPLC with PDA detector, Millipore 600E System Controller system; column: Zorbax Eclipse XDB-C18 (9.4×250 mm, 5 µm); temperature: 25° C.; flow rate: 2.1 mU min; mobile phase (% A=0.025% trifluoroacetic acid in H$_2$O, % B=0.025% trifluoroacetic acid in MeOH) Isocratic program: 15% A/85% B. $^1$H NMR analyses were performed on a Varian spectrometer (300 MHz).

Example 43

Preparation of ψ,ψ-carotenyl 16,16'-disuccinate (222a)

To a solution of lycophyll (2H) (0.10 g, 0.176 mmol) in $CH_2Cl_2$ (2 mL) was added N,N-diisopropylethylamine (0.613 mL, 3.52 mmol) and succinic anhydride (0.1761 g, 1.76 mmol). The solution was stirred at room temperature overnight and then diluted with $CH_2Cl_2$ and quenched with cold water/1 M HCl (9/1). The aqueous layer was extracted two times with $CH_2Cl_2$ and the combined organic layer was washed three times with cold water/1 M HCl (9/1), dried over $Na_2SO_4$, and concentrated to yield disuccinate 222a (0.124 g, 92%) as a red hygroscopic solid; LC/MS (APCI): 11.59 min (65.17%), $\lambda_{max}$ 295 nm (28%), 362 nm (8%), 447 nm (72%), 472 nm (100%), 503 nm (93%), m/z 769 [M+H]$^+$ (100%), 668 [M—$C_4O_3H_4$]$^+$ (9%), 651 (89%), 533 (30%); 12.13 min (33.69%), $\lambda_{max}$ 295 nm (26%), 362 nm (10%), 447 nm (77%), 472 nm (100%), 503 nm (91%), m/z 769 [M+H]$^+$ (28%), 651 (24%), 531 (8%), 261 (100%).

Example 44

Preparation of ψ,ψ-carotenyl 16,16'-disuccinate sodium salt (224a)

To a solution of disuccinate 222a (0.124 g, 0.161 mmol) in methanol (3 mL) at 0° C. was added dropwise sodium methoxide (25% wt in methanol; 0.074 mL, 0.322 mmol). The solution was stirred at room temperature overnight, then cooled to 0° C., and water was added. The red mixture was stirred for 5 min at 0° C., and then methanol was removed in vacuo. The red, aqueous solution was lyophilized to afford disuccinate salt 224a (0.103 g, 88%) as a red hygroscopic solid; LC/MS (APCI): 11.58 min (71.72%), $\lambda_{max}$ 295 nm (13%), 362 nm (9%), 447 nm (68%), 472 nm (100%), 503 nm (90%), m/z 769 [M+H]$^+$ (100%), 651 (42%), 533 (15%); 12.09 min (27.74%), $\lambda_{max}$ 295 nm (31%), 362 nm (19%), 447 nm (80%), 472 nm (100%), 503 nm (88%), m/z 769 [M+H]$^+$ (100%), 669 [M-$C_4O_3H_4$+H]$^+$ (12%), 651 (54%), 551 (8%), 533 (11%).

Example 45

Preparation of Tribenzyl phosphite (13)

To a well-stirred solution of phosphorus trichloride (1.7 mL, 19.4 mmol) in $Et_2O$ (430 mL) at 0° C. was added dropwise a solution of triethylamine (8.4 mL, 60.3 mmol) in $Et_2O$ (20 mL), followed by a solution of benzyl alcohol (8.1 mL, 77.8 mmol) in $Et_2O$ (20 mL). The mixture was stirred at 0° C. for 30 min and then at room temperature overnight. The mixture was filtered and the filtrate concentrated to give a colorless oil. Silica chromatography (hexanes/$Et_2O$/triethylamine, 5.5/1/1%) of the crude product gave 13 (5.68 g, 83%) as a clear, colorless oil that was stored under $N_2$ at −20° C.; $^1$H NMR (300 MHz, $CDCl_3$) δ: 7.38 (15H, m), 4.90 (6H, d).

Example 46

Preparation of Dibenzyl Phosphoroiodidate (14)

To a solution of tribenzyl phosphite (0.708 g, 2.01 mmol) in $CH_2Cl_2$ (5 mL) at 0° C. was added 1.93 mmol). The mixture was stirred at 0° C. for 10 min or until the solution became clear and colorless. The solution was then stirred at room temperature for 10 min and used directly in the next step.

Example 47

Preparation of Mixture of 16,16'-Benzyl phosphoryloxy-ψ,ψ-carotenes (221a,221b,221c,221d)

To a solution of lycophyll (2H) (0.11 g, 0.193 mmol) in $CH_2Cl_2$ (5 mL) was added pyridine (0.624 mL, 7.72 mmol). The solution was stirred at 0° C. for 5 min and then freshly prepared 14 (1.93 mmol) in $CH_2Cl_2$ (5 mL) was added dropwise to the mixture at 0° C. The solution was stirred at 0° C. for 1 h and then diluted with $CH_2Cl_2$ and quenched with brine. The aqueous layer was extracted twice with $CH_2Cl_2$ and the combined organic layer was washed once with $NaSSO_4$, once with brine, then dried over $Na_2SO_4$ and concentrated. Pyridine was removed from the crude red oil by azeotropic distillation using toluene to yield a mixture of benzyl-protected diphosphoric acid lycophyll derivatives 221a,221b,221c,221d used in the next step without further purification; LCtMS (ESI) for 221a: 10.15 min (7.73%), $\lambda_{max}$ 295 nm (21%), 362 nm (16%), 447 nm (72%), 472 nm (100%), 503 nm (87%), m/z 819 [M+H]$^+$ (18%), 800 [M-$H_2O$]+(11%), 672 (24%), 531 (10%); LC for 221b: 18.00 min (17.46%), $\lambda_{max}$ 295 nm (18%), 362 nm (13%), 447 nm (74%), 472 nm (100%), 503 nm (85%); LC for 221c: 20.08 min (20.00%), $\lambda_{max}$ 295 nm (18%), 362 nm (16%), 447 nm (74%), 472 nm (100%), 503 nm (86%); LC for 221d: 22.52 min (54.81%), $\lambda_{max}$ 295 nm (19%), 362 nm (18%), 447 nm (73%), 472 nm (100%), 503 nm (87%).

Example 48

Preparation of 16,16'-Diphosphoryloxy-ψ,ψ-carotene (221e)

To a solution of a mixture of benzyl-protected diphosphoric acid lycophyll derivatives 221a, 221b, 221c, 221d (0.193 mmol) in $CH_2Cl_2$ (15 mL) at 0° C. was added dropwise N,O-bis(trimethylsilyl)acetamide (0.479 mL, 1.93 mmol) and then bromotrimethylsilane (0.203 mL, 1.54 mmol). The solution was stirred at 0° C. for 15 min, quenched with triethylamine, and stirred at 0° C. for 5 min. The red solution was then diluted with $CH_2Cl_2$, $Et_2O$, and MeOH (2/1/1), and then concentrated. The resulting red oil was resuspended in a minimum amount of MeOH and the cloudy solution was centrifuged to remove insoluble reaction byproducts. The red supernatant was concentrated to afford a mixture of monophosphate and diphosphate lycophyll derivatives (254/221e) (1/4) contaminated with excess reagents, and reaction and decomposition byproducts; LC/MS (ESI) for 221e: 9.10 min (39.24%), $\lambda_{max}$ 295 nm (31%), 362 nm (18%), 447 nm (74%), 472 nm (100%), 503 nm (88%), m/z 849 (25%), 827 (5%), 368 (100%), 357 (11%), 317 (52%); 9.25 min (37.83%), $\lambda_{max}$ 295 nm (31%), 362 nm (18%), 447 nm (75%), 472 nm (100%), 503 nm (89%), m/z 849 (10%), 625 (8%), 581 (6%), 385 (20%), 368 (100%), 357 (28%); LC/MS (ESI) for 254: 10.21 min (18.50%), $\lambda_{max}$ 295 nm (32%), 362 nm (24%), 447 nm (78%), 472 nm (100%), 503 nm (89%), m/z 648 M+(9%), 630 [M-$H_2O$]$^+$ (5%), 568 (10%), 317 (100%); the crude mixture was subjected to reverse-phase HPLC purification to give diphosphate 221e (approximately 70% pure; 0.063 g, 45%) as a red oil, contaminated with excess reagents, and reaction and decomposition byproducts; LC/MS (ESI): 9.36 min (4.43%), $\lambda_{max}$ 295 nm (30%), 362 nm (25%), 447 nm (79%), 472 nm (100%), 503 nm (82%), m/z 849 (16%), 619 (7%), 399 (23%), 368 (100%), 357 (10%), 317 (8%); 9.58 min (46.42%), $\lambda_{max}$ 295 nm (30%), 362 nm (15%), 447 nm (80%), 472 nm (100%), 503 nm (92%), m/z 849 (19%), 619 (5%), (399 (21%), 368 (100%), 357 (10%), 317 (9%); 9.67 min (49.15%), $\lambda_{max}$ 295 nm (28%), 362 nm (12%), 447 nm (77%), 472 nm (100%), 503 nm (95%), nm/z 849 (15%), 619 (5%), 399 (20%), 368 (100%), 357 (8%), 317 (6%).

Example 49

Preparation of 16,16'-Diphosphoryloxy-ψ,ψ-carotene sodium salt (223a)

To a solution of lycophyll diphosphate (221e) (approximately 70% pure; 0.04 g, 0.055 mmol) in methanol (2 mL) at 0° C. was added dropwise sodium methoxide (25% wt in methanol; 0.05 mL, 0.22 mmol). The solution was stirred at room temperature overnight, then cooled to 0° C., and water was added. The red mixture was stirred for 5 min at 0° C., and then methanol was removed in vacuo. The red, aqueous solution was lyophilized to yield diphosphate salt 223a (approximately 50% pure; 0.018 g, 43%) as a red hygroscopic solid; LC/MS (ESI): 9.26 min (9.34%), $\lambda_{max}$ 295 nm (28%), 362 nm (18%), 447 nm (81%), 472 nm (100%), 503 nm (87%), m/z 897 (8%), 392 (100%), 381 (10%); 9.48 min (46.98%), $\lambda_{max}$ 295 nm (29%), 362 nm (15%), 447 nm (80%), 472 nm (100%), 503 nm (91%), m/z 911 (10%), 849 (15%), 399 (87%), 368 (100%); 9.56 min (43.68%), $\lambda_{max}$ 295 nm (28%), 362 nm (12%), 447 nm (77%), 472 nm (100%), 503 nm (90%), m/z 849 (19%), 827 (5%), 368 (100%), 357 (8%).

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

Example 50

Separation of (3S,3'S)-all-E-astaxanthin

Analysis of the stereoisomeric distribution of astaxanthin was accomplished using a chiral HPLC column. A Regis Pirkle Covalent D-phenylglycine, 5 Å, 4.6×250 nm chiral HPLC column was used. The detector was set at 474 nm. A 10 μL sample was injected into the column. The sample was passed through the column using a mobile phase of 75% Heptane, 24% dichloromethane, and 1% ethanol at a flow rate of 1.5 mL/min. Racemic astaxanthin (e.g., 3S, 3'S, meso (3R, 3'S), and 3R, 3'R in a 1:2:1 ratio) was run through the chiral HPLC column and the retention time for 3S, 3'S ("S, S")-astaxanthin was 32.763 min, meso-astaxanthin was 31.165, and 3R,3'R ("R, R")-astaxanthin was 29.937. The total run time was 60 minutes.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description to the invention. Changes may be made in the elements described herein without departing from the spirit and scope of the invention as described in the following claims. In addition, it is to be understood that features described herein independently may, in certain embodiments, be combined.

What is claimed is:

1. A method of producing astaxanthin comprising:
contacting a diketone compound having the structure:

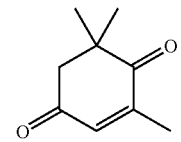

with an optically active chiral catalyst, to stereoselectively reduce the diketone to give a hydroxy product having the structure:

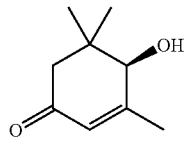

wherein the hydroxy product is optically active;

contacting the hydroxy product with a reducing agent to form a dihydroxy compound:

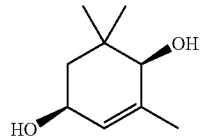

wherein the dihydroxy compound is optically active; and using the dihydroxy compound to form astaxanthin.

2. The method of claim 1, wherein the chiral catalyst comprises metal and an optically active chiral ligand.

3. The method of claim 1, wherein the chiral catalyst comprises ruthenium and an optically active chiral ligand.

4. The method of claim 1, wherein the chiral catalyst comprises ruthenium and an optically active amine.

5. The method of claim 1, wherein the chiral catalyst comprises ruthenium and an optically active amino acid.

6. The method of claim 1, wherein the chiral catalyst comprises ruthenium and an optically active amine having the structure $H_2N$-CHPh-CHPh-OH.

7. The method of claim 1, wherein the chiral catalyst comprises ruthenium and an optically active amine having the structure $H_2N$-CHMe-CHPh-OH.

8. The method of claim 1, wherein the chiral catalyst comprises ruthenium and an optically active amine having the structure MeHN-CHMe-CHPh-OH.

9. The method of claim 1, wherein the reducing agent comprises a borohydride reducing agent.

10. The method of claim 1, wherein the reducing agent comprises a lithium trialkyl borohydride reducing agent.

11. The method of claim 1, wherein the reducing agent comprises an aluminum hydride reducing agent.

12. The method of claim 1, further comprising:
converting the dihydroxy compound into a protected ketone having the structure:

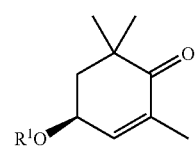

where $R^1$ is alkyl, phenyl, aryl or alkylsilyl.

13. The method of claim 12, further comprising:
converting the protected ketone into an unsaturated ketone having the structure:

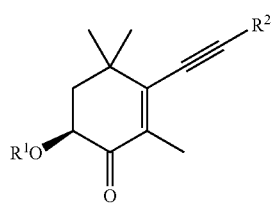

where $R^1$ is alkyl, phenyl, aryl or alkylsilyl, and $R^2$ is

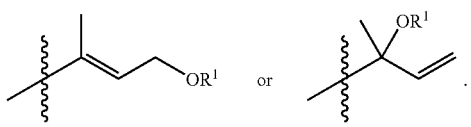

14. The method of claim 13, wherein forming the unsaturated ketone comprises:
reacting the protected ketone with an acetylinic compound having the structure:
$M^+$—C≡C—$R^2$, where M is a metal and $R^2$ is

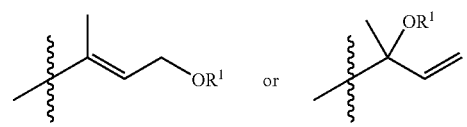

to give an addition product having the structure:

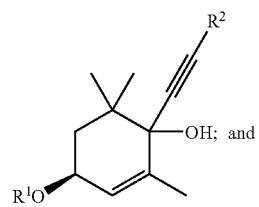

reacting the addition product with an oxidant to give the unsaturated ketone.

15. The method of claim 13, further comprising:
converting the unsaturated ketone into a compound having the structure:

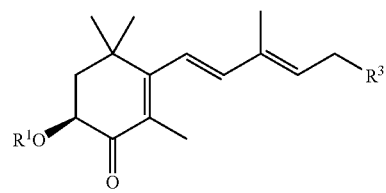

where $R^1$ is alkyl, phenyl, aryl or alkylsilyl; and $R^3$ is $PR^4_3$, $P(O)R^4_3$, $SO_2R^4$, or
$M^+$ where $R^4$ is alkyl, phenyl, or aryl and M is Li, Na, or MgBr.

16. The method of claim 15, further comprising:
reacting the compound having the structure:

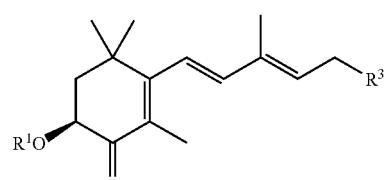

where $R^1$ is alkyl, phenyl, aryl or alkylsilyl; and $R^3$ is $PR^4_3$, $P(O)R^4_3$, $SO_2R^4$, or $M^+$ where $R^4$ is alkyl, phenyl, or aryl and M is Li, Na, or MgBr with a dialdehyde having the structure:

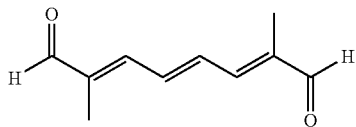

to form astaxanthin.

17. The method of claim 1, wherein astaxanthin is formed as the 3S, 3'S stereoisomer.

18. A method of producing astaxanthin comprising:
contacting a diketone compound having the structure:

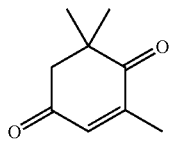

with a chiral catalyst, to stereoselectively reduce the diketone to give a hydroxy product having the structure:

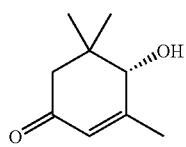

wherein the hydroxy product is optically active;
contacting the hydroxy product with a reducing agent to form a dihydroxy compound:

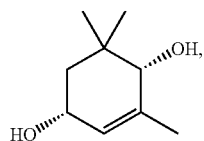

wherein the dihydroxy compound is optically active; and
using the dihydroxy compound to form astaxanthin.

19. The method of claim 18, wherein astaxanthin is formed as the 3R, 3'R stereoisomer.

20. The method of claim 18, wherein the chiral catalyst comprises ruthenium and an optically active amine.

21. The method of claim 18, wherein the chiral catalyst comprises metal and an optically active chiral ligand.

22. The method of claim 18, wherein the chiral catalyst comprises ruthenium and an optically active chiral ligand.

23. The method of claim 18, wherein the chiral catalyst comprises ruthenium and an optically active amino acid.

24. The method of claim 18, wherein the chiral catalyst comprises ruthenium and an optically active amine having the structure $H_2N$-CHPh-CHPh-OH.

25. The method of claim 18, wherein the chiral catalyst comprises ruthenium and an optically active amine having the structure $H_2N$-CHMe-CHPh-OH.

26. The method of claim 18, wherein the chiral catalyst comprises ruthenium and an optically active amine having the structure MeHN-CHMe-CHPh-OH.

27. The method of claim 18, wherein the reducing agent comprises a borohydride reducing agent.

28. The method of claim 18, wherein the reducing agent comprises a lithium trialkyl borohydride reducing agent.

29. The method of claim 18, wherein the reducing agent comprises an aluminum hydride reducing agent.

30. The method of claim 18, further comprising:
converting the dihydroxy compound into a protected ketone having the structure:

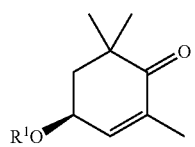

where $R^1$ is alkyl, phenyl, aryl or alkylsilyl.

31. The method of claim 30, further comprising:
converting the protected ketone into an unsaturated ketone having the structure:

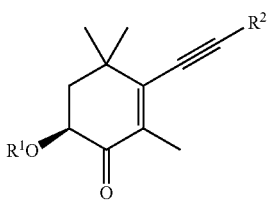

where $R^1$ is alkyl, phenyl, aryl or alkylsilyl, and $R^2$ is

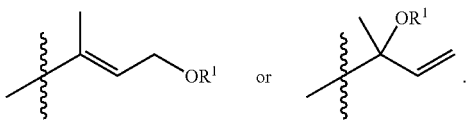

32. The method of claim 31, wherein forming the unsaturated ketone comprises:
reacting the protected ketone with an acetylinic compound having the structure:
$M^+$—C≡C—$R^2$, where M is a metal and $R^2$ is

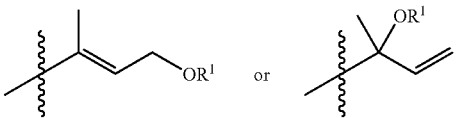

to give an addition product having the structure:

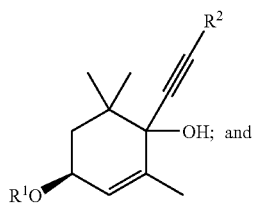

reacting the addition product with an oxidant to give the unsaturated ketone.

33. The method of claim 31, further comprising:
converting the unsaturated ketone into a compound having the structure:

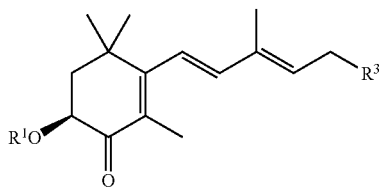

where $R^1$ is alkyl, phenyl, aryl or alkylsilyl; and $R^3$ is $PR^4_3$, $P(O)R^4_3$, $SO_2R^4$, or $M^+$where $R^4$ is alkyl, phenyl, or aryl and M is Li, Na, or MgBr.

34. The method of claim 33, further comprising:
reacting the compound having the structure:

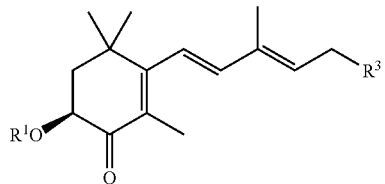

where $R^1$ is alkyl, phenyl, aryl or alkylsilyl; and $R^3$ is $PR^4_3$, $P(O)R^4_3$, $SO_2R^4$, or
$M^+$where $R^4$ is alkyl, phenyl, or aryl and M is Li, Na, or MgBr with a dialdehyde having the structure:

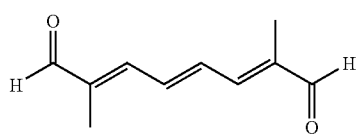

to form astaxanthin.

* * * * *